(12) United States Patent
Hailes et al.

(10) Patent No.: US 7,598,421 B2
(45) Date of Patent: Oct. 6, 2009

(54) MATERIALS FOR THE DELIVERY OF BIOLOGICALLY-ACTIVE MATERIAL TO CELLS

(75) Inventors: Helen C. Hailes, London (GB); Alethea B. Tabor, London (GB); John B. Wong, London (GB); Michael Pilkington-Miksa, London (GB); Stephen L. Hart, London (GB); Christopher A. Hurley, Hertfordshire (GB)

(73) Assignee: UCL Biomedica PLC, London (GB)

( * ) Notice: Subject to any disclaimer, the term of this patent is extended or adjusted under 35 U.S.C. 154(b) by 286 days.

(21) Appl. No.: 10/983,464

(22) Filed: Nov. 8, 2004

(65) Prior Publication Data

US 2005/0245446 A1    Nov. 3, 2005

Related U.S. Application Data

(63) Continuation-in-part of application No. PCT/GB03/01985, filed on May 8, 2003.

(60) Provisional application No. 60/576,270, filed on Jun. 2, 2004.

(30) Foreign Application Priority Data

May 8, 2002    (GB) ................... 0210538.5

(51) Int. Cl.
*C07C 217/00*    (2006.01)
*C12N 15/88*    (2006.01)

(52) U.S. Cl. .................... 564/295; 564/292; 564/294; 564/296; 562/583; 560/157; 435/458

(58) Field of Classification Search ........................ None
See application file for complete search history.

(56) References Cited

U.S. PATENT DOCUMENTS

| | | |
|---|---|---|
| 5,171,568 A | 12/1992 | Burke et al. |
| 5,264,618 A | 11/1993 | Felgner et al. |
| 5,334,761 A | 8/1994 | Gebeyehu et al. |
| 5,378,814 A | 1/1995 | Houghton et al. |
| 5,578,475 A | 11/1996 | Jessee |
| 5,824,812 A | 10/1998 | Nantz et al. |
| 5,869,715 A | 2/1999 | Nantz et al. |

FOREIGN PATENT DOCUMENTS

| | | |
|---|---|---|
| WO | WO 89/04669 | 6/1989 |
| WO | WO 90/11089 | 10/1990 |
| WO | WO 90/14436 | 11/1990 |
| WO | WO 96/15811 | 5/1996 |
| WO | WO 97/11935 | 4/1997 |
| WO | WO 98/54347 | 12/1998 |
| WO | WO 00/57917 | 10/2000 |
| WO | WO 00/73263 | 12/2000 |

OTHER PUBLICATIONS

Database CAPLUS on STN, Acc, No. 1999:409032, Baba et al., JP 11169174 (Jun. 29, 1999) (abstract).*
Database CAPLUS on STN, Acc. No. 2000:539522, Oida, Memoirs of the Faculty of Engineering and Design, Kyoto Institute of Technology, Series of Science and Technology (2000), vol. Date 1999, 48, p. 31-42 (abstract).*
Database CAPLUS on STN, Acc. No. 1992:447611, Osanai et al., Yukagaku (1992), 41(4), p. 293-300 (abstract).*
Baer et al., "DNA Sequence and Expression of the B95-8 Epstein—Barr Virus Genome," Nature 310:207-211, 1984.
Chee et al., "Analysis of the Protein-Coding Content of the Sequence of Human Cytomegalovirus Strain AD169," Current Topics in Microbiology and Immunology 154:125-169, 1990.
Clements et al., "Identification of a Key Integrin-Binding Sequence in VCAM-1 Homologous to the LDV Active Site in Fibronectin," J. Cell Sci. 107:2127-2135, 1994.
Cunningham et al., "Evaluation of a Porcine Model for Pulmonary Gene Transfer Using a Novel Synthetic Vector," J. Gene Med. 4:438-446, 2002.
Davison et al., "The Complete DNA Sequence of Varicella-Zoster Virus," J. Gen. Virol. 67:1759-1816, 1986.
Erbacher et al, "Gene Transfer with Synthetic Virus-Like Particles via the Integrin-Mediated Endocytosis Pathway," Gene Therapy 6:138-145, 1999.
Felgner et al., "Lipofection: A Highly Efficient, Lipid-Mediated DNA-Transfection Procedure," Proc. Natl. Acad. Sci. 84:7413-7417, 1987.
Fields et al., "Solid Phase Peptide Synthesis Utilizing 9-Fluorenylmethoxycarbonyl Amino Acids," Int. J. Peptide Protein Res. 35:161-214, 1990.
Harbottle et al., "An RGD-Oligolysine Peptide: A Prototype Construct for Integrin-Mediated Gene Delivery," Human Gene Ther. 9:1037-1047, 1998.
Hart et al., "Lipid-Mediated Enhancement of Transfection by a Nonviral Integrin-Targeting Vector," Human Gene Ther. 9:575-585, 1998.

(Continued)

*Primary Examiner*—Brian J Davis
(74) *Attorney, Agent, or Firm*—Clark & Elbing LLP

(57) ABSTRACT

The invention provides a lipid of general formula (I) or (II):

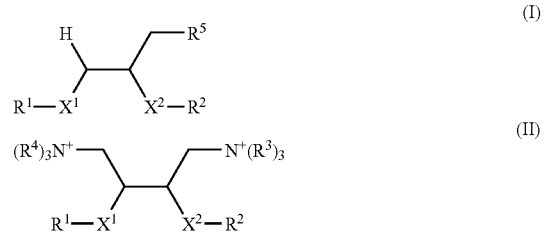

wherein $X^1$, $X^2$ and $R^1$ to $R^5$ are as defined herein. Such lipids are used to form complexes with a biologically-active material such as a nucleic acid, peptide or small molecule for delivering the biologically-active material to cells. The complexes may incorporate an integrin-binding peptide and, when the biologically-active material is DNA, thereby constitute a LID complex.

19 Claims, 4 Drawing Sheets

OTHER PUBLICATIONS

Healy et al., "Peptide Ligands for Integrin $\alpha_v\beta_3$ Selected from Random Phage Display Libraries," Biochem. 34:3948-3955, 1995.

Hervé et al., "The Selective Functionalisation and Difunctionalisation of p-Substituted Calix[6]arene and Calix[8]arenes Using Hydrophillc Moieties," Org. Biomol. Chem. 1:427-435, 2003.

Houghton et al., "Molecular Biology of the Hepatitis C Viruses: Implications for Diagnosis, Development and Control of Viral Disease," Hepatology 14:381-388, 1991.

Hurley et al., "Asymmetric Synthesis of Dialkyloxy-3-alkylammonium Cationic Lipids," J. Org. Chem. 69:980-983, 2004.

Jenkins et al., "An Integrin-targeted Non-Viral Vector for Pulmonary Gene Therapy," Gene Ther. 7:393-400, 2000.

Jenkins et al., "Formation of LID Vector Complexes in Water Alters Physicochemical Properties and Enhances Pulmonary Gene Expression In Vivo," Gene Ther. 10:1026-1034, 2003.

Koivunen et al., "Isolation of a Highly Specific Ligand for the $\alpha_5\beta_1$ Integrin from a Phage Display Library," J. Cell Biol. 124:373-380, 1994.

Koivunen et al., "Phage Libraries Displaying Cyclic Peptides with Different Ring Sizes: Ligand Specifities of the RGD-Directed Integrins," Bio/Technology 13:265-270, 1995.

Koivunen et al., "Selection of Peptides Binding to the $\alpha_5 \beta_1$ Integrin from Phage Display Library," J. Biol. Chem. 268:20205-20210, 1993.

Lu et al., "Synthetic RGD Peptides Derived from the Adhesive Domains of Snake-Venom Proteins: Evaluation as Inhibitors of Platelet Aggregation," J. Biochem. 296:21-24, 1993.

McGeoch et al., "The Complete DNA Sequence of the Long Unique Region in the Genome of Herpes Simplex Virus Type 1," J. Gen. Virol. 69:1531-1574, 1988.

Meng et al., "Efficient Transfection of Non-Proliferating Human Airway Epithelial Cells with a Synthetic Vector System," J. Gene Med. 6:210-221, 2004.

Merrifield, "Solid-Phase Peptide Synthesis," Adv. Enzymol. 32:221-296, 1969.

Modrow et al., "Computer-Assisted Analysis of Envelope Protein Sequences of Seven Human Immunodeficiency Virus Isolates: Prediction of Antigenic Epitopes in Conserved and Variable Regions," J. Virol. 61:570-578, 1987.

O'Neil et al., "Identification of Novel Peptide Antagonists for GPIIb/IIIa from a Conformationally Constrained Phage Peptide Library," Proteins 14:509-515, 1992.

Parkes et al., "High Efficiency Transfection of Porcine Vascular Cells in vitro with a Synthetic Vector System," J. Gene Med. 4:292-299, 2002.

Pasqualini et al., "A Peptide Isolated from Phage Display Libraries is a Structural and Functional Mimic of an RGD-Binding Site on Integrins," J. Cell Biology 130:1189-1196, 1995.

Reimer et al., "Analysis of Cationic Liposome-Mediated Interactions of Plasmid DNA with Murine and Human Melanoma Cells in vitro," J. Biol. Chem. 272:19480-19487, 1997.

Unanue et al., "The Basis for the Immunoregulatory Role of Macrophages and Other Accessory Cells," Science 236:551-557, 1987.

* cited by examiner

MATERIALS FOR THE DELIVERY OF BIOLOGICALLY-ACTIVE MATERIAL TO CELLS

This application claims priority from U.S. Provisional Patent Application No. 60/576,270, filed Jun. 2, 2004, and is a continuation in part of PCT International Application No. PCT/GB03/01985, filed on May 8, 2003, which claims priority from United Kingdom Application No. 0210538.5, filed on May 8, 2002. The contents of each of the aforementioned applications are incorporated herein by reference.

FIELD OF THE INVENTION

The present invention relates to lipids suitable for delivery of a biologically-active material, for example nucleic acids, proteins and small molecules, to a cell. The invention also relates to peptides having characteristic spacer groups. The invention further relates to the use of such lipids in combination with such peptides, for example in prophylaxis, treatment and vaccination.

BACKGROUND TO THE INVENTION

Gene delivery for therapy or other purposes is of course well-known, particularly for the treatment of diseases such as cystic fibrosis and certain cancers. The term refers to the delivery into a cell of a gene or part of a gene to correct some deficiency. In the present specification the term is used also to refer to any introduction of nucleic acid material into target cells, and includes gene vaccination and the in vitro production of commercially-useful proteins in so-called cell factories.

Cell delivery systems fall into three broad classes, namely those that involve direct injection of naked DNA, those that make use of viruses or alternated viruses and those that make use of non-viral delivery agents. Each has its advantages and disadvantages. Although viruses as delivery agents have the advantages of high efficiency and high cell selectivity, they have the disadvantages of toxicity, production of inflammatory responses and difficulty in dealing with large DNA fragments. The present invention, in making use of lipids, can overcome these problems.

Non-viral gene delivery systems are based on the compaction of genetic material into nanometric particles by electrostatic interaction between the negatively charged phosphate backbone of DNA and cationic lipids, peptides or other polymers (Erbacher, P. et al, *Gene Therapy*, 1999, 6, 138-145). Various mechanisms for the action of these species have been suggested. An early suggestion was that membrane fusion between liposome and cell membrane occurs. More recently, endocytosis of intact complexes has been proposed. Complexes formed between the nucleic acid and the lipid become attached to the cell surface, and then enter by endocytosis. They then remain localised within a vesicle or endosome for some time and the nucleic acid component is then released into the cytoplasm. Migration of the nucleic acid into the nucleus may then occur some time later, where a gene encoded by the nucleic acid may be expressed. Gene expression in the nucleic involves decoding DNA into RNA and then the protein.

The use of lipids, rather than viruses, for this purpose can result in lower toxicity, reduced cost, reasonably efficient targeting, and the ability to deal with large fragments of nucleic acid material. Unfortunately, lower transfection efficiencies have been noted.

Known complexes include LD complexes comprising DNA condensed with cationic lipids. The DNA is protected from degradation by endogenous nucleases or immune reaction, as well as lysosomal degradation, and can be internalised by endocytosis. Complexes of these cytofectins with DNA need to have an overall positive charge in order to transfect cells as well as avoid aggregation. However, these complexes cannot target specific cells and can have undesirable interactions with the plethora of anionic particles found in extracellular fluids of higher organisms.

Complexes can also be formed between targeting peptides that target cell surface receptors, such as integrin-targeting (I-) peptides, and DNA. When such complexes comprise I-peptides they are called ID complexes. These complexes can be designed to be cell specific and have transfection efficiencies similar to LD complexes. However ID complexes are susceptible to endosomal degradation due to their nature.

A preferred complex is a "LID complex". As used herein, the term "LID complex" represents a complex comprising a lipid, an integrin- (or other receptor-) binding peptide and DNA. These complexes combine the advantages of both LD and ID complexes. LID complexes achieve transfection via an integrin-mediated pathway; they do not necessarily need to have an overall positive charge so undesirable serum interaction can be reduced. The lipid component shields both DNA and, to a degree, the peptide component from degradation, endosomal or otherwise. The peptide component can be designed to be more or less integrin-specific thus conferring a given degree of cell specificity to the LID complex itself. Specificity results from the targeting of the integrin, and transfection efficiencies comparable to some adenoviral vectors can be achieved (Hart et al., Hum. Gene Ther. 9, 1037-47, 1998; Harbottle et al. Hum. Gene. Ther. 9, 575-85, 1998; and Jenkins et al. Gene Therapy 7. 393-400, 2000, the disclosures of which are incorporated herein by reference).

The components of a LID complex associate electrostatically to form a Lipid/Peptide vector complex (Hart et al., *Lipid-mediated enhancement of transfection by a nonviral integrin-targeting vector*, Hum Gene Ther 1998, 9, 575-85; Meng et al., *Efficient transfection of non-proliferating human airway epithelial cells* with a synthetic vector system, J Gene Med 2004, 6, 210-21; Parkes et al., High efficiency transfection of porcine vascular cells in vitro with a synthetic vector system, J Gene Med 2002 4, 292-9). A LID complex is thus a lipopolyplex type of vector. Lipid/peptide vectors transfect a range of cell lines and primary cell cultures with high efficiency epithelial cells (40% efficiency), vascular smooth muscle cells (50% efficiency), endothelial cells (30% efficiency) and haematopoietic cells (10% efficiency), and low toxicity. Furthermore, in vivo transfection of bronchial epithelium of mouse has been demonstrated (Jenkins et al., *Formation of LID vector complexes in water alters physicochemical properties and enhances pulmonary gene expression in vivo*, Gene Therapy 2003, 10, 1026-34), rat lung (Jenkins et al., *An integrin-targeted non-viral vector for pulmonary gene therapy*, Gene Therapy 2000, 7, 393-400) and pig lung (Cunningham et al., *Evaluation of a porcine model for pulmonary gene transfer using a novel synthetic vector*, J Gene Med 2002, 4, 438-46) and with efficiency comparable to that of an adenoviral vector (Jenkins et al., 2000, as above).

An I-peptide for use in such LID complexes must have two functionalities: a "head group" containing an integrin recognition sequence and a "tail" that can bind DNA non-covalently. These two components must also be covalently linked in a way that does not interfere with their individual functions. This is the role of the spacer.

A known I-peptide is peptide 6, in which glycine-alanine is the spacer:

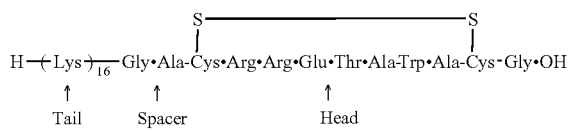

Turning now to the lipid component of the LID complexes, cationic lipids for such a use were developed by Felgner in the late 1980s, and reported in Proc. Natl. Acad. Sci. USA 84, 7413-7417. 1987. A patent to Felgner et al. that may be referred to is U.S. Pat. No. 5,264,618. The disclosure of each of these documents is incorporated herein by reference. Felgner developed the now commercially-available cationic liposome known by the trade mark "Lipofectin" which consists of the cytofectin, DOTMA and the neutral lipid DOPE in a 1:1 ratio. Various other cationic liposome formulations have since been devised, most of which combine a synthetic cationic cytofectin and a neutral lipid. However, cationic vector systems vary enormously in their transfection efficiencies in the presence of serum, which clearly impacts on their potential uses for in vivo gene therapy.

SUMMARY OF THE INVENTION

We have considered the factors that affect transfection, including phase transition temperatures, lipid chain length, the presence or absence of unsaturation in the lipid, the size of the lipid head group, and the charge on the lipid. From these considerations we have designed new lipids that can improve transfection efficiencies. The nucleic acid must be delivered in a form in which it will be taken up, or internalised, by the target cell and allow it to be expressed properly. Also, the nucleic acid must, in general, be protected against certain cellular enzymes such as nucleases, and for in vivo applications have suitable stability to serum. Thus, one must consider both internalization and protection when designing a lipid vector.

More especially, we have found that cationic lipids in a lipid/peptide transfection formulation mediate efficient transfection that is enhanced in the presence of serum compared to formulations containing lipids. In one embodiment, lipids comprising one or more polyethylene glycol (PEG) groups (i.e. PEGylated lipids) showed benefits over lipids which did not comprise PEG groups (i.e. non-PEGylated lipids). In addition, a class of peptides has been identified which improve transfection. In particular, peptides having a spacer group comprising one or more PEG groups show a beneficial effect on transfection efficiency.

According to the invention there is provided a lipid of general formula (I) or (II):

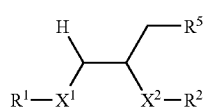

(I)

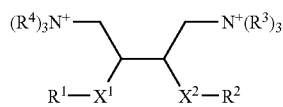

(II)

wherein:
$X^1$ and $X^2$ are the same or different and are selected from the group consisting of —O— and —O—C(O)—;
$R^1$ and $R^2$ are the same or different and are straight or branched, saturated or unsaturated $C_7$ to $C_{24}$ hydrocarbyl groups which are unsubstituted or substituted by one or more substituents selected from the group consisting of hydroxy, halogen and OR', wherein R' is a $C_1$ to $C_6$ hydrocarbyl group;
$R^5$ is —$N^+(R^3)_2$—$R^6$;
$R^6$ is either:
  (a) -[A-Y]$_n$R$^4$ wherein:
    each Y is the same or different and is —$N^+(R^4)_2$—;
    each A is the same or different and is a $C_{1-20}$ alkylene group which is unsubstituted or substituted by one or more substituents selected from the group consisting of hydroxy, halogen, —OR', —C(O)OH, —CN, —NR'R", and —C(O)R' wherein R' and R" are the same or different and are $C_{1-6}$ hydrocarbyl; and
    n is an integer of from 1 to 10; or
  (b) —[B—O]$_m$B-Q wherein:
    each B is the same or different and is a $C_{1-10}$ alkylene group which is unsubstituted or substituted by one or more substituents selected from the group consisting of hydroxy, halogen, —OR', —C(O)OH, —CN, —NR'R" and —C(O)R' wherein R' and R" are the same or different and are $C_{1-6}$ hydrocarbyl;
    m is an integer of from 1 to 10; and
    Q is selected from the group consisting of —$N^+(R^3)_3$, —OH, —OR', —OC(O)R' and halogen wherein R' is as defined above; and
  each $R^3$ and each $R^4$ is the same or different and is a straight or branched, saturated or unsaturated $C_1$ to $C_{10}$ hydrocarbyl group which is unsubstituted or substituted by one or more substituents selected from the group consisting of hydroxy, halogen, —OR', —C(O)OH, —CN, —NR'R ", and —C(O)R' wherein R' and R" are the same or different and are $C_1$ to $C_6$ hydrocarbyl.

The invention further provides a lipid of general formula (III):

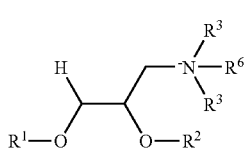

(III)

wherein:
$R^1$ and $R^2$ are the same or different and are straight or branched, saturated or unsaturated $C_{12-20}$ as hydrocarbyl groups which are unsubstituted or substituted by one or more substituents selected from the group consisting of hydroxy, halogen and —OR' wherein R' is a $C_{1-6}$ hydrocarbyl group;
each $R^3$ is the same or different and is a straight or branched, saturated or unsaturated $C_{1-6}$ hydrocarbyl group which is unsubstituted or substituted by one or more substituents selected from hydroxy, halogen, —OR', —COOH, —CN, —NR'R" and —COR' wherein R' and R" are the same or different and are $C_{1-4}$ hydrocarbyl;
$R^6$ is —[B—O]$_m$B-Q wherein each B is the same or different and is a $C_{1-6}$ alkylene group which is unsubstituted or substituted by one or more substituents selected from the group consisting of hydroxy, halogen, —OR', —C(O) OH, —CN, —NR'R" and —C(O)R' wherein R' and R" are the same or different and are $C_{1-4}$ hydrocarbyl; m is an integer of from 1 to 8; and Q is selected from the group consisting of —$N^+(R^3)_3$, —OH, —OR', —OC(O) R' and halogen, wherein R' is as defined above.

In a further embodiment of the invention there is provided a lipid of formula (IV):

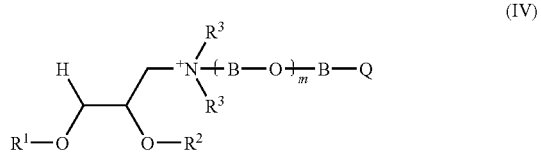

(IV)

wherein

R$^1$ and R$^2$ are the same or different and are selected from the group consisting of $C_{12-20}$ alkylene groups and $C_{12}$-$C_{20}$ alkenylene groups;

each R$^3$ is the same or different and is selected from unsubstituted $C_{1-4}$ alkyl groups;

each B is the same or different and is a $C_{1-6}$ alkylene group which is unsubstituted or substituted by one or more substituents selected from hydroxy, halogen, —OR', —C(O)OH, —CN, —NR'R" and —C(O)R' wherein R' and R" are the same or different and are $C_{1-4}$ hydrocarbyl;

m is an integer from 3 to 8; and

Q is selected from the group consisting of —$N^+(R^3)_3$, —OH, and —OR' wherein R' is an unsubstituted $C_{1-4}$ alkyl group.

In another aspect of the invention there is provided a complex suitable for delivery of a biologically-active material to a cell, which complex comprises a lipid as defined according to any of the formulae above, and a biologically-active material such as a nucleic acid, peptide or small molecule. In a preferred embodiment the complex further comprises an integrin-binding peptide. A complex of the invention may therefore be a LID complex comprising a lipid as described above, an integrin-binding peptide and DNA.

A complex of the invention can be prepared by a process which comprises the step of admixing (i) a lipid of the invention and (ii) a biologically-active material. An integrin-binding peptide can be mixed with the lipid and the biologically active material. A LID complex can thus be formed.

A cell can be transfected in vivo, in vitro or ex vivo with a biologically-active material by means of a complex of the invention. A nucleic acid can thus be delivered to and expressed in a cell by transfecting the cell with a complex of the invention under conditions to provide for expression of the nucleic acid component of the complex. A polypeptide can be produced by a method which comprises:

(a) transfecting a cell with a complex of the invention under conditions to provide for expression of the polypeptide encoded by the nucleic acid component of the complex; and (b) recovering the expressed polypeptide;

A pharmaceutical composition can thus comprise a complex of the invention and a pharmaceutically-acceptable carrier, diluent or excipient. A complex of the invention can be used in a method of prophylaxis or treatment of the human or animal body by therapy. A complex of the invention can therefore be employed in the prophylaxis or treatment of a condition caused by or related to a genetic defect or modification. For that purpose, the biologically-active material within the complex may be an anti-sense nucleic acid or an iRNA. A complex of the invention can be used for vaccinating a human or animal. An immune response against a desired antigen/pathogen can thus be raised in a mammalian host.

DETAILED DESCRIPTION OF THE INVENTION

Figure 1:
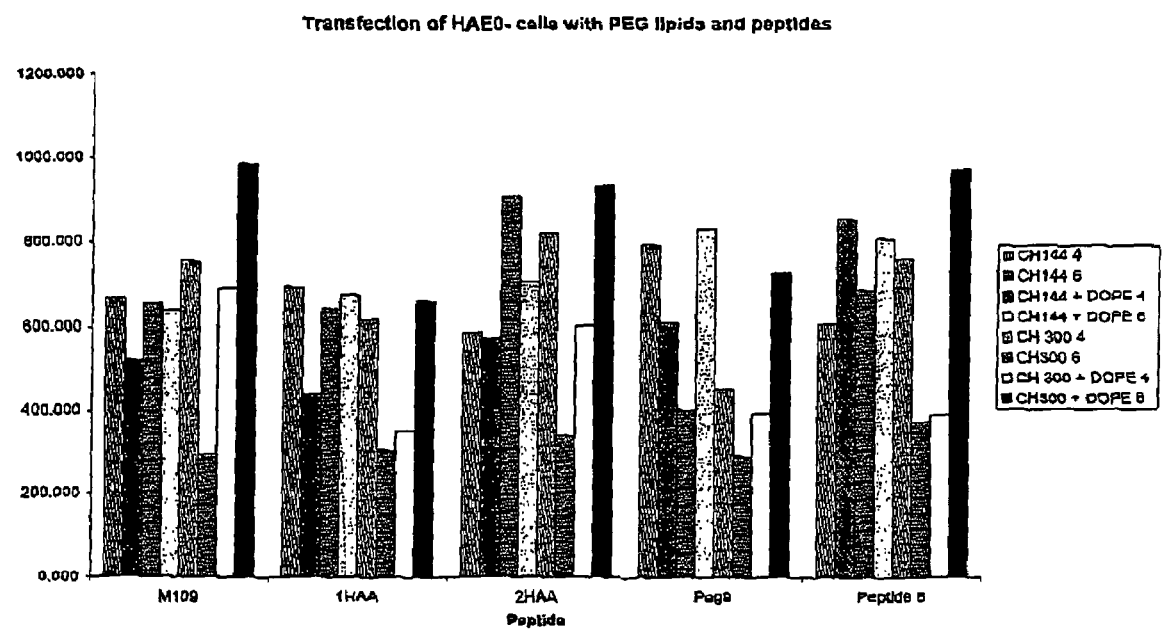
FIG. 1 discloses transfection data for IHAEo-cells using different combinations of ligand and peptide.

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

The invention relates to materials suitable for the delivery of a biologically-active material to a cell. These materials include lipids, and also complexes are based on these lipids. The complexes of the invention may be used, for example, in gene therapy and vaccination. Gene therapy may be carried out, for example, to correct a genetic defect of modification. The invention also relates to peptides for use in these complexes.

For the avoidance of doubt, in the general formulae (I) and (II) set out above, the orientation of the $X^1$ and $X^2$ moieties is such that the right hand side of the depicted moieties are attached to the group $R^1$ or $R^2$ respectively.

As used herein, a $C_{1-24}$ alkyl group or moiety is a linear or branched alkyl group or moiety containing from 1 to 24 carbon atoms such as a $C_{1-6}$ alkyl group or moiety, a $C_{1-10}$ alkyl group or moiety, or a $C_{7-24}$ alkyl group or moiety. Examples of $C_{1-6}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, an alkylene group is a divalent alkyl group, wherein the alkyl group is as defined above. For example a $C_1$ alkylene group (i.e. methylene) is a divalent $C_1$ alkyl group, i.e. —$CH_2$—. Where the alkylene group comprises 2 or more carbon atoms, the group may be branched, e.g. an ethylene group may be —$CH_2CH_2$— or —$CH(CH_3)$—.

As used herein, a $C_{2-24}$ alkenyl group or moiety is a linear or branched alkenyl group or moiety containing from 2 to 24 carbon atoms such as a $C_{2-6}$ alkenyl group or moiety, a $C_{2-10}$ alkenyl group or moiety, or a $C_{7-24}$ alkenyl group or moiety. The alkenyl group may contain one or more carbon-carbon double bonds, for example, one, two or three double bonds, each of which may be cis or trans. Preferred alkenyl groups contain one or two double bonds, more preferably one double bond. Preferably the double bond or bonds are in the cis configuration. For the avoidance of doubt, where two alkenyl or two alkynyl moieties are present in a group, the alkenyl or alkynyl moieties may be the same or different. Typically the alkenyl groups are unsubstituted.

The alkyl groups may be unsubstituted or substituted by one or more substituents selected from hydroxy, halogen and —OR' wherein R' is a $C_{1-6}$ alkyl or $C_{2-6}$ alkenyl group one or more substituents selected from hydroxy, halogen, —OR', —COOH, —CN, —NR'R" and —COR" wherein each R' and R" is the same or different and is a $C_{1-6}$ alkyl or $C_{2-6}$ alkenyl group.

According to a first embodiment of the invention $X^1$ and $X^2$ are typically the same. Preferably both $X^1$ and $X^2$ are —O—. One or both of $X^1$ and $X^2$ can represent the group —O—$CH_2$—. In this case it is preferred that $X^1$ and $X^2$ are both —O—$CH_2$—.

Examples of unsaturated hydrocarbyl groups include alkenyl groups and alkynyl groups. Preferred unsaturated hydrocarbyl groups are alkenyl groups which contain one or more, for example one or two, double bonds, each of which may be cis or trans. Typically, unsaturated hydrocarbyl groups are alkenyl groups which contain one or two cis double bonds. Typically, a said hydrocarbyl group is unsubstituted.

In the first embodiment of the invention typically, each R' and R" is the same or different and is a $C_1$ to $C_6$ alkyl group.

In the first embodiment of the invention preferably, $R^1$ and $R^2$ are the same or different and are straight or branched, saturated or unsaturated $C_{10}$ to $C_{22}$ hydrocarbyl groups which are unsubstituted or substituted as defined above. More preferably, $R^1$ and $R^2$ are the same or different and are straight or branched, saturated or unsaturated $C_{12}$ to $C_{20}$ hydrocarbyl groups which are unsubstituted or substituted as defined above. More preferably still, $R^1$ and $R^2$ are the same or different and are straight or branched, saturated or unsaturated $C_{16}$ to $C_{18}$ hydrocarbyl groups which are unsubstituted or substituted as defined above. Most preferably, $R^1$ and $R^2$ are the same or different and represent a palmitic, stearic, oleic, linoleic or linolenic residue. In one aspect of this embodiment it is preferred that $R^1$ and $R^2$ are oleic residues [e.g. —$(CH_2)_7$CH=CH$(CH_2)_7CH_3$.]. In another aspect of this embodiment it is preferred that $R^1$ and $R^2$ are monounsaturated $C_{16}$ groups [e.g. —$(CH_2)_{10}$CH=CH$(CH_2)_3CH_3$].

According to this embodiment typically, $R^1$ and $R^2$ are the same. Typically, $R^1$ and $R^2$ are unsubstituted or carry one, two or three substituents. Preferably, $R^1$ and $R^2$ are unsubstituted.

According to this embodiment typically, each $R^3$ and each $R^4$ is unsubstituted or substituted by one or more, for example one or two, substituents selected from hydroxy, —OR', —C(O)OH, —CN, —NR'R" and —C(O)R' wherein R' and R" are the same or different and are $C_1$ to $C_6$ hydrocarbyl.

According to this embodiment, preferably each $R^3$ and each $R^4$ are the same or different and are straight or branched, saturated or unsaturated $C_1$ to $C_6$ hydrocarbyl groups, for example $C_1$ to $C_4$ hydrocarbyl groups, which are unsubstituted or substituted by one or more substituents as defined above. Typically each $R^3$ is the same. Typically each $R^4$ is the same. Preferably each $R^3$ and each $R^4$ are the same.

According to this embodiment typically $R^3$ and $R^4$ are $C_1$-$C_{10}$ alkyl groups, for example $C_1$-$C_6$ and $C_1$-$C_4$ alkyl groups. Preferably, $R^3$ and $R^4$ are methyl.

According to this embodiment $R^3$ and $R^4$ are typically unsubstituted or carry one or two substituents. Preferred $R^3$ and $R^4$ substituents are selected from hydroxy and —OR' wherein R' is a $C_1$ to $C_6$ alkyl group. More preferably, $R^3$ and $R^4$ are unsubstituted.

According to this embodiment preferably n is from 1 to 5. More preferably, n is from 1 to 2. Typically, n is 1.

According to this embodiment preferably m is from 1 to 5. More preferably, m is from 1 to 3. Typically, m is 1 or 2.

According to this embodiment preferably A is $C_1$ to $C_{10}$ alkylene, for example $C_3$, $C_6$ or $C_{10}$ alkylene, which is unsubstituted or substituted by one or more substituents as defined above. More preferably, A is $C_2$ to $C_6$ alkylene which is unsubstituted or substituted by one or more substituents as defined above. Yet more preferably, A is $C_3$, $C_4$ or $C_5$ alkylene which is unsubstituted or substituted by one or more substituents as defined above. Most preferably, A is propylene which is unsubstituted or substituted by one or more substituents as defined above.

According to this embodiment typically A is unsubstituted or carries one or two substituents. Preferred substituents for A are selected from hydroxy, halogen and —OR' wherein R' is a $C_1$ to $C_6$ alkyl group. More preferably, A is unsubstituted.

According to this embodiment preferably B is $C_1$ to $C_5$ alkylene which is unsubstituted or substituted by one or more substituents as defined above. More preferably, B is $C_2$, $C_3$ or $C_4$ alkylene which is unsubstituted or substituted by one or more substituents as defined above. Most preferably, B is ethylene which is unsubstituted or substituted by one or more substituents as defined above.

According to this embodiment typically B is unsubstituted or carries one or two substituents. Preferred substituents for B are selected from hydroxy, halogen and —OR' wherein R' is a $C_1$ to $C_6$ alkyl group. More preferably, B is unsubstituted.

According to this embodiment Q is preferably —$N^+(R^3)_3$ or OH. Typically, Q is —$N^+Me_3$ or OH.

In a second embodiment of the invention it is preferred that, in the lipid of formula (I) or (II), $R^1$ and $R^2$ are the same or different and represent a $C_{12-20}$ hydrocarbyl group, preferably a $C_{14-20}$ hydrocarbyl group. In the lipids of formula (I) and (II), $R^1$ and $R^2$ are preferably the same or different and represent a $C_{14}$, $C_{16}$, $C_{18}$ or $C_{20}$ hydrocarbyl group, more preferably a $C_{16}$, $C_{18}$ or $C_{20}$ hydrocarbyl group. Such hydrocarbyl groups may be branched or straight-chain alkyl groups, or may be branched or straight-chain alkenyl groups. The alkenyl groups may contain one or more double bonds, for example one, two or three double bonds. When $R^1$ and/or $R^2$ is an alkenyl group it is preferred that they contain one or two double bonds, more preferably one double bond.

In this second embodiment of the invention it is particularly preferred that $R^1$ and $R^2$ are both $C_{16}$ or $C_{18}$ alkenyl groups having one double bond. In one aspect of this embodiment it is preferred that $R^1$ and $R^2$ are both monounsaturated $C_{18}$ groups, e.g. —$(CH_2)_7$CH=CH$(CH_2)_7CH_3$. In another aspect of this embodiment it is preferred that $R^1$ and $R^2$ are both monounsaturated $C_{16}$ groups, e.g. —$(CH_2)_{10}$CH=CH$(CH_2)_3CH_3$.

In this second embodiment of the invention it is preferred, in the lipids of formula (I) and (II), that $R^5$ is —$N^+(R^3)_2$—$R^6$ and $R^6$ is —[B—O]$_m$B-Q wherein:

each B is the same or different and is a $C_{1-6}$ alkylene group which is unsubstituted or substituted by one or more substituents selected from hydroxy, halogen, —OR', —C(O)OH, —CN, —NR'R" and —C(O)R' wherein R' and R" are the same or different and are $C_{1-4}$ hydrocarbyl;

m is from 1 to 8; and

Q is selected from —$N^+(R^3)_3$, —OH and —OR', wherein R' is a $C_{1-4}$ alkyl group.

In a third embodiment of the invention the lipids are defined by formula (III) above. In the third embodiment, the preferred $R^1$, $R^2$, $R^3$ and $R^6$ groups are as defined earlier in either the first or the second embodiments.

In a fourth embodiment of the invention, the lipids are defined by formula (IV). It is preferred that $R^1$ and $R^2$ are both $C_{12-20}$ alkenylene groups having one double bond each. In particular it is preferred that $R^1$ and $R^2$ are both $C_{16}$ or $C_{18}$ alkenylene groups having one double bond each, for example —$(CH_2)_7$CH=CH$(CH_2)_7CH_3$ or —$(CH_2)_{10}$CH=CH$(CH_2)_3CH_3$ In the fourth embodiment it is preferred that each $R^3$ group is a methyl or ethyl group, preferably a methyl group. It is also preferred that each B is the same or different and is an unsubstituted $C_{1-3}$ alkylene group, such that short-chain alkylene glycol units can be formed. For example, in one embodiment it is preferred that each B is —$CH_2CH_2$—.

The number of alkylene glycol units may vary. The most preferred value of m is 3. However, the value may vary, for example m may be 4, 5, 6 or 7, with m is 5 being a preferred value. It is preferred that Q is —OH or —OR' wherein R' is an unsubstituted $C_{1-4}$ alkyl group.

In the fourth embodiment particularly preferred lipids include {2,3-di-[(Z)-octadec-9-enyloxy]-propyl}-N-(2-{2-[2-(2-hydroxy-ethoxy)-ethoxy]-ethoxy}-ethyl)-N,N-dimethylammonium bromide, {2,3-di-[(Z)-ocatadec-9-enyloxy]-propyl}-N-{2-[2-(2-{2-[2-(2-hydroxy-ethoxy)-ethoxy]-ethoxy}-ethoxy)-ethoxy]-ethyl}-N,N-dimethylammonium bromide, {2,3-di-[(Z)-hexadec-11-enyloxy]-propyl}-N-(2-{2-[2-(2-hydroxy-ethoxy)-ethoxy]-ethoxy}-ethyl)-N,N-dimethylammonium bromide and {2,3-di-[(Z)-hexadec-11-enyloxy]-propyl}-N-{2-[2-(2-{2-[2-(2-hydroxy-ethoxy)-ethoxy]-ethoxy}-ethoxy)-ethoxy]-ethyl}-N,N-dimethylammonium bromide.

In a fifth embodiment of the invention there is provided a lipid of general formula (I):

wherein
$X^1$ and $X^2$ are the same or different and are selected from —O— and —O—C(O)—;
$R^1$ and $R^2$ are the same or different and are selected from $C_{7-24}$ alkyl and $C_{7-24}$ alkenyl groups which are unsubstituted or substituted by one or more substituents selected from hydroxy, halogen and —OR' wherein R' is a $C_{1-5}$ alkyl or $C_{2-6}$ alkenyl group;
$R^5$ is —$N^+(R^3)_2R^6$;
$R^6$ is either:
(a) -[A-Y]$_n$$R^4$ wherein:
each Y is the same or different and is —$N^+(R^4)_2$—;
each A is the same or different and is a $C_{1-20}$ alkylene group which is unsubstituted or substituted by one or more substituents selected from hydroxy, halogen, —OR', —C(O)OH, —CN, —NR'R", and —C(O)R' wherein R' and R" are the same or different and are $C_{1-6}$ hydrocarbyl; and
n is from 1 to 10; or
(b) —[B—O]$_m$B-Q wherein:
each B is the same or different and is a $C_{1-10}$ alkylene group which is unsubstituted or substituted by one or more substituents selected from hydroxy, halogen, —OR', —C(O)OH, —CN, —NR'R" and —C(O)R' wherein R' and R" are the same or different and are $C_{1-6}$ hydrocarbyl;
m is from 1 to 10; and
Q is selected from —$N^+(R^3)_3$, —OH, —OR', —OC(O)R' and halogen, wherein R' is as defined above; and
each $R^3$ and $R^4$ is the same or different and is selected from $C_{1-10}$ alkyl and $C_{2-10}$ alkenyl groups which are unsubstituted or substituted by one or more substituents selected from hydroxy, halogen, —OR', —COOH, —CN, —NR'R" and —COR" wherein each R' and R" is the same or different and is a $C_{1-6}$ alkyl or $C_{2-6}$ alkenyl group.

In an alternative embodiment to that disclosed above $X^1$ and $X^2$ are the same or different and are selected from —O—$CH_2$— and —O—C(O)—.

In the fifth embodiment described above it is preferred that $R^1$ and $R^2$ are the same or different and represent a $C_{12-20}$ alkyl or $C_{12-20}$ alkenyl group, preferably a $C_{14-20}$ alkyl or $C_{14-20}$ alkenyl group. In the lipids of formula (I), $R^1$ and $R^2$ are preferably the same or different and represent a $C_{14}$, $C_{16}$, $C_{18}$ or $C_{20}$ alkyl or alkenyl group, more preferably a $C_{16}$, $C_{18}$ or $C_{20}$ alkyl or alkenyl group. Such alkyl or alkenyl groups may be branched or straight-chain. Preferably $R^1$ and $R^2$ are $C_{14-20}$ alkenyl groups containing one or more double bonds, for example one, two or three double bonds. When $R^1$ and/or $R^2$ is an alkenyl group it is preferred that they contain one or two double bonds, more preferably one double bond. Particularly preferred alkenyl groups include $C_{16}$ and $C_{18}$ alkenyl groups such as those described above in relation to other embodiments.

In this fifth embodiment of the invention it is preferred, in the lipids of formula (I), that $R^5$ is —$N^+(R^3)_2$—$R^6$ and $R^6$ is —[B—O]$_m$B-Q, wherein:
each B is the same or different and is a $C_{1-6}$ alkylene group which is unsubstituted or substituted by one or more substituents selected from hydroxy, halogen, —OR', —C(O)OH, —CN, —NR'R" and —C(O)R' wherein R' and R" are the same or different and are $C_{1-4}$ hydrocarbyl;
m is from 1 to 8; and
Q is selected from —$N^+(R^3)_3$, —OH and —OR', wherein R' is a $C_{1-4}$ alkyl group.

More preferably each B is the same or different and is an unsubstituted $C_{1-4}$ alkylene group. More preferably each B is an unsubstituted $C_2$ alkylene group, —$CH_2CH_2$—. It is preferred that each $R^3$ is the same or different and is a $C_{1-4}$ alkyl group, more preferably a $C_{1-2}$ alkyl group and most preferably a methyl group. The integer m is preferably 3, 4, 5, 6, 7 or 8, for example m=3 or m=5. Q is most preferably —OH or —OR' where R' is a $C_{1-4}$ alkyl group, with —OH being most preferred.

The present invention also provides a composition including the structure (V):

wherein:
the Rs, which may be the same or different, are
(a) H,
(b) —$CH_2$—$N^+(R^2)_2$—$CH_2$—$CH_2$—[Y—$(CH_2)_p$—]$_q$-Z, or
(c) —$CH_2$—$N^+(R^4)_3$,
with the proviso that one R is H and the other is group (b); or both groups R are groups (c); and wherein
the Xs which may be the same or different, are —O— or —O—C(O)—;
the $R^1$s, which may be the same or different, are saturated or unsaturated $C_7$ to $C_{23}$ chains;
the $R^2$s, which may be the same or different, are $C_1$ to $C_6$ saturated or unsaturated chains;

Y in $NH$, $CH_2$, O or N(acetyl);

Z is —$O(C_1$ to $C_4$ alkyl), —$OC(O)R^3$, —$N^+R_3^4$, —OH, —F, —Cl, —Br or —I where $R^3$ is $C_1$ to $C_6$ alkyl;

the $R^4$s, which may be the same or different, are $C_1$ to $C_6$ chains;

n is from 2, 3 or 4; and m is from 1 to 200 and where it is at least 2 the resulting repeating units may be the same or different.

In formula (V), we prefer that one R is hydrogen and the other is group (b). In this case the lipid may be PEG-based.

Typically, m is less than or equal to 100, more preferably less than of equal to 50, especially less than or equal to 25, more especially less than or equal to 12. Preferably m is at least 2. When Y is $CH_2$, preferably Z is not OH and preferably not —$O(C_1$-$C_4$ alkyl).

Since formula (V) set out above is cationic, it will be accompanied by one or more appropriate non-toxic anions. Suitable anions include halide, particularly iodide.

Where the groups X in the formula (V) are —$OCH_2$—, the linkages will of course be ethers, and where the groups are —O—C(O)— the linkages will be esters. The ether structures are preferred because they seem to have greater activity.

The chain length of the tails $R^1$ in the formula (V) has been investigated. Including the carbon atom of the linkage X, we prefer from $C_{10}$ to $C_{22}$, and preferably straight-chain. At present a value of about $C_{16}$ or $C_{18}$ seems to be optimum, although the precise value will depend on the application. Other possible values include $C_{12}$, $C_{14}$, and $C_{20}$.

The tails may be saturated or unsaturated, and when unsaturated may contain one or more double bonds, each of which may be cis or trans, and/or one or more triple bonds. Typical unsaturated structures include one or two cis double bonds. We have found higher transfection efficiencies with unsaturated lipids.

Groups $R^2$ in the formula (V) are preferably straight chain alkyl, although branched groups can be acceptable. We prefer $C_1$, $C_2$, $C_3$ and $C_4$ alkyl. The same applies to group $R^3$.

Although (when m is two or more) the repeating units [Y—$(CH_2)$—] in the formula (V) may all be the same, we prefer that Y be $CH_2$ in all but one of them, and therefore that it take on one of the other possibilities in only one of the repeating units. Of these other possibilities, O is preferred. The number of methylene groups, n, is preferably 2, although other values for sample 1, 3, 4, 5 and 6 may be desirable in some circumstances.

The lipids of formulae (I), (II), (III), (IV) and (V) are, of course, cationic, and will be associated with one or more pharmaceutically acceptable anion. Examples of acceptable anions include anions of various mineral acids such as, for example, chloride, bromide, iodide, sulfate, nitrate, phosphate and anions of organic acids such as, for example, acetate, trifluoroacetate, maleate, fumarate, citrate, oxalate, succinate, tartrate, malate, mandelate, methanesulfonate and p-toluenesulfonate. Prefereed anions are chloride, bromide, iodide, sulphate, nitrate, acetate, maleate, oxalate and succinate. More preferred anions are bromide and iodide.

Examples of unsaturated hydrocarbyl groups include alkenyl groups and alkynyl groups. Preferred unsaturated hydrocarbyl groups are alkenyl groups which contain one or more, for example one or two, double bonds, each of which may be cis or tans. Typically, unsaturated hydrocarbyl groups are alkenyl groups which contain one or two cis double bonds. Typically, a said hydrocarbyl group is unsubstituted.

The lipids of the invention contain one or more chiral centre. For the avoidance of doubt, the chemical structures depicted herein are intended to embrace all stereoisomers of the compounds shown, including racemic and non-racemic mixtures and pure enantiomers and/or diastereoisomers.

The lipids of the invention may be formulated with one or more other components as complexes which are suitable for use in the delivery of a biologically-active material to a cell. Typically, such complexes comprise a lipid of the invention and a biologically-active material. Complexes of the invention may also comprise one or more of: an integrin-binding peptide; a polycationic component; and a neutral lipid.

Suitable biologically-active materials include nucleic acids, peptides and polypeptides, and small molecules. A biologically-active material is one which has a biological effect when introduced into a cell or host, for example by stimulating an immune response or an inflammatory response, by exerting enzymatic activity or by complementing a mutation, etc. These particular biological activities are given merely by way of examples and are not to be taken as limiting.

The terms "nucleic acid" and "polynucleotide" are used interchangeably and refer to a polymeric form of nucleotides of any length, either deoxyribonucleotides or ribonucleotides, or analogs thereof. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, cosmids, vectors, artificial chromosomes, isolated DNA of any sequence, isolated RNA of any sequence, nucleic acid probes, and primers.

Polynucleotides of the invention may include within them synthetic or modified nucleotides. A number of different types of modification to polynucleotides are known in the art. Such modifications may be carried out in order to enhance the in vivo activity, lifespan, nuclease resistance or ability to enter cell. For example, phosphorothioate oligonucleotides may be used. Other deoxynucleotide analogs include methylphosphonates, phosphoramidates, phorphorodithioates, N3'P5'-phosphoramidates and oligoribonucleotide phosphorothioates and their 2'-O-alkyl analogs and 2'-O-methylribonucleotide methylphosphonates.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

A DNA in a complex of the invention may be in the form of a linear molecule or a circular molecule, for example a plasmid or cosmid. Examples of linear DNA molecules include DNA in the form of a chromosome or a mini chromosome.

An RNA used in a complex of the invention may be polycistronic, i.e. may comprise more than one coding sequence, and therefore may comprise an internal ribosome entry site (IRES).

If a DNA for use in the invention comprises more than one DNA coding sequence, those coding sequences may be operably linked to independent control sequences. Alternatively, the coding sequences may be operably linked to common control sequences, in which case the coding sequences may be separated by an (IRES).

An RNA in complex of the invention may be linear or circular, for example a replicon, in particular an alpha virus replicon. The RNA may be single stranded or double stranded. The RNA may be an mRNA. Suitable mRNAs will typically comprise a 5' cap and/or a 3' polyA tail. In addition, the length of the polyA tail may be modulated to regulate the stability of the mRNA within target cells and hence control the duration of transgene expression from the mRNA. Typically, a polyA tail of will be up to about 300 residues in length, preferably from about 50 to about 90 residues in length.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e. g., a DNA sequence for mammals) that occupies a specific physical location (a "gene locus" or "genetic locus") within the genome of an organism. A gene can encode an expressed product, such as a polypeptide or a polynucleotide (e. g., tRNA). Alternatively, a gene may define a genomic location for a particular event/function, such as the binding of proteins and/or nucleic acids (e. g., phage attachment sites), wherein the gene does not encode an expressed product. Typically, a gene comprises coding sequences, such as polypeptide encoding sequences, and non-coding sequences, such as promoter sequences, poly-adenylation sequences, transcriptional regulatory sequences (e. g., enhancer sequences). Many eukaryotic genes have "exons" (coding sequences) interrupted by "introns" (non-coding sequences). In certain cases, a gene may share sequences with another gene (s) (e. g., overlapping genes).

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements").

The boundaries of a coding sequence are determined by a start codon at the 5' (amino) terminus and a translation stop codon at the 3' (carboxy) terminus. A coding sequence can include, but is not limited to, cDNA from viral, eukaryotic or eukaryotic mRNA, genomic DNA sequences from viral or procaryotic DNA, and even synthetic DNA sequences. A transcription termination sequence may be located 3' to the coding sequence. Transcription and translation of coding sequences are typically regulated by "control elements", including, but not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A nucleic acid for use in the invention which comprises a coding sequence may be contained in an expression vector. A suitable expression vector comprises nucleotide sequences, for example a coding sequence encoding a desired peptide or polypeptide. Such expression vectors are routinely constructed in the art of molecular biology and may for example involve the use of plasmid or cosmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. A nucleic acid suitable for use in the invention may also be inserted into a vector in an antisense orientation in order to provide for the production of antisense RNA.

A "promoter" is a nucleotide sequence which initiates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. In addition, such promoters can also have tissue specificity. It is intended that the term "promoter" or "control element" includes full-length promoter regions and functional (e. g., controls transcription or translation) segments of those regions. Thus, a polynucleotide, especially a coding, for use in a complex of the invention is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A control sequence, such as a promoter, "operably linked" to a coding sequence is positioned in such a way that expression of the coding sequence is achieved under conditions compatible with the control sequence. The control sequence will typically comprise a promoter and optionally also comprise other types of control sequences, for example an enhancer and/or terminator. An enhancer is any polynucleotide sequence capable of increasing the level of transcription initiating from a promoter and may act on a cis or trans basis. A terminator is any polynucleotide sequence capable of promoting dissociation of an RNA polymerase from the said sequence.

A control sequence may be positioned 5', 3' or internal to (for example in an intron) a coding sequence. A coding sequence may be operably linked to more than one control sequence, for example two, three, four or five control sequences. Such multiple control sequences may be positioned, for example, entirely 5' to the coding sequence. However, more typically control sequences will be located both 5' and 3' to the coding sequence, with optional internal control sequences.

Control sequences may be derived from any suitable source and may be generated by recombinant techniques or synthetic means.

The vectors may be for example, plasmid, virus or phage vectors provided with a origin of replication, optionally a promoter for the expression of the desired polynucleotide and optionally a regulator of the promoter. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example in a method of gene therapy or vaccination.

Suitable nucleic acids for use in a complex of the invention may be obtained from natural sources, or may be produced recombinantly or by chemical synthesis. They may be modified, for example, to comprise a sequence encoding a specific function, for example, a nuclear localisation sequence.

A nucleic acid in a complex of the invention may be selected for use in gene therapy, in gene vaccination, in antisense therapy or in therapy by interfering RNA. All of these uses may be generally referred to as gene therapy.

As has been set out above, appropriate trascriptional and translational control elements are generally provided. For gene therapy, the nucleic acid component is generally presented in the form of a nucleic acid insert in a plasmid or vector. In some case, however, it is not necessary to incorporate the nucleic acid component in a vector in order to achieve expression. For example, gene vaccination and anti-sense therapy can be achieved using a naked nucleic acid. The nucleic acid is generally DNA but RNA may be used in some cases, for example, in cancer vaccination.

The nucleic acid in a complex of the invention may be or may relate to a gene that is the target for particular gene therapy or may be a molecule that can function as a gene vaccine or as an anti-sense therapeutic agent. The nucleic acid may be or correspond to a complete full-length coding sequence or may be part of a coding sequence.

A nucleic acid may be selected to act via an antisense mechanism or via an RNA interference mechanism (RNAi). An antisense RNA may comprise a polynucleotide which has substantial complementarity to all or part of its target mRNA. A polynucleotide which has substantial sequence complementarity to all or part of its target mRNA is typically one which is capable of hybridizing to that mRNA. If the RNA has substantial complementarity to a part of its target mRNA of, it generally has substantial complementarity to a contiguous set of nucleotides within that mRNA.

There are, generally speaking, two antisense approaches which may be used in the invention.

In one approach, a vector is used which allows for the expression of a polynucleotide which has substantial sequence complementarity to all or part of the target mRNA (i.e. a polynucleotide which can hybridize to that mRNA). This results in the formation of an RNA-RNA duplex which may result in the direct inhibition of translation and/or the destabilization of the target message, by rendering it susceptibility to nucleases, for example. The vector will typically allow the expression of a polynucleotide which hybridizes to the ribosome binding region and/or the coding region of the target mRNA.

Alternatively, an oligonucleotide may be delivered which is capable of hybridizing to the target mRNA. Antisense oligonucleotides are postulated to inhibit target gene expression by interfering with one or more aspects of RNA metabolism, for example processing, translation or metabolic turnover. Chemically modified oligonucleotides may be used and may enhance resistance to nucleases and/or cell permeability.

In the first approach, the vector is capable of expressing a polynucleotide which has substantial sequence complementarity to all of part of the target mRNA. Such a polynucleotide will be capable of hybridizing to the target mRNA. Typically, such a polynucleotide will be an RNA molecule. Such a polynucleotide may hybridize to all or part of the target mRNA. Generally, therefore the polynucleotide will be complementary to all of or part of such an mRNA. For example, the polynucleotide may be the exact complement of such an mRNA. However, absolute complementarity is not required and preferred polynucleotides which have sufficient complementarity (i.e. substantial complementarity) to form a duplex having a melting temperature of greater than 40° C. under physiological conditions are particularly suitable for use in the present invention. The polynucleotide may be a polynucleotide which hybridises to the target mRNA under conditions of medium to high stringency, such as 0.03M sodium chloride and 0.03M sodium citrate at from about 50 to about 60 degrees centigrade.

It is preferred that the polynucleotide hybridizes to a coding region of the target mRNA. However, a polynucleotide may be employed which hybridises to all or part of the 5'- or 3'-untranslated region of such an mRNA. The polynucleotide will typically be at least 40, for example at least 60 or at least 80, nucleotides in length and up to 100, 200, 300, 400, 500, 600 or 700 nucleotides in length or even up to a few nucleotides, such as five or ten nucleotides, shorter than the full-length mRNA.

The polynucleotide, (i.e. the "antisense" polynucleotide), may be expressed in a cell from a suitable vector. A suitable vector is typically a recombinant replicable vector comprising a sequence which, when transcribed, gives rise to the polynucleotide (typically an RNA). Typically, the sequence encoding the polynucleotide is operably linked to a control sequence which is capable of providing for the transcription of the sequence giving rise to the polynucleotide. The term "operably linked" refers to a juxtaposition wherein the components described are in a relationship permitting them to function in their intended manner. A control sequence "operably linked" to a sequence giving rise to an antisense RNA is ligated in such a way that transcription of the sequence is achieved under conditions compatible with the control sequences.

The vectors may be for example, plasmid or virus vectors provided with an origin of replication, optionally a promoter for transcription to occur and optionally a regulator of the promoter. The vectors may contain one or more selectable marker genes, for example an ampicillin resistance gene in the case of bacterial plasmid or a neomycin resistance gene for a mammalian vector. Vectors may be used in vitro, for example for the production of antisense RNA, or used to transfect or transform a host cell. The vector will typically be adapted for use in vivo, for example in a method of gene therapy.

Promoters/enhancers and other expression regulation signals may be selected to be compatible with the host cell for which the expression vector is designed. For example, mammalian promoters, such as β-actin promoters, may be used. Viral promoters may also be used, for example the Moloney murine leukaemia virus long terminal repeat (MMLV LTR), the promoter rous sarcoma virus (RSV) LTR promoter, the SV40 promoter, the human cytomegalovirus (CMV) IE promoter, herpes simplex virus promoters or adenovirus promoters. All these promoters are readily available in the art. Preferred promoters are tissue specific promoters, for example promoters driving expression specifically within vascular tissue.

In the antisense oligonucleotide approach, a suitable oligonucleotide will typically have a sequence such that it will bind to the target mRNA. Therefore, it will typically have a sequence which has substantial complementarity to a part of such an mRNA. A suitable oligonucleotide will typically have substantial complementarity to a contiguous set of nucleotides within the target mRNA. An antisense oligonucleotide will generally be from about 6 to about 40 nucleotides in length. Preferably it will be from 12 to 20 nucleotides in length.

Generally the oligonucleotide used will have a sequence that is absolutely complementary to the sequence. However, absolute complementarity may not be required and in general any oligonucleotide having sufficient complementarity (i.e. substantial complementarity) to form a stable duplex (or triple helix as the case may be) with the target nucleic acid is considered to be suitable. The stability of a duplex (or triplex) will depend inter alia on the sequence and length of the hybridizing oligonucleotide and the degree of complementarity between the antisense oligonucleotide and the target sequence. The system can tolerate less complementarity when longer oligonucleotides are used. However oligonucleotides, especially oligonucleotides of from 6 to 40 nucleotides in led, which have sufficient complementarity to from a duplex having a melting temperature of greater than 40° C. under physiological conditions are particularly suitable for use in the present invention. The polynucleotide may be a polynucleotide which hybridises to under conditions of medium to high stringency such as 0.03M sodium chloride and 0.03M sodium citrate at from about 50 to about 60 degrees centigrade.

Antisense oligonucleotides may be chemically modified. For example, phosphorothioate oligonucleotides may be used. Other deoxynucleotide analogs include methylphosphonates, phosphoramidates, phorphorodithioates, N3'P5'-phosphoramidates and oligoribonucleotide phosphorothioates and their 2'-O-alkyl analogs and 2'-O-methylribonucleotide methylphosphonates.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

An nucleic acid suitable for use in the invention may act via an RNA interference (RNAi) mechanism. Such a nucleic acid is typically a double-stranded RNA and has a sequence substantially similar to part of the target mRNA. Preferred nucleic acids of this type are typically short, for example 15mers to 25mers, in particular 18mers to 23mers. These short nucleic acids may be referred to as interfering RNAs (iRNA).

The use of short nucleic acids of the type described above is preferred because such inhibitors do not appear to trigger viral defence mechanisms of higher organisms. Such nucleic acids can be used to inhibit translation of the mRNA.

Alternatively, small fragments of sequence encoding the target gene product (or a sequence substantially similar thereto) may be provided, cloned back to back in a suitable vector. The vectors described above are suitable for expression of such back to back sequences. Expression of the sequence leads to production of the desired double-stranded RNA.

A nucleic acid suitable for use in a complex of the invention may comprise a sequence which encodes an antigen. An antigen is a molecule which contains one or more epitopes that will stimulate a host's immune system to make a cellular antigen-specific immune response, or a humoral antibody response. A suitable nucleic acid sequence encoding an antigen can be derived from any known organism or pathogen, e.g. a virus, a bacterium, a parasite, a plant, a protozoan, or a fungus. The term also includes tumour antigens. The antigen typically comprises one or more T cell epitopes. "T cell epitopes" are generally those features of a peptide structure capable of inducing a T cell response. In this regard, it is accepted in the art that T cell epitopes comprise linear peptide determinants that assume extended conformations within the peptide-binding cleft of MHC molecules, (Unanue et al. Science 236, 551-557, 1987). As used herein, a T cell epitope is generally a peptide having about 8-15, preferably 5-10 or more amino acid residues. A nucleic acid suitable for use in a complex of the invention may encode such a T cell epitope.

The high levels of transfection make the complex of the invention particularly suitable for the production of host cells capable of producing a desired protein, so-called "cell factories". Thus, a nucleic acid suitable for use in a complex of the invention may encode a protein that is commercially useful, for example industrially or scientifically useful, for example an enzyme; pharmaceutically uses, for example, a protein that can be used therapeutically or prophylactically as a medicament or vaccine; or diagnostically useful, for example, an antigen for use in an ELISA.

A biologically-active material for use in a complex of the invention may be a peptide or polypeptide. Suitable peptides/polypeptides are those encoded by one of the nucleic acids set out above. Thus, the peptide/polypeptide may be, for example, one that is absent or deficient in a genetic disease or an antigen or immunogen. Alternatively, the peptide/polypeptide may be, for example, a natural hormone such as tissue insulin, calcitonin and human growth hormone, or a synthetic analogue of such a natural hormone. Further peptides/polypeptides which may be used in a complex of the invention include interleukin-2, tumour necrosis factor, tissue plasminogen activator, factor VIII, erythropoietin, growth factors such as epidermal growth factor, growth hormone releasing factor, neural growth factor and toxic peptides such as ricin, diphtheria toxin, or cobra venom factor, capable of eliminating diseased or malignant cells. Fragments of any of the polypeptides mentioned above may also be used in a complex of the invention.

Peptides/polypeptides suitable for use in a complex of the invention may be chemically modified, e.g. post-translationally modified. For example, they may be glycosylated or comprise modified amino acid residues. They may also be modified by the addition of histidine residues to assist their purification or by the addition of a signal sequence to promote insertion into the cell membrane.

A biologically-active material for use in a complex of the invention may be a small molecule. Preferred small molecules are therapeutic agents, for example steroids such as hydrocortisone, fluocinolone acetonide, fluocinonide and dexamethasone, non-steroidal anti-inflammatory agents such as 1-acetylsalicyclic acid, antiviral nucleosides such as AZT, acyclovir and gancyclovir, or phospholipid derivatives of such antiviral nucleosides, antibiotics, anaesthetic agents, cytostatic agent or immunomodulators. A complex of the invention may also contain a sunscreen or a cosmetic.

A complex of the invention will typically comprise a ratio of from 0.25 to 12:1 by weight of a lipid of the invention: a biologically-active material (such as a nucleic acid), for example a ratio of from 0.5 to 8:1 by weight of a lipid of the invention: a biologically-active material, such as from 0.75 to 4:1 weight of a lipid of the invention: a biologically-active material, for example from 1 to 2:1 by weight of a lipid of the invention: a biologically-active material.

A complex of the invention may comprise an integrin-binding component, for example an integrin-binding peptide. An integrin-binding component suitable for use in a complex of the invention is any such component which is capable of binding specifically to integrins found on the surface of cells. The integrin-binding component may be a naturally occurring integrin-binding ligand, for example, an extra-cellular matrix protein, a viral capsid protein, the bacterial protein invasin, a snake venom disintegrin protein, or an integrin-binding fragment of any such protein. Such integrin-binding proteins and fragments thereof may be obtained from natural sources or by recombinant techniques, but they are difficult to synthesise and purify in large amounts, they require conjugation directly to DNA or RNA or to polycationic elements for DNA or RNA binding and are immunogenic in vivo.

It is thus preferable to use integrin-binding peptides, in particular because of their ease of synthesis, purification and storage, their potential for chemical modification, and their potentially low immunogenicity in vivo. Examples of integrin-binding peptides are given in Verfaille, 1994 #635; Wang, 1995 #645; Staatz, 1991 #539; Pierschbacher, 1984 #314; Massia, 1992 #86; Clements et al. J. Cell Science 107, 2127-2135, 1994; Lu et al., Biochemistry J. 296, 21-24, 1993; and in Koivunen et al., Biol/Technology 13, 265-270, 1995; Koivunen et al., Biological Chemistry 268, 20205-20210, 1993; Koivunen et al., J. Cell. Biology 124(3), 373-380, 1994; O'Neil et al., Proteins 14, 509-515, 1992; Healy et al., Biochemistry 34, 3948-3955, 1995; and Pasqualani et al., J. Cell. Biology 130, 1189-1196, 1995.

As indicated above, the peptides of the invention contain the conserved amino acid sequence arginine-glycine-aspartic acid (RGD), and these bind with high affinity to integrins. The affinity between integrin and peptide ligands is influenced by the amino acid sequence fling the RGD domain. Peptides having a cyclic region in which the conformational freedom of the RGD sequence is restricted generally have a higher affinity for integrin receptors than do their linear counterparts. Such cyclic peptides are particularly preferred. Cyclic peptides may be formed by the provision of two cysteine residues in the peptide, thus enabling the formation of a disulphide bond. A cysteine residue may be separated from the RGD sequence by one or more residues, for example, up to six residues, or may be immediately adjacent to the RGD sequence, although preferably both cysteines are not immediately adjacent to the ends of the RGD sequence.

An example of an amino acid sequence that will permit cyclisation by disulphide bond formation is CRGDMFGC. A peptide that consists of or comprises the sequence CRGDMFGC may advantageously be used in the present invention. Examples of peptides that comprises the sequence CRGDMFGC and that are effective integrin-binding ligands are the peptides GGCRGDMFGC, GGCRGDMFGCG, GGCRGDMFGCA and GACRGDMFGCA.

The peptide GACDCRGDCFCA has the potential to form two disulphide bonds for stabilising the RGD loop. That peptide and others having the potential to form two RGD-stabilising disulphide bonds, may be particularly useful as integrin-binding ligands according to the present invention.

A further useful peptide is GACATRWAFECG.

However, not all integrin-binding peptides contain the conserved RGD sequence. For example, the peptides GACRRETAWACA, GACRRETAWACG and XSXGACRRETAWACG are integrin-specific peptides. Other peptides comprising the sequence CRRETTAWAC or CRRETAWAC may be used, as may other non-RGD peptides, particularly those that have the potential for disulphide bond formation.

Peptide sequences may be designed on the basis of known ligands, for example, on the basis of integrin-binding domains of naturally-occurring integrin-binding ligands, or on the basis of known peptides that bind to integrins.

As stated above, integrins are a family of heterodimeric proteins found on the surface of cells. They consist of several different and subunits. Some integrins a found on many types of cells, others are more specific, for example, 5 and v integrins are widespread and are found on a diverse range of cells. Integrins-binding ligands can vary in their affinity for different integrins. For example, GACRGDMFGCA (peptide 1) has affinity for 5 and av integrins but is non-specific (O'Neil et al. 1992, supra; Hart et al. 1997, supra). GACDCRGDCFCA (peptide 5) has high affinity for integrin v but is not v-specific (Koivunen et al. 1995, supra; Hart et al. 1997, supra). GACRRETAWACG, however, which does not contain the conserved RGD region, is 51-specific (Koivunen et al. 1995, supra). Various integrin-binding peptides and their integrin specificity are set out below:

| Peptide number and integrin specificity | Sequence |
|---|---|
| Peptide 1 (αv, α5β1) | GACRGDMFGCA |
| Peptide 2 (αv, α5β1) | GACRGDMFGCGG |
| Peptide 5 (αv) | GACDCRGDCFCA |
| Peptide 6 (α5β1) | GACRRETAWACG |
| Peptide 7 (α4β1) | GAGPEILDVPST |
| Peptide 8 (α4β1) | GACQIDSPCA |
| Peptide 9 (α5β1) | GACRRETAWACGKGACRRETAWACG |

Yet further possibilities include GA-CXCG where X is SERSMNF, YGLPHKF, PSGAARA, VKSMVTH, or LQHKSMP.

Alternative oligopeptides may be used in conjunction with or instead of an integrin-binding peptide, for example alternative targetting ligands, such as oligopeptides identified by panning with phage-based peptide-display libraries; membrane-active peptides such as melittin; fragments of the HIV tat protein; single chain Fv regions of antibodies; VP22; peptides containing nuclear localisation sequences; mitochondrial localisation sequences; and peptides based on the influenza virus haemagglutinin protein.

A complex of the invention will typically comprise a ratio of from 0.25 to 4:4 by weight of a lipid of the invention: an integrin-binding peptide, for example a ratio of from 0.5 to 2:4 by weight of a lipid of the invention: an integrin-binding peptide, such as from 0.75 to 1:4 by weight of a lipid of the invention: an integrin-binding peptide.

In general, complexes of the invention will comprise a cationic component, such as a cationic polymer. This is particularly the case for complexes where the biologically-active material is a nucleic acid. Cationic polymers suitable for use in the invention are typically capable of binding to a nucleic acid. Especially preferred cationic polymers are capable of condensing nucleic acids into a particle with a diameter of from about 50 nm to about 150 nm. Generally, suitable cationic polymers are low molecular weight polymers and the number of positive charges per polymer molecule is typically from about 7 to about 50, preferably from about 7 to about 25 or more preferably from about 12 to about 16. Suitable cationic polymers may have any number of cationic monomers, although generally the polymer must retain the ability to bind nucleic acids. For example, from 3 to 100 cationic monomers may be present, for example, from 10 to 20.

Suitable polymers include oligolysine, for example having from 10 to 20 lysine residues, for example, from 15 to 17 residues, especially 16 residues, i.e [K]$_{16}$. Thus, poly-L-lysine (pLL) which has a molecular weight of 3.4 kDa (and which has an average of 16 positive charges per molecule) is preferred. Other suitable polymers include polyethylenimine (PEI) which has a molecular weight of 2 kDa (with an average of 12 positive charges per molecule at neutral pH) and polyamidoamine dendrimers. Suitable peptides are disclosed in U.S. Ser. Nos. 09/424656 and 08/836786, the disclosures of which are incorporated herein by reference.

The polymers pLL and pEI will condense RNA and DNA in water or 10 mM HEPES. Typically, cationic polymers with a pKa of greater than 9.0 (e.g. pLL) generally do not possess endosomolytic activity and require the presence of an endosome-disrupting agent, for example chloroquine, to enable them to gain access into the cytosol.

The polycationic component may advantageously be linked or otherwise attached to the integrin-binding component. For example, a polycationic polymer may be chemically bonded to an integrin-binding component, for example, by a peptide bond in the case of an oligolysine. Other types of suitable bonds are thioether and disulphide bonds. The polycationic component may be liked at any position of the integrin-binding component. Preferred combinations of integrin-binding component and polycationic polymer are an oligolysine, especially $[K]_{16}$, linked via a peptide bond to an integrin-binding peptide, for example any one of the peptides set out described above.

A complex of the invention will typically comprise a ratio of from 0.25 to 4:4 by weight of a lipid of the invention: a polycationic component (such a polycationic peptide), for example a ratio of from 0.5 to 2:4 by weight of a lipid of the invention: a polycationic component, such as from 0.75 to 1:4 by weight of a lipid of the invention: a polycationic component.

Where the integrin-binding peptide and polycationic component are combined the ratio of a lipid of the invention to the combined peptide is as given above for an integrin-binding peptide and polycationic component individually.

Agents other than peptides may also be introduced onto the condensing cationic polymer, for example saccharide residues or lipids, to modulate solubility and interaction of formulations with biological proteins, fluids, membranes and cells, including to specific receptors.

A neutral lipid may be used in a complex of the invention. However, a complex of the invention may be free of a neutral lipid Any neutral lipid may be used in a complex of the invention, although typically those that have membrane destabilising properties are preferred. An example of a suitable neutral lipid which has membrane destabilising properties is dioleyl phosphatidylethanolamine (DOPE). DOPE has membrane destabilising properties sometimes referred to as "fusogenic" properties. The ratio of neutral lipid; a lipid of the invention is from about 0.5 to 2:1 for example 1:1.

The total amount of lipid in comparison to the other components of a complex of the invention is as set out above for a lipid of the invention individually.

According to a sixth embodiment of the invention, there is provided an integrin-binding peptide having the suture:

[DNA-Binding]-[Spacer]$_k$-[Ligand]

wherein the DNA-Binding portion is a cationic polymer comprising from 3 to 100 cationic monomers, the ligand portion is an integrin-binding ligand having the conserved amino acid sequence arginine-glycine-aspartic acid (RGD), k is an integer between 1 and 5, and the spacer portion has a general formula (X):

$$-NH-[X^1-O]_p-X^2-CO- \quad (X)$$

wherein $X^1$ and $X^2$ are the same or different and represent $C_{1-6}$ alkylene groups, and 1 is an integer from 1 to 15.

Preferably the cationic polymer comprises from 10 to 20 cationic monomers. Preferred cationic polymers are oligolysines. Preferably the oligolysine has from 10 to 20, more preferably from 15 to 17, and most preferably 16, lysine residues, i.e. $[K]_{16}$. Thus, poly-L-lysine (pLL) which has a molecular weight of 3.4 kDa (and which has an average of 16 positive charges per molecule) is preferred. Other suitable polymers include polyethylimine (PEI) which has a molecular weight of 2 kDa (with an average of 12 positive charges per molecule at neutral pH) and polyamidoamine dendrimers. Suitable peptides are disclosed in U.S. Ser. Nos. 09/424656 and 08/836786, the disclosures of which are incorporated herein by reference.

In the peptides disclosed above, the spacer portion is hydrophilic in nature, based on a polyalkylene type structure, for example a polyethylene structure. A general synthesis strategy for incorporating the spacer group into a peptide involves the preparation of a corresponding amino acid. The amino acid can then be incorporated into the peptide, for example by automated solid-phase peptide synthesis using Fmoc strategy. A suitable scheme is Scheme 1 shown below.

Scheme 1:

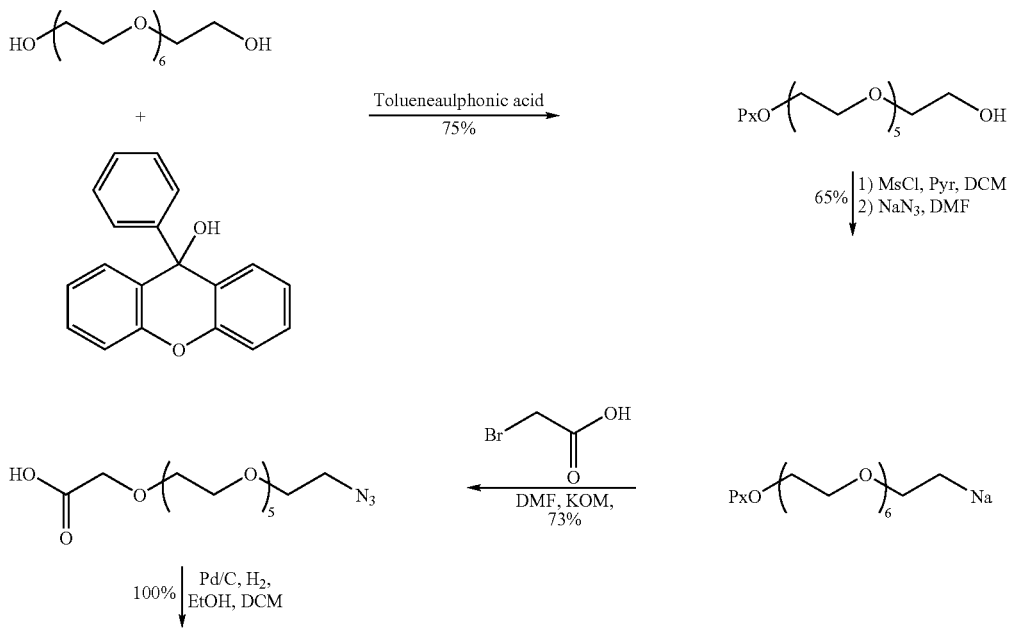

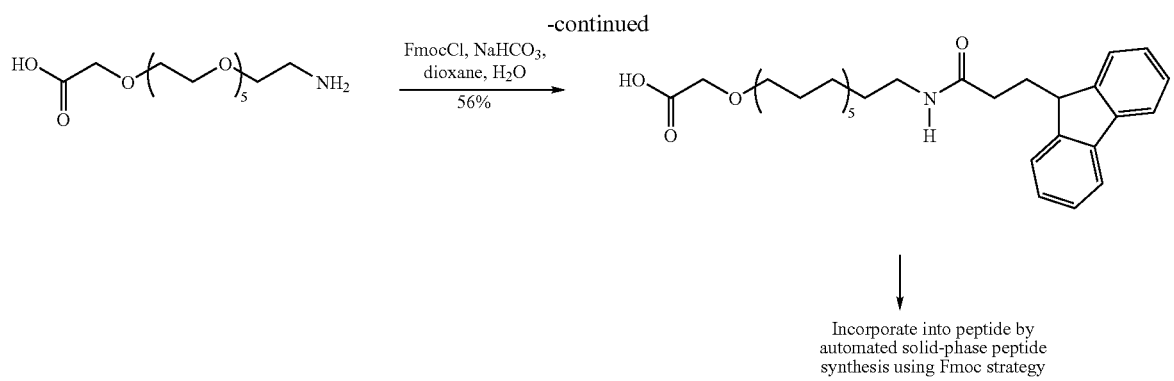

Incorporate into peptide by automated solid-phase peptide synthesis using Fmoc strategy By appropriate choice of the starting materials other spacer groups, e.g. having a greater or lesser number of PEG groups, can be prepared.

The inventors have surprisingly found that the presence of the particular spacer groups having the formula (X), according to the sixth embodiment of the invention, can increase ability of the peptides to bind to integrins, thus affecting transfection activity. Furthermore, it has also been found that peptides having such spacer groups have a lower tendency to aggregate in PBT than those made with peptides 6. The peptides of this embodiment of the invention show synergistic results with lipids of the present invention, and particularly with lipids having a PEGylated groups, e.g. those of (I), (II) or (V) when $R^6$ is —[B—O]$_m$B-Q, or of formula (III).

In the spacer portions of the peptides preferably $X^1$ is a $C_{1-4}$ alkylene group, more preferably a $C_{1-2}$ alkylene group and most preferably —CH$_2$CH$_2$—. $X^2$ is preferably a $C_{1-4}$ alkylene group, more preferably a $C_{1-2}$ alkylene group and most preferably methylene.

The integer p is preferably from 1 to 10, more preferably from 2 to 8. Suitable values of p include 3, 4, 5, 6, 7 and 8.

The integer k is preferably an integer of from 1 to 5, more preferably 1, 2 or 3, more preferably 1 or 2, and most preferably 1. When k is an integer greater than one, the spacer groups may be the same or different. For example, when k is 2, the peptide may comprise one spacer group where p is 3 and another spacer group where p is 6, or could comprise two spacer groups where p is 3.

A complex of the invention may be prepared by a process which comprises admixing the components of the complex. Although, the components may be admixed in any order, it is generally preferable that the lipid component is not added last. In the case where there is a combined integrin-binding peptide/polycationic component, it is generally preferable to combine the components in the following order: lipid; combined integrin-binding peptide/polycationic component; biologically-active material. The components of a complex of the invention are preferably admixed in the amounts set out above.

Thus a typical complex of the invention may be prepared by admixing a lipid of the invention/combined integrin-binding peptide-cationic component (such as [K]$_{16}$GACRRE-TAWACG)/nucleic acid (such as DNA) in the weight ratio 0.75:4:1. 1:4:1 or 2:4:1. If a neutral lipid is present, it is typically present in a weight ratio of 1:1 lipid of the invention: neutral lipid and the total amount of lipid relative to the other components is as set out in the previous sentence.

The invention also provides a mixture which comprises: a lipid; and one or more of an integrin-binding peptide, a poly- cationic component and a neutral lipid. All of the components of such a mixture may be as set out above. Such a mixture may be used to produce a biologically-active material containing complex of the invention by the incorporation of a biologically-active material with the mixtures for example by admixture.

The present invention further provides a process for the production of a complex of the present invention, which comprises admixing a biologically-active material with a mixture of the invention. The preferred components, preferred combinations of components, preferred ratios of components and preferred order of mixing, both with regard to the mixture and to the production of a complex are as described above in relation of the complex of the invention.

A complex of the invention may be used in a process for transfecting a cell with a biologically-active material. In such a process, a host cell is contacted with a complex of the invention. A complex of the invention may also be used in a process for expressing a nucleic acid in a host cell. Such a process comprises contacting the host cell with a complex of the invention which comprises a nucleic acid. The host cell is then subjected to conditions that enable the cell to express the nucleic acid, for example it is cultured in a medium which allows expression of the nucleic acid.

A complex of the invention may be further used in a process for the production of a polypeptide. In such a method a host cell is transfected with a nucleic acid using the method set out above. The transfection is carried out under conditions suitable for expression of the polypeptide encoded by the nucleic acid or, alternatively, the transfected cell is transferred to conditions suitable for expression of the polypeptide encoded by the nucleic acid. The polypeptide may then be recovered from the host cell or from the culture medium.

In all of the methods set out above, the host cell may be any host cell. Thus, the cell may be a prokaryotic cell or a eukaryotic cell. The cell may be from a bacterium, a mycobacterium, a protozoan, a parasite, a fungus a plant or an animal. Suitable animal cells are mammalian cells, for example human cells.

All of the methods may be carried out in vivo, in vitro or ex vivo. Also, cells may be obtained from a host, transfected according to the method set out above, and then returned to the host. The invention also provides a cell transfected with a complex of the invention and progeny cells derived from such a transfected cell.

The various components that make up the complex of the invention may be premixed or they may be packaged, for example in a two or more part kit, for mixing shortly prior to or during administration. Thus, the invention also provides a kit for delivery of a biologically-active material to a cell, which kit comprises a mixture of the invention or components suitable for the preparation of a mixture of the invention. Thus, a kit may comprise a lipid of formula (I) to (V) as set out above and one or more of an integrin-binding peptide, a polycationic component and a neutral lipid (all as described above). The kit may also comprise a biologically-active material. For example, the kit may comprise a nucleic acid, optionally in the form of a plasmid or vector which may be empty or comprise a coding sequence.

A kit of the invention may comprise appropriate buffers and/or control cells. Also, a kit of the invention may comprise appropriate packaging and instructions for using the kit in one of the methods set out above. Thus, the instructions may indicate the preferred ratios of the components and the preferred order of admixing the components, for example as described above. A kit may be used for producing a complex suitable for use in gene therapy, vaccination, antisense of iRNA therapy. Alternatively, it may be used for producing a complex suitable for transfecting a host cell with a nucleic acid encoding a commercially useful protein, i.e. to produce a so-called "cell" factory.

A complex of the invention may be used in a method of treatment or vaccination. Treatment according to the invention may be prophylactic or therapeutic.

Typically, treatment according to the invention is by gene therapy, anti-sense therapy or iRNA therapy. Thus, a complex of the invention may be used in a method for nucleic acid transfer, for example in a method of treatment of the human or animal body by therapy. A complex of the invention may also be used for the manufacture of a medicament for use in nucleic acid transfer, for example in treatment of the human or animal body by therapy, especially in the treatment of a condition caused by or related to a genetic defect or modification. The condition of a patient suffering from such a condition can be improved by administration of a complex of the invention. A therapeutically effective amount of a complex of the invention may be given to a host in need thereof. The host may be a human or non-human animal.

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, HIV, HCV and herpes simplex virus. Targets for anti-sense therapy are also known. Further targets for gene therapy and anti-sense therapy are being proposed as knowledge of the genetic basis of disease increases, as are further targets for gene vaccination.

A complex of the invention may be used in vaccination. Thus, a complex of the invention may be used to deliver an antigen or a nucleic acid encoding an antigen. That is to say, a complex of the invention may be used in gene vaccination. A complex of the invention may be used to elicit an immune response against a wide variety of antigens for the treatment and/or prevention of a number of conditions including, but not limited to, cancer, allergies, toxicity and infection by pathogens such as viruses, bacteria, fungi, and other pathogenic orgasms.

Suitable viral antigens and nucleic acids encoding such antigens for use in the complexes of the invention include, but are not limited to, those obtained or derived from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). See, e. g., International Publication Nos. WO 89/04669; WO 90/11089; and WO 90/14436. The HCV genome encodes several viral proteins, including E1 and E2. See, e. g., Houghton et al. (1991) Hepatology 14: 381-388. Nucleic acid molecules containing sequences encoding these proteins, as well as antigenic fragments thereof, will find use in the present methods. Similarly, he coding sequence for the 8-antigen from HDV is known (see, e. g., U.S. Pat. No. 5,378,814).

In like manner, a wide variety of proteins, and nucleic acids encoding such proteins, from the herpesvirus family can be used as antigens in the present invention, including proteins derived from herpes simplex virus (HSV) types 1 and 2, such as HSV-1 and HSV-2 glycoproteins gB, gD and gH; antigens from *varicella* zoster virus (VZV), Epstein-Barr virus (EBV) and cytomegalovirus (CMV) including CMV gB and gH; and antigens from other human herpesviruses such as HHV6 and HHV7. (See, e. g. Chee et al. (1990) Cytomegaloviruses (J. K. McDougall, ed., Springer Verlag, pp. 125-169; McGeoch et al. (1988) J. Gen. Viral. 69: 1531-1574; U.S. Pat. No. 5,171, 568; Baer et al. (1984) Nature 310: 207-211; and Davison et al. (1986) J. Gen. Virol. 67: 1759-1816.)

Human immunodeficiency virus (HIV) antigens, such as gp120 molecules for a multitude of HIV-1 and HIV-2 isolates, including members of the various genetic subtypes of HIV, are known and reported (see, e. g., Myers et al., Los Alamos Database, Los Alamos National Laboratory, Los Alamos, N.Mex. (1992); and Modrow et al. (1987) J. Virol. 61: 570-578) and antigen-containing nucleic acid sequences derived or obtained from any of these isolates will find use in the present invention.

Furthermore, other immunogenic proteins derived or obtained from any of the various HIV isolates will find use herein, including nucleic acid sequences encoding one or more of the various envelope proteins such as gap 160 and gp41, gag antigens such as p24gag and p55gag, as well as proteins derived from the pol, env, tat, vif, rev, nef, vpr, vpu and LTR regions of HIV.

Antigens derived or obtained from other viruses will also find use herein, such as without limitation, antigens from members of the families Picornaviridae (e. g., polioviruses, rhinoviruses, etc.); Caliciviridae; Togaviridae (e. g., rubella virus, dengue virus etc.); Flaviviridae; Coronaviridae; Reoviridae (e. g., rotavirus, etc.); Birnaviridae; Rhabodoviridae (e. g., rabies virus, etc.); Orthomyxoviridae (e. g., influenza virus types A, B and C, etc.); Filoviridae; Paramyxoviridae (e. g., mumps virus, measles virus, respiratory syncytial virus, parainfluenza virus, etc.); Bunyaviridae; Arenaviridae; Retroviradae (e. g., HTLV-I; HTLV-11; HIV-1 (also known as HTLV-111, LAV, ARV, hTLR etc.)), including but not limited to antigens from the isolates HIVIIIb, HIVSF2, HTVLAV, HIVLAI, HIVMN); HIV-1CM235, HIV-1; HIV-2, among others; simian immunodeficiency virus (SIV); Papillomavirus, the tick-bourne encephalitis viruses; and the like. See, e. g. Virology, 3rd Edition (W. K. Joklik ed. 1988); Fundamental Virology, $2^{nd}$ Edition (B. N. Fields and D. M. Knipe, eds. 1991), for a description of these and other viruses. Nucleic acid sequences encoding such antigens may of course also be used in a complex of the invention.

In some contexts, it may be preferable that a selected antigen is obtained or derived from a viral pathogen that typically enter the body via a mucosal surface and is known to cause or is associated with human disease, such as, but not limited to, HIV (AIDS), influenza viruses (Flu), herpes simplex viruses (genital infection, cold sores, STDs), rotaviruses (diarrhoea), parafluenza viruses (respiratory infections), poliovirus (poliomyelitis), respiratory syncytial virus (respiratory infections), measles and mumps viruses (measles, mumps), rubella virus (rubella), and rhinoviruses (common cold). Again, nucleic acid sequences encoding such antigens may be used in a complex of the invention.

Suitable bacterial and parasitic antigens can be obtained or derived from known causative agents responsible for diseases including, but not limited to, Diphtheria, Pertussis, Tetanus, *Tuberculosis*, Bacterial or Fungal Pneumonia, Otitis Media, Gonorrhoea, *Cholera*, Typhoid, Meningitis, Mononucleosis, Plague, Shigellosis or Salmonellosis, Legionnaire's Disease, Lyme Disease, Leprosy, Malaria, Hookworm, Onchocerciasis, Schistosomiasis, Trypamasomialsis, Lesmaniasis, *Giardia*, Amoebiasis, Filariasis, *Borelia*, and Trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease. Again, nucleic acid sequences encoding such antigens may be used in a complex of the invention.

Specific pathogens from which antigens can be derived include *M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pneumophila, Yersinia pestis, Streptococcus* (types A and B), *Pneumococcus, Meningococcus, Hemophilus influenza* (type b), *Toxoplasma gondic*, Complylobacteriosis, *Moraxella catarrhalis*, Donovanosis, and Actinomycosis; fungal pathogens including *Candidiasis* and *Aspergillosis*; parasitic pathogens including *Taenia*, Flukes, Roundworms, Amebiasis, Giardiasis, *Cryptosporidium, Schistosoma, Pneumocystis carinii*, Trichomoniasis and Trichinosis. Thus, the present invention can also be used to provide a suitable immune response against numerous veterinary diseases, such as Foot and Mouth diseases, Coronavirus, *Pasteurella multocida, Helicobacter, Strongylus vulgaris*, Actinobacillus pleuropneumonia, Bovine viral diarrhoea virus (BVDV), *Klebsiella pneumoniae, E. coli, Bordetella pertussis, Bordetella parapertussis* and *brochiseptica*. Again, nucleic acid sequences encoding an antigen as set out above may be used in a complex of the invention.

Typically, a nucleotide sequence corresponding to (encoding) one or more of the above-listed antigen(s) is used in a complex of the invention.

A complex of the invention may be in the form of a pharmaceutical composition which additionally comprises a pharmaceutically-acceptable carrier, diluent or excipient for example water or a physiologically-acceptable buffer. Similarly, a vaccine composition comprises a complex of the invention and a pharmaceutically-acceptable carrier, diluent or excipient for example water or a physiologically-acceptable buffer.

Such pharmaceutical and vaccine compositions may be supplied in any suitable dispenser, for example a puffer.

A complex of the invention may be administered in a variety of dosage forms. Thus, it can be administered orally, for example as tablets, troches, lozenges, aqueous or oily suspensions, dispersible powders or granules. The complexes may also be administered parenterally, either subcutaneously, intravenously, intramuscularly, intrasternally, transdermally or by infusion techniques. The complexes may also be administered as suppositories. A physician will be able to determine the required route of administration for each particular patient.

The formulation of a complex for use in prophylaxis, treatment or vaccination will depend upon factors such as the nature of the exact complex, whether a pharmaceutical or veterinary use is intended, etc. A complex of the invention may be formulated for simultaneous, separate or sequential use.

A complex of the invention is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch: lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuff; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of a complex is administered to a patient. The dose of a complex may be determined according to various parameters, especially according to the substance used; the age, weight and condition of the patient to be treated; the route of administration; and the required regimen. Again, a physician will be able to determine the required route of administration and dosage for any particular patient.

Typically, the amount of nucleic acid delivered in a complex of the invention will be in the range of from 1 µg to 1 g, preferably from 100 µg to 10 mg, according to the activity of the specific formulation, the age, weight and conditions of the subject to be treated, the type and severity of the degeneration and the frequency and route of administration. A single dose may be administered daily or alternatively, may multiple doses, for example two, tree, four or five doses may be administered daily.

The amount of nucleic acid referred to above may represent the total amount administered in the treatment regime or may represent each separate administration in the regime.

If the complex is to be used in vaccination, it may be administered to the host in one or more administrations. Typically after the initial administration a "booster" can be given. Typically the host is given 1, 2, 3 or more separate ministrations, each of which is separated by at least 12 hours, 1 day, 2 days, 7 days, 14 days, 1 month or more.

The lipids of the invention can be prepared by analogy with known methods. For example, compounds of formula (I) in which $R^6$ is -[A-Y]$_n$-$R^4$ can be prepared as follows:

Scheme 2:

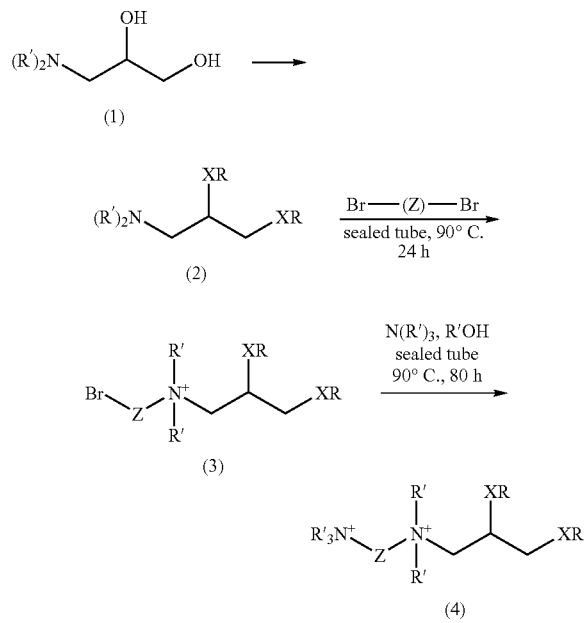

Scheme 3:

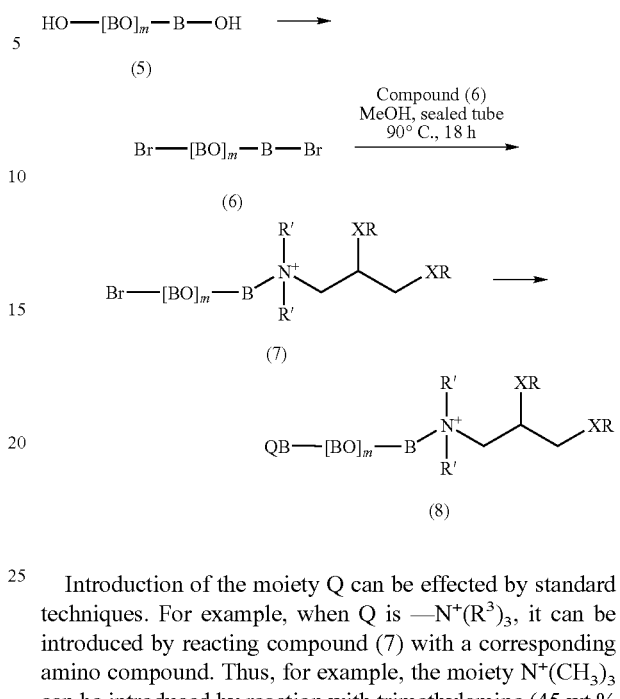

R' in the above reaction scheme is, of course, defined as $R^3$ and $R^4$ above. X in the above reaction scheme is defined as $X^1$ and $X^2$ above. R in the above reaction scheme is defined as $R^1$ and $R^2$ above. Z in the above reaction scheme corresponds to the moiety -[A-Y]$_n$$R^4$ except for the absence of the terminal —$N^+(R^4)_3$.

When X is —O—, the R moieties can be introduced in the first step by the reaction of compound (1) with a compound of formula L-R where L is a leaving group such as a mesylate, in the presence of NaH in THF under reflux. When X is —O—CO—, the XR moieties can be introduced by reaction with RCO$_2$H, in the presence of EDCl, DMAP, triethylamine and DCM. Typically the reaction is effected in a dark environment at room temperature.

When the two XR moieties are different, typically one XR moiety is introduced in a first step and a second XR moiety is introduced in a second step. One of the hydroxy groups on compound (1) can, if necessary be protected prior to such a two stage reaction step by a standard hydroxy-protecting group. The protecting group would, of course, than be removed after introduction of the first XR moiety and before introduction of the second XR moiety.

If necessary, the Z group can comprise carbamate protected amino moieties in place of quaternary ammonium moieties. Under such circumstances, the carbamate protected amino moieties in compound (4) can be deprotected and converted to quaternary ammonium moieties by standard methods. Quaternisation can, for example, be effected by reaction with $R^4$—I. The compounds (4) are generally purified by recrystallisation.

Compounds of formula (I) in which $R^6$ is —[BO]$_m$-Q can be prepared according to the following reaction scheme.

Introduction of the moiety Q can be effected by standard techniques. For example, when Q is —$N^+(R^3)_3$, it can be introduced by reacting compound (7) with a corresponding amino compound. Thus, for example, the moiety $N^+(CH_3)_3$ can be introduced by reaction with trimethylamine (45 wt % in H$_2$O) in the presence of methanol in a sealed tube at 90° C. for 24 hours.

When Q is a halogen other than bromine, it may, of course, be convenient to conduct the synthesis using a compound (6) which is appropriately halogenated. Similarly, when Q is OH, appropriate compounds (8) can be prepared by reacting a compound (5) with HBr (48% in H$_2$O), in toluene under reflux for 72 hours, to prepare a compound HO—[BO]$_m$—B—Br. This can, of course, be used in the above synthesis in place of compound (6) to yield compounds (8) in which Q is hydroxy.

Compounds in which Q is —OR' and —OC(O)R' can be prepared from corresponding compounds in which Q is hydroxy by known techniques.

Compounds of formula (II) ran be prepared from 1,4-dibromobutanediol, using dimethylamine in methanol, according to the following reaction scheme:

Scheme 4:

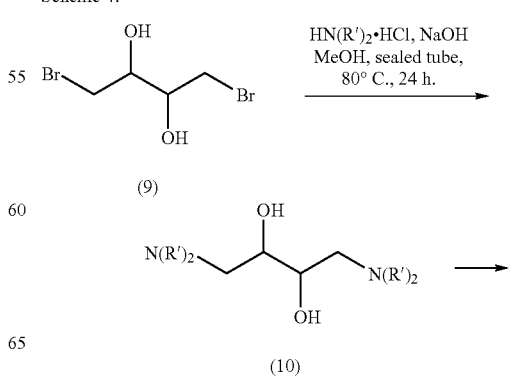

-continued

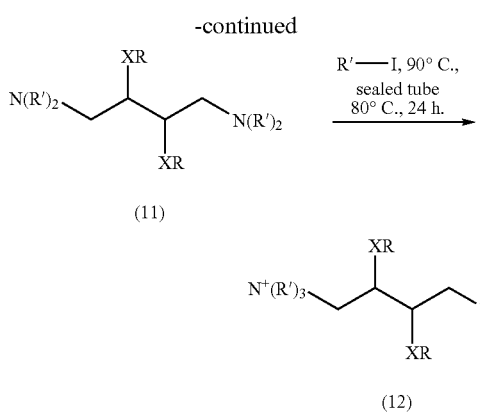

(11)

(12)

R' in the above reaction scheme is, of course, defined as $R^3$ and $R^4$ above. X in the above reaction scheme is defined as $X^1$ and $X^2$ above. R in the above reaction scheme is defined as $R^1$ and $R^2$ above.

Each R in the above reaction scheme can be the same or different. When the two $N(R')_2$ moieties in the formula (10) are different, step (1) is typically conducted stepwise. A first —$N(R')_2$ moiety is added in a first step and a second —$N(R')_2$ moiety is added in a second step. If necessary, one of the hydroxy groups on compound (9) can be protected by a protecting group, prior to such a two stage reaction. The protecting group would, of course, then be removed after introduction of the first $N(R')_2$ moiety and before the introduction of the second $N(R')_2$ moiety.

When X is —O—, step 2 (introduction of the XR moieties) can be effected by reaction with L-R, wherein L is a leaving group such as a mesylate, in the presence of NaH in THF under reflux. When X is —O—CO—, the XR moieties can be introduced by reaction with $RCO_2H$ in the presence of EDCl, DMAP, triethylamine and DCM. Typically, the reaction is effected in a dark environment at room temperature.

When the two X moieties are different, typically, one XR moiety is introduced in a first step and a second XR moiety is introduced in a second step. One of the hydroxy groups on compound (10) can, if necessary, be protected prior to such a two stage reaction step by a standard hydroxy protecting group. The protecting group would of course then be removed after introduction of the first XR moiety and before introduction of the second XR moiety.

Although an iodine anion in used in the above scheme it will be appreciated that any suitable anion could be used.

The amino acids which are used to make the peptides of the invention can be produced in the form of protected amino acids, in particular Fmoc-protected amino acids. With regard to amino acids comprising a number of PEG units hen, using the terminology of the Examples below, the protected amino acids have the formula Fmoc-Haa(n), where n represents number of PEG groups.

The amino acids are synthesised using one of two routes. Where PEG chains of the desired length are readily available, a sequence involving selective monoprotection of one hydroxy group, followed by conversion of the other hydroxy group to a Fmoc-protected amine, deprotection of the first hydroxy group and oxidation to the carboxylic acid, is used. This is outlined in Scheme 5 below:

Scheme 5:

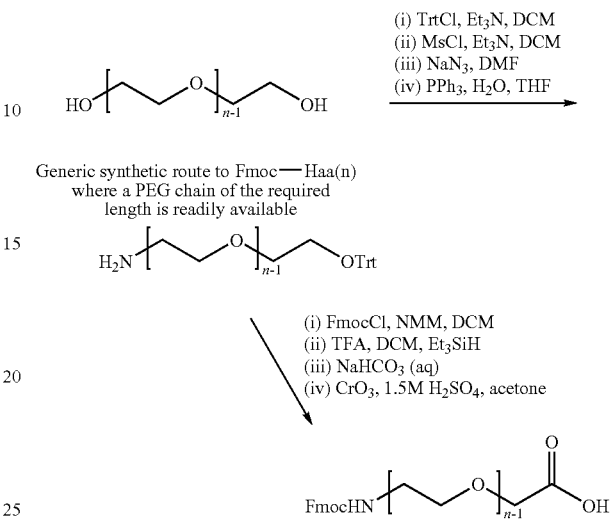

Where PEG chains of the desired length are not readily available, these are first assembled using standard methods to give a PEG chain with different protecting groups at each end. The (acid-labile) protecting group is then deprotected and the resulting free hydroxy group converted to an amino group. The benzyl group is then removed from the other end of the PEG chain using dissolving metal reduction. Fmoc protection of the amino group and oxidation of the hydroxy group to the carboxylic acid then affords the desired Fmoc-Haa(n), as shown in Scheme 6 below:

Scheme 6:

synthesis using standard techniques
⇒

Generic synthetic route to Fmoc—Haa(n) where a PEG chain of the required length is readily available TrtO⎡⎣⟋⟍O⎤⎦$_{n-1}$⟋⟍OBN (i) TFA, DCM, $Et_3SiH$
(ii) $NaHCO_3$ (aq)
(iii) MsCl, $Et_3N$, DCM
(iv) $NaN_3$, DMF
(v) $PPh_3$, $H_2O$, THF $H_2N$⎡⎣⟋⟍O⎤⎦$_{n-1}$⟋⟍OBN (i) (i) Na, $NH_3$, THF, -78° C.
(ii) Fmoc—Cl, $NaHCO_3$, dioxane, water
(iii) $CrO_3$, 1.5M $H_2SO_4$, acetone FmocHN⎡⎣⟋⟍O⎤⎦$_{n-1}$⟋C(=O)OH Peptides as described above for use in accordance with the invention may be prepared by conventional modes of synthesis. Synthetic techniques, such as a solid-phase Merrifield-type synthesis, may be preferred for reasons of purity, antigenic specificity, freedom from unwanted side products and ease of production. Suitable techniques for solid-phase peptide synthesis are well known to those skilled in the art (see for example, Merrifield et al., 1969, Adv. Enzymol 32, 221-96 and Fields et al., 1990, Int. J. Peptide Protein Res, 35, 161-214). Chemical synthesis may be performed by methods well known in the art involving cyclic sets of reactions of selective deprotection of the functional groups of a terminal amino acid and coupling of selectively protected amino acid residues, followed finally by complete deprotection of all functional groups. The Fmoc-protected amino acids described above may be introduced using these same methods well known in the art. More than one amino acid may be introduced from the Fmoc-protected amino acid (i.e. the integer k may be greater than one) using these same methods to give longer or shorter spacer groups, as required.

Synthesis may be performed in solution or on a solid support using suitable solid phases known in the art, using either automated or manual methods.

The following Examples illustrate the invention. In the Examples:

Examples 1 to 7, 17 and 18 describe the preparation of the lipids of the invention.

Examples 8 to 10 describe the preparation of Fmoc-protected amino acids.

Example 11 describes the a general peptide synthesis route.

Examples 12 to 15 relate to specific peptide synthesis routes using the Fmoc-protected amino acids of Example 8 (see Examples 13 and 14 which show the manufacture of 1HAA and 2HAA). Example 9 (see Example 12 which shows the manufacture of M109) and Example 10 (see Example 15 which shows the manufacture of Peg9). When the Fmoc-protected amino acids are incorporated into the peptides it is clearly necessary to remove the protecting Fmoc group. It is also necessary to remove the hydrogen atom at the opposite end of the molecule, in order that the amino acid can bond to the ligand portion of the molecule. For example, when the Fmoc-protected amino acid Fmoc-Haa4 is incorporated into a peptide, the resulting peptide may have the structure:

H-(Lys)$_{16}$-Haa4-Gly-Ala-Cys-Arg-Arg-Glu-Thr-Ala-Trp-Ala-Cys-Gly-OH. In this formula the group "Haa4" represents the moiety:

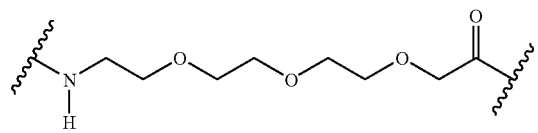

This moiety is bonded to Lys group and to a Gly group via amide linkages with the terminal —NH— or —C(O)— groups.

Example 16 describes the testing of LID systems comprising said peptides.

Example 19 describes the testing of the transfection efficiency of the lipids of Examples 17 and 18.

The reference works referred to in some of the following Examples are as follows:

Ref 1: Felgner, P. L., Gadek, T. R., Holm, M., Roman, R., Chan, R. W., Wenz, M., Northrop, J. P., Ringold, G. M., Danielsen, M., Proc. Natl. Acad. Sci. USA, 1987, 84, 7413.

Ref 2: Herve, G., Uwe Hahn, D., Hailes, H. C., Herve, A-C., Goodworth, K. J., Hill, A. M., Org. Biomol. Chem., 2003, 1, 427-435.

Ref 3: Hurley, C. A., Wong, J. B., Hailes, H. C., Tabor, A. B., J. Org. Chem., 2004, 69, 980-983.

EXAMPLE 1

[2,3-Di-(oleyloxy)-propyl]-(3-bromo-propyl)-dimethyl-ammonium bromide was prepared in a first step:

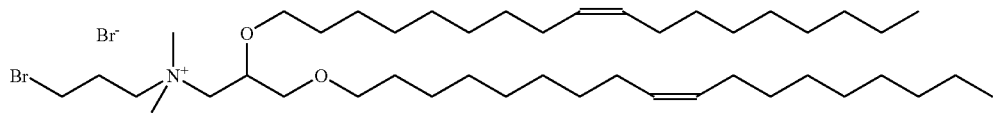

1,2-Dioleyloxy-3-dimethylamino propane (0.50 g, 0.81 mmol) and 1,3-dibromopropane (0.82 ml, 8.10 mmol) were stirred in methanol in a sealed tube at 80° C. for 18 hr. The solvent was removed in vacuo. The product was purified by flash chromatography (gradient; DCM to 10% methanol in DCM) to yield the above product as a yellow oil (0.41 g, 62%).

$R_f$=0.17 (5% methanol in DCM); $\delta_H$ (300 MHz, CDCl$_3$) 0.87 (6H, t, J 7.0 Hz, CH$_2$CH$_3$), 1.28 (44H, m), 1.57 (4H, m, OCH$_2$CH$_2$), 2.01 (8H, m, C$_2$CH=CHCH$_2$), 2.45 (2H, m, BrCH$_2$CH$_2$CH$_2$N), 3.40-4.10 (19H, m, CHO, CH$_2$O, NCH$_3$, BrCH$_2$CH$_2$CH$_2$N), 5.33 (4H, m, CH=CH); $\delta_C$ (75 MHz, CDCl$_3$) 14.50 (CH$_2$CH$_3$), 23.00-33.10, 53.25 and 53.56 (NCH$_3$), 65.00 (NCH$_2$), 66.29 (NCH$_2$), 68.87, 69.94, 72.57 and 73.78 (CHO and CH$_2$O), 130.24 and 130.48 (CH=CH); $v_{max}$ cm$^{-1}$ (Film) 3417.6, 2923.9, 2852.5, 2358.8, 1633.6, 1463.9, 1120.6;

The above product was then converted, in a second reaction step, to [2,3-Di-(oleyloxy)-propyl]-(3-trimethyl-ammonium-propyl)-dimethyl-ammonium dibromide.

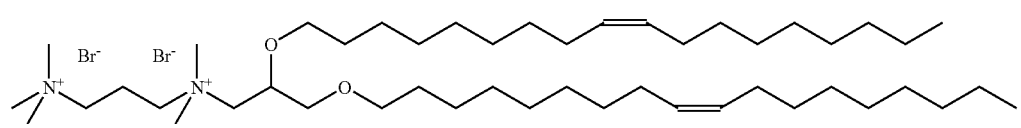

[2,3-Di-(oleyloxy)-propyl]-(3-bromo-propyl)-dimethyl-ammonium, bromide (100 mg, 0.12 mmol) and trimethylamine solution (45 wt % in H$_2$O, 0.094 ml, 0.61 mmol) were stirred in methanol (2 ml) in a sealed tube at 90° C. for 24 hr. The solvent was removed in vacuo and the resulting residue was purified by recrystallization (ethyl acetate) to yield the above product as an off white solid (86.6 mg, 82%).

δ$_H$ (300 MHz, CDCl$_3$) 0.87 (6H, t, J 6.9 Hz, CH$_2$CH$_3$), 1.28 (44H, m), 1.53 (4H, m, OCH$_2$CH$_2$), 2.01 (8H, m, CH$_2$CH=CHCH$_2$), 2.72 (2H, m, NCH$_2$CH$_2$CH$_2$N), 3.40-4.10 (28H, m, CHO, CH$_2$O, NCH$_3$, NCH$_2$CH$_2$CH$_2$N), 5.35 (4H, m, CH=CH); m/z (ESP+) 360.6 (100%, ½M$^+$); ν$_{max}$ cm$^{-1}$ (Film) 3382.4, 2922.4, 2852.0, 1655.8, 1455.7, 1116.7.

EXAMPLE 2

[2,3-Di-(oleyloxy)-propyl]-[2-(2-bromo-ethoxy)-ethyl]-dimethyl-ammonium; bromide was prepared in a first step:

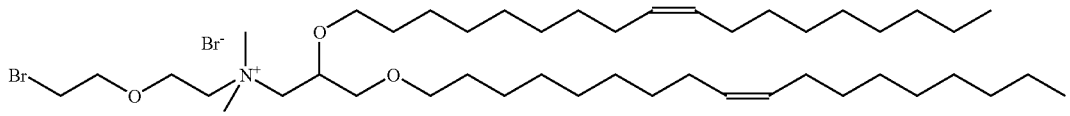

2-Bromoethyl ether (278 mg, 1.20 mmol) and 1,2-dioleyloxy-3-dimethylamino propane (300 mg, 0.48 mmol) were stirred in methanol (2 ml) at 90° C. in a sealed tube for 24 hr. The solvent was removed in vacuo. The product was purified by recrystallization (ethyl acetate) to yield the above product as a yellow oil at r.t. and a off white solid upon freezing (197 mg, 48%).

δ$_H$ (300 MHz, CDCl$_3$) 0.90 (6H, t, J 7.0 Hz, CH$_2$CH$_3$), 1.25 (44H, m), 1.52 (4H, m, OCH$_2$CH$_2$), 2.01 (8H, m, CH$_2$CH—CHCH$_2$), 3.40-4.10 (23H, m, CH$_2$O, CHO, NCH$_2$, NCH$_3$, CH$_2$Br), 5.34 (4H, m, CH=CH); m/z (ESP+) 773.6 (45%, M$^+$), 772.6 (100%, M$^+$), 771.6 (45%, M$^+$), 770.6 (88%, M$^+$); ν$_{max}$ cm$^{-1}$ (Film) 3428.2, 2926.8, 2854.0, 2343.8, 1641.8, 1464.8, 1366.5, 1122.0.

In a second step, the above product was converted to [2,3-Di-(oleyloxy)-propyl]-[2-(2-trimethyl-ammonium-ethoxy)-ethyl]-dimethyl-ammonium dibromide:

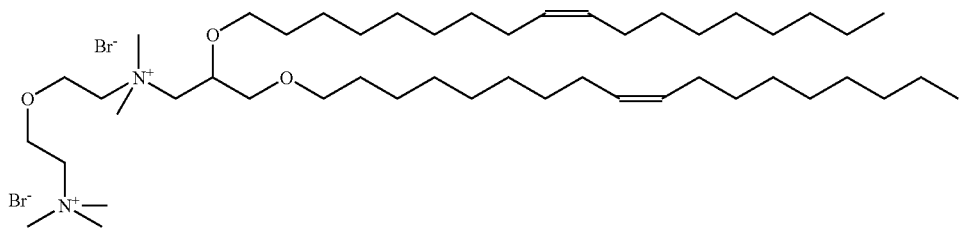

[2,3-Di-(oleyloxy)-propyl]-[2-(2-bromo-ethoxy)-ethyl]-dimethyl-ammonium bromide (100 mg, 0.12 mmol) and trimethylamine solution (45 wt % in H$_2$O, 0.31 ml, 2.35 mmol) in methanol (3 ml) were stirred at 90° C. in a sealed tube for 24 hr. The solvent was removed in vacuo. The residue was treated with diethyl ether and the precipitate was collected by filtration. The off white solid was the above product (73 mg, 67%).

δ$_H$ (300 MHz, CDCl$_3$) 0.85 (6H, t, J 6.9 Hz, CH$_2$CH$_3$), 1.22 (44H, m), 1.50 (4H, m, OCH$_2$CH$_2$), 2.01 (8H, m, CH$_2$CH=CHCH$_2$), 3.40-4.10 (32H, m, CH$_2$O, CHO, NCH$_2$, NCH$_3$), 5.35 (4H, m, CH=CH); δ$_C$ (75 MHz, CDCl$_3$) 14.46 (CH$_2$CH$_3$), 23.00-33.00, 55.23 (NCH$_3$), 65.53-74.00, 130.26 and 130.47 (CH=CH); m/z (ESP+) 375.6 (100%, ½M$^+$); ν$_{max}$ cm$^{-1}$ (Film) 3391.6, 2922.4, 2852.5, 1703.0, 1462.4, 1361.7, 1125.9.

EXAMPLE 3

2-[2-(2-Bromo-ethoxy)-ethoxy]-ethanol was produced in a first step:

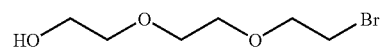

Tri(ethylene) glycol (4.50 g, 30.0 mmol) and hydrobromic acid solution (48%, 5.09 ml, 45.0 mmol) were stirred in toluene (70 ml) at reflux for 72 hr. After cooling the solution was neutralized by the addition of saturated sodium hydrogencarbonate solution. Water (50 ml) was added and the resulting mixture was extracted with DCM (3×50 ml). The chlorinated extract was dried over anhydrous magnesium sulfate and concentrated in vacuo. No further purification was required and the above product was obtained as a yellow oil (2.29 g, 36%).

$\delta_H$ (300 MHz, CDCl$_3$) 2.64 (1H, s, OH), 3.42 (2H, t, J 6.2 Hz, CH$_2$Br), 3.55-3.65 (8H, m, CH$_2$O), 3.76 (2H, t, J 6.2 Hz, CH$_2$CH$_2$Br); $\delta_C$ (75 MHz, CDCl$_3$) 30.65 (CH$_2$Br), 62.05 (CH$_2$OH), 70.70, 71.51 and 72.93 (CH$_2$O); $\nu_{max}$ cm$^{-1}$ (Film) 3415.7, 2920.0, 2871.8, 2339.5, 1641.3, 1454.2.

In a second step, the above product was converted to [2,3-Di-(oleyloxy)-propyl]-{2-[2-(2-hydroxy-ethoxy)-ethoxy]-ethyl}-dimethyl-ammonium bromide:

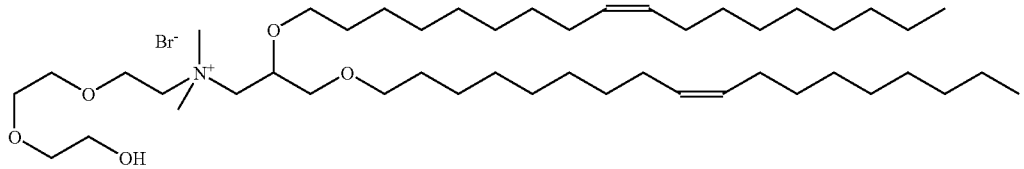

2-[2-(2-Bromo-ethoxy)-ethoxy]-ethanol (223 mg, 0.96 mmol) and 1,2-dioleyloxy-3-dimethylamino propane (300 mg, 0.48 mmol) in methanol (2 ml) were stirred at 90° C. in a sealed tube for 24 hr. The solvent was removed in vacuo. The product was purified by recrystallization (ethyl acetate) to yield the above product as a pale yellow oil at r.t. and a white solid upon freezing (247 mg, 62%).

$\delta_H$ (300 MHz, CDCl$_3$) 0.85 (6H, t, J 6.99 Hz, CH$_2$CH$_3$), 1.25 (44H, m), 1.54 (4H, m, OCH$_2$CH$_2$), 2.01 (8H, m, CH$_2$CH=CHCH$_2$), 2.88 (1H, brs, OH), 3.40-4.10 (27H, m, CH$_2$O, CHO, NCH$_2$, NCH$_3$, CH$_2$OH), 5.35 (4H, m, CH=CH); m/z (ESP+) 752.7 (100%, M$^+$); $\nu_{max}$ cm$^{-1}$ (Film) 3371.3, 2916.6, 2854.0, 2666.4, 2333.2, 1641.8, 1464.8, 1366.5, 1117.2.

EXAMPLE 4

{2,3-Di-[(Z)-octadec-9-enlyoxy]-propyl}-N-(2-{2-[2-(2-hydroxy-ethoxy)-ethoxy-]-ethoxy}-ethyl)-N,N-dimethylammonium bromide (CH300)

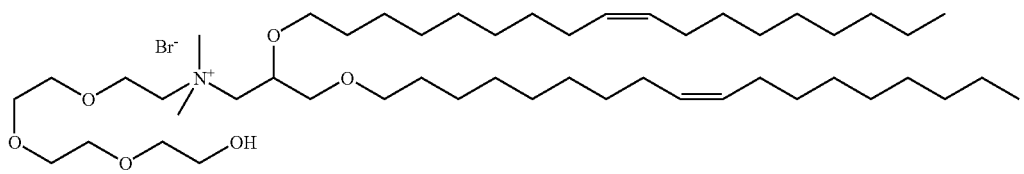

1,2-(Z-Octadec-9-enyloxy)-N,N-dimethylamino propane[1] (0.300 g, 0.48 mmol) and 11-bromo-3,6,9-trioxoundecan-1-ol[2] (0.137 g, 0.48 mmol) in methanol (2 ml) were stirred in a sealed tube at 90° C. for 24 h. The solvent was removed in vacuo and the product purified by recrystallisation (ethyl acetate) to give the titled compound (0.245 g, 58%) as a pale yellow oil at room temperature and white solid at $-18°$ C. $\nu_{max}$ (neat)/cm$^{-1}$: 3404 s, 3005 m, 2920 s, 2858 s, 1634 m, 1466 s, 1354 m; $\delta_H$ (300 MHz; CDCl$_3$) 0.85 (6H, t, J 7.0 Hz, 2×CH$_3$CH$_2$) 1.15-1.42 (44H, m), 1.54 (4H, m, 2×OCH$_2$CH$_2$), 2.01 (8H, m, 2×CH$_2$CH=CHCH$_2$), 2.58 (1H, s, br, OH), 3.43 (6H, s, N$^+$(CH$_3$)$_2$), 3.48-4.25 (25H, m, CH$_2$CHOCH$_2$, CH$_2$OCH$_2$, PEG-OCH$_2$CH$_2$O), 5.35 (4H, m, 2×CH=CH); $\delta_C$ (75.4 MHz; CDCl$_3$) 14.4 (CH$_3$CH$_2$), 23.0, 26.4, 26.6, 29.7, 29.9, 30.0, 30.1-30.4 (signal overlap), 32.3, 33.0, 53.5 and 54.0 (N$^+$(CH$_3$)$_2$), 61.7, 66.1, 67.1, 69.1, 69.7, 70.6-72.4 (signal overlap), 73.9, 130.2 (CH=CH), 130.4 (CH=CH); m/z (HRFAB+) 796.7399 ({M-Br}$^+$, C$_{49}$H$_{98}$NO$_6$ requires 796.7394; m/z (ES+) 796 ({M-Br}$^+$, 100%);

Anal. (C$_{49}$H$_{98}$NO$_6$Br.H$_2$O) found C, 66.19; H, 10.99; N, 1.50; requires C, 65.74; H, 11.26; N, 1.56%.

EXAMPLE 5

{2,3-Di-[(Z)-ocatadec-9-enyloxy]-propyl}-N-{2-[2-(2-{2-[2-(2-hydroxy-ethoxy)-ethoxy]-ethoxy}-ethoxy)-ethoxy]-ethyl}-N,N-dimethylammonium bromide

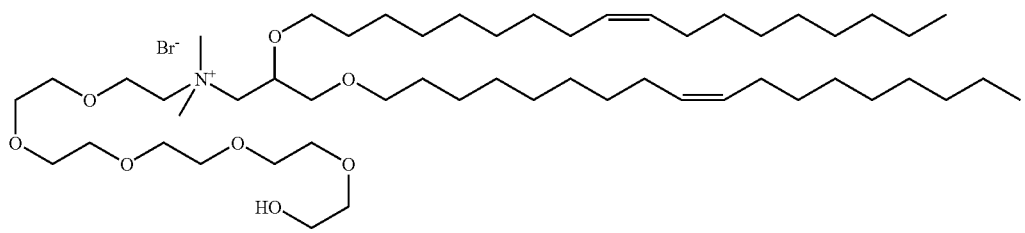

1,2-(Z-Octadec-9-enyloxy)-N,N-dimethylamino propane[1] (0.100 g, 0.16 mmol) and 17-bromo-3,6,9,12,15-pentaoxoheptadecan-1-ol[2] (0.060 g, 0.18 mmol) in methanol (1 ml) were stirred in a sealed tube at 90° C. for 24 h. The solvent was removed in vacuo and the product purified by flash chromatography on silica (10% methanol in dichloromethane) to give the titled compound (0.050 g, 32%) as a pale yellow oil. $v_{max}$ (neat)/cm$^{-1}$: 3389 s, 3005 m, 2924 s, 2853 s, 1634 m, 1464 s, 1352 m; $\delta_H$ (300 MHz; CDCl$_3$) 0.84 (6H, t, J 6.6 Hz, 2×CH$_3$CH$_2$) 1.14-1.35 (44H, m), 1.51 (4H, m, 2×OCH$_2$CH$_2$), 1.96 (8H, m, 2×CH$_2$CH=CHCH$_2$), 2.71 (1H, s, br, OH), 3.40 (6H, s, $^+$N(CH$_3$)$_2$) 3.50-4.10 (33H, m, CH$_2$CHOCH$_2$, CH$_2$OCH$_2$, PEG-OCH$_2$CH$_2$O), 5.30 (4H, m, 2×CH=CH); $\delta_C$ (75.4 MHz; CDCl$_3$) 14.1 (CH$_3$CH$_2$), 22.7, 26.0, 26.2, 27.2, 29.2-30.0 (signal overlap), 31.9, 32.6, 53.1 and 53.3 (N$^+$CH$_3$)$_2$), 61.3, 65.1, 66.7, 68.7, 69.2, 70.0-70.5 (signal overlap), 72.0, 72.8, 73.5, 129.8 (CH=CH), 130.2 (CH=CH); m/z (ES+) 885.22 ({M-Br}$^+$, 100%).

EXAMPLE 6

{2,3-Di-[(Z)-hexadec-11-enyloxy]-propyl-}-N-(2-{2-[2-(2-hydroxy-ethoxy)-ethoxy]-ethoxy}-ethyl)-N,N-dimethylammonium bromide

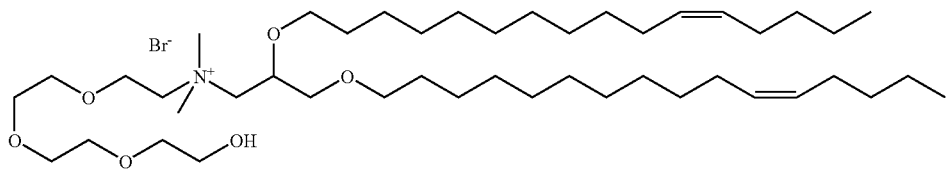

1,2-(Z-Hexadec-11-enyloxy)-N,N-dimethylamino propane[3] (0.100 g, 0.17 mmol) and 11-bromo-3,6,9-trioxoundecan-1-ol[2] (0.050 g, 0.20 mmol) in methanol (1 ml) were stirred in a sealed tube at 90° C. for 24 h. The solvent was removed in vacuo and the product purified by flash chromatography on silica (10% methanol in dichloromethane) to give the titled compound (0.060 g, 43%) as a pale yellow oil. $v_{max}$ (neat)/cm$^{-1}$: 3385 s, 3005 m, 2924 s, 2853 s, 1634 m, 1466 s, 1350 m, 1119 s; $\delta_H$ (300 MHz; CDCl$_3$) 0.87 (6H, m, 2×CH$_3$CH$_2$) 1.15-1.42 (36H, m), 1.53 (4H, m, 2×OCH$_2$CH$_2$), 2.00 (8H, m, 2×CH$_2$CH=CHCH$_2$), 2.29 (1H, s, br, OH), 3.43 (6H, s, $^{30}$N(CH$_3$)$_2$), 3.48-4.25 (25H, m, CH$_2$CHOCH$_2$, CH$_2$OCH$_2$, PEG-OCH$_2$CH$_2$O), 5.32 (4H, m, 2×CH=CH); $\delta_C$ (75.4 MHz; CDCl$_3$) 14.0 (CH$_3$CH$_2$), 22.3, 26.1, 26.2, 26.9, 27.2, 29.3-30.0 (signal overlap), 32.0, 53.0 and 53.6 (N$^+$(CH$_3$)$_2$), 61.2, 65.2, 66.6, 68.6, 69.2, 70.1-70.5 (signal overlap), 129.9 (CH=CH), 130.3 (CH=CH); m/z (ES+) 740.71 ({M-Br}$^+$, 100%).

EXAMPLE 7

{2,3-Di-[(Z)-hexadec-11-enyloxy]-propyl}-N-{2-[2-(2-{2-[2-(2-hydroxy-ethoxy)-ethoxy]-ethoxy}-ethoxy)-ethoxy]-ethyl}-N,N-dimethylammonium bromide

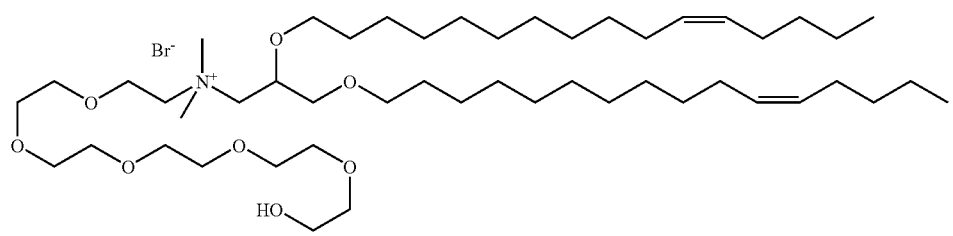

1,2-(Z-Hexadec-11-enyloxy)-N,N-dimethylamino propane[3] (0.100 g, 0.17 mmol) and 17-bromo-3,6,9,12,15-pentaoxoheptadecan-1-ol[2] (0.070 g, 0.20 mmol) in methanol (1 ml) were stirred in a sealed tube at 90° C. for 24 h. The solvent was removed in vacuo and the product purified by flash chromatography on silica (10% methanol in dichloromethane) to give the titled compound (0.07 g, 44%) as a pale yellow oil. $v_{max}$ (neat)/cm$^{-1}$: 3400 s, 3005 m, 2924 s, 2853 s, 1634 m, 1466 s, 1352 m, 1115 s; $\delta_H$ (300 MHz; CDCl$_3$) 0.83 (6H, m, 2×CH$_3$CH$_2$) 1.15-1.40 (36H, m), 1.49 (4H, m, 2×OCH$_2$CH$_2$), 1.96 (8H, m, 2×CH$_2$CH=CHCH$_2$), 2.87 (1H, s, br, OH), 3.46 (6H, s, $^+$N(CH$_3$)$_2$), 3.47-4.10 (33H, m, CH$_2$CHOCH$_2$, CH$_2$OCH$_2$, PEG-OCH$_2$CH$_2$O), 5.30 (4H, m, 2×CH=CH); $\delta_C$ (75.4 MHz; CDCl$_3$) 14.0 (CH$_3$CH$_2$), 22.3, 26.0, 26.2, 26.9, 27.2, 29.2-30.0 (signal overlap), 31.9, 32.2, 32.6, 53.2 (N$^+$(CH$_3$)$_2$), 61.1, 64.8, 65.0, 65.6, 68.7, 69.2, 69.9-70.4 (signal overlap), 71.9, 72.6, 73.4, 129.8 (CH=CH), 130.3 (CH=CH); m/z (ES+) 829.14 ({M-Br}$^+$, 100%).

EXAMPLE 8

Synthesis of Fmoc-Haa4

A reaction scheme for the production of the protected amino acid Fmoc-Haa4 is as follows:

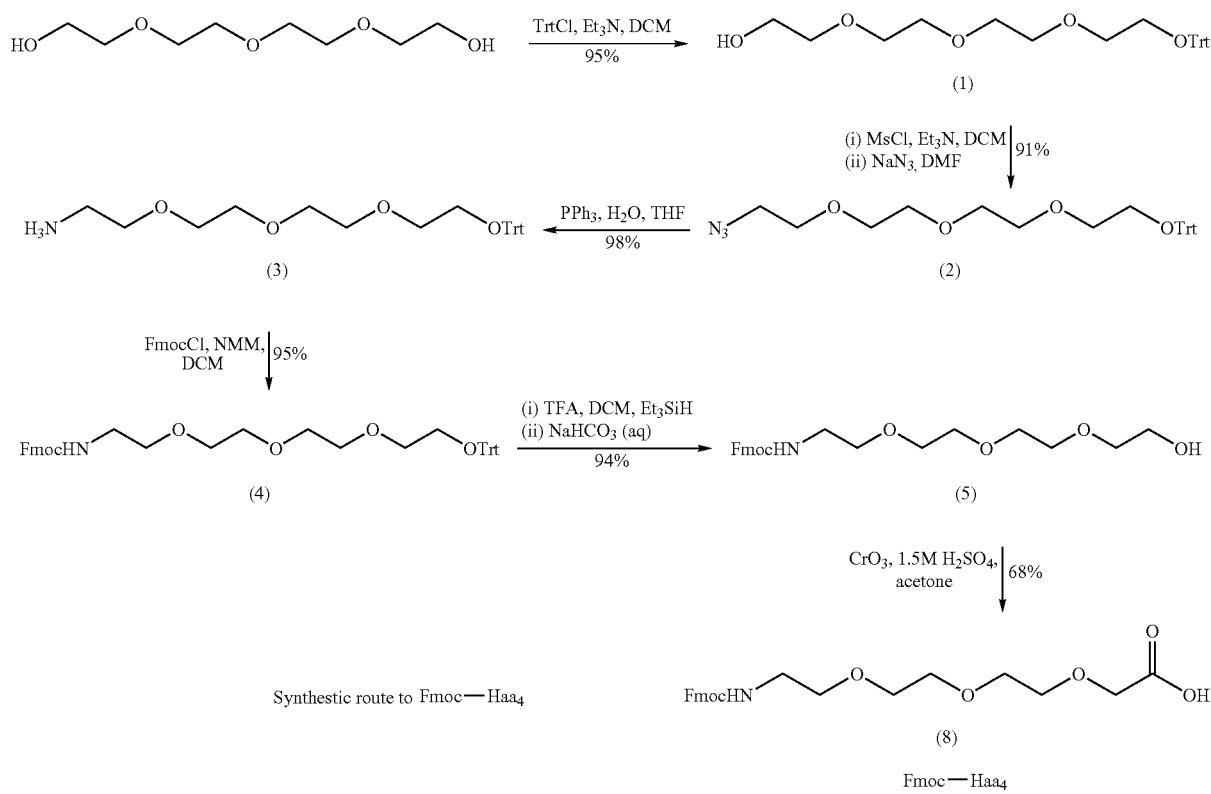

Synthestic route to Fmoc—Haa₄

This scheme will flow be described in more detail. The compound numbers shown in parentheses in the following description correspond to the numbers on the scheme shown above.

EXAMPLE 8.1

11-Triphenylmethyloxy-3,6,9-trioxaundecan-1-ol (1)

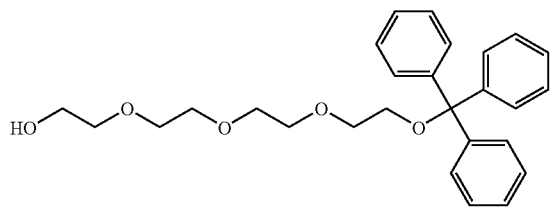

To tetraethylene glycol (213.65 g, 1.1 mol) and triethylamine (20.24 g, 27.8 ml, 200 mmol) in dry dichloromethane (1500 ml) was added dropwise triphenylmethyl chloride (27.88 g, 100 mmol) in dry dichloromethane (500 ml). This solution was left to stir under argon at room temperature for 24 hours. After 24 hours, the reaction was concentrated in vacuo to give a mixture of product and starting material as a yellow oil. This oil was then re-dissolved in dichloromethane (1000 ml), partitioned with sat. aq. NaHCO₃ (500 ml), water (3×400 ml) and finally sat. aq. NaCl (500 ml). The organic layer was separated, dried over anhydrous sodium sulphate and concentrated in vacuo to give the title compound as a yellow oil (42.2 g, 95%) which was used without further purification.

$^1$H NMR (CD$_3$CN) δ: 2.75 (1H, bs, (C$_6$H$_5$)$_3$COCH$_2$ (CH$_2$OCH$_2$)$_3$CH$_2$OH) 3.16 (2H, t, J=5.09 Hz, (C$_6$H$_5$)$_3$COCH$_2$(CH$_2$OCH$_2$)$_3$CH$_2$OH), 3.47-3.63 (14H, m, (C$_6$H$_5$)$_3$COCH$_2$(CH$_2$OCH$_2$)$_3$CH$_2$OH), 7.25-7.49 (15H, m, (C$_6$H$_5$)$_3$COCH$_2$(CH$_2$OCH$_2$)$_3$CH$_2$OH). $^{13}$C NMR (CD$_3$CN) δ: 60.76 (1C, C1), 63.17 (1C, C11), 69.87, 69.91, 70.02, 70.04, 70.20, 72.07 (6C, C2-C10), 86.14 (1C, —OC(C$_6$H$_5$)$_3$), 126.77, 127.54, 128.31, 144.03 (18C, —OC(C$_6$H$_5$)$_3$). IR ν/cm$^{-1}$ (NaCl): 3440 (vst., O—H stretch), 3057 (wk., Aryl-H stretch), 2872 (st., C—H stretch), 1597 (wk., C═C aromatic stretch), 1489, 1448 (med., O—H bend or aromatic), 1080 (vst., C—O stretch).

EXAMPLE 8.2

11-Triphenylmethyloxy-1-azido-3,6,9-trioxaundecane (2)

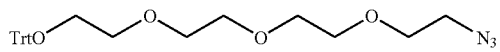

To 11-triphenylmethyloxy-3,6,9-trioxaundecan-1-ol (1) (21.82 g, 50 mmol) and triethylamine (15.33 ml, 11.13 g, 110 mmol, 2.2 eq.) in dry dichloromethane (150 ml), under argon at 0° C. was added dropwise methanesulfonyl chloride (7.74 ml, 11.45 g, 100 mmol, 2 eq.) in dry dichloromethane (50 ml). Once addition was complete, the reaction was left to stir for three hours at room temperature. Dichloromethane (200 ml) was then added and the organic solution was partitioned with sat. aq. NaHCO$_3$ (2×200 ml). The organic phase was then partitioned with sat. aq. NaCl (200 ml), dried over anhydrous sodium sulphate and concentrated in vacuo to give a brown oil. This oil was azeotroped several times with toluene to remove water.

The brown oil war, dissolved in dimethylformamide (150 ml) and sodium azide (13.0 g, 200 mmol) was added. The reaction was left to stir for four days after which time it was concentrated in vacuo and then dissolved in dichloromethane (250 ml). This organic solution was partitioned with water (2×150 ml) followed by sat. aq. NaCl (200 ml), dried over anhydrous sodium sulphate and concentrated in vacuo to yield a dark brown oil. The product was isolated from this oil by N.P.S.G. chromatography, eluting initially with chloroform/hexane (1:1), then gradually changing to chloroform only to yield the title compound (21.0 g, 91%) as a yellow oil.

$^1$H NMR (CDCl$_3$) δ: 3.25 (2H, t, J=5.11 Hz, (C$_6$H$_5$)$_3$COCH$_2$(CH$_2$OCH$_2$)$_3$CH$_2$N$_3$) 3.34 (2H, 1, J=4.81 Hz, (C$_6$H$_5$)$_3$COCH$_2$(CH$_2$OCH$_2$)$_3$CH$_2$N$_3$) 3.63-3.69 (12H, m, (C$_6$H$_5$)$_3$COCH$_2$(CH$_2$OCH$_2$)$_3$CH$_2$N$_3$), 7.20-7.48 (15H, m, (C$_6$H$_5$)$_3$COCH$_2$(CH$_2$OCH$_2$)$_3$CH$_2$N$_5$, $^{13}$C NMR (CDCl$_3$) δ: 51.10 (1C, C1), 63.78 (1C, C11), 70.42, 71.10, 71.16, 71.22 (6C, C2-C10), 86.98 (1C, —OC(C$_6$H$_5$)$_3$), 127.32, 128.15, 129.15. 144.57 (18C, —OC(C$_6$H$_5$)$_3$). IR v/cm$^{-1}$ (NaCl): 3059 (wk., Aryl-H stretch), 2870 (st., C—H stretch), 2108 (vst., —N$_3$ stretch), 1597 (wk., C=C aromatic stretch), 1489, 1448 (med., aromatic), 1092 (vst., C—O stretch). MS m/z (+ve Ion FAB): 484 (M+Na$^+$, 98%), 243 ([(C$_6$H$_5$)$_3$C]$^+$, 63%). HRMS (+ve ion FAB): Measured mass −484.2203. Actual mass for M+Na$^+$ −484.2212.

EXAMPLE 8.3

11-Triphenylmethyloxy-1-amino-3,6,9-trioxaundecane (3)

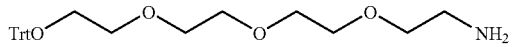

To 11-triphenylmethyloxy-1-azido-3,6,9-trioxaundecane (2) (21.0 g. 45.5 mmol) in tetrahydrofuran (100 ml) was added triphenylphosphinc (14.33 g, 54.6 mmol, 1.2 eq.). After two hours water (3 ml) was added to the reaction. The reaction was then left to stir under argon at room temperature for 24 hours after which time it was concentrated in vacuo. To the remaining oil/solid was added diethyl ether (65 ml) and the reaction mixture was then filtered and concentrated in vacuo. The product was isolated by N.P.S.G. chromatography, eluting initially with a large volume of chloroform and then changing to chloroform/methanol/triethylamine (85:10:5) to yield 19.0 g (96%) of a pale yellow oil.

$^1$H NMR (CDCl$_3$) δ: 2.83 (2H, t, J=5.21 Hz, (C$_6$H$_5$)$_3$COCH$_2$(CH$_2$OCH$_2$)$_3$CH$_2$NH$_2$) 3.25 (2H, t, J=5.18 Hz, (C$_6$H)$_3$COCH$_2$(CH$_2$OCH$_2$)$_3$CH$_2$NH$_2$), 3.50 (2H, t, J=5.21 Hz, (C$_6$H$_5$)$_3$CO(CH$_2$OCH$_2$)$_3$CH$_2$CH$_2$NH$_2$), 3.61-3.69 (10H, m, (C$_6$H$_5$)$_3$COCH$_2$(CH$_2$OCH$_2$)$_2$CH$_2$OCH$_2$CH$_2$NH$_2$), 7.19-7.49 (15H, m, (C$_6$H$_5$)$_3$COCH$_2$(CH$_2$OCH$_2$)$_3$CH$_2$NH$_2$). $^{13}$C NMR (CDCl$_3$) δ: 42.15 (1C, C1), 63.79 (1C, C11), 70.75, 71.09, 71.11, 71.14, 71.22, 73.71 (6C, C2-C10), 87.00 (1C, —OC(C$_6$H$_5$)$_3$), 127.32, 128.15, 129.15, 144.55 (18C, —OC(C$_6$H$_5$)$_3$). IR v/cm$^{-1}$ (NaCl): 3380 (wk., N—H stretch), 3060 (wk., Aryl-H stretch), 2870 (st., C—H stretch), 1600 (wk., C=C aromatic stretch), 1490, 1450 (med., aromatic), 1100 (vst., C—O s MS m/z (+ve Ion FAB): 436 (M+H$^+$, 14%), 243 ([(C$_6$H$_5$)$_3$C]$^+$, 99%). HRMS (+ve ion FAB): Measured mass −436.2483. Actual mass for M+H$^+$ −436.2487.

EXAMPLE 8.4

11-Triphenylmethyloxy-1-(9-fluorenylmethyloxycarbonylamido)-3,6,9-trioxaundecane (4)

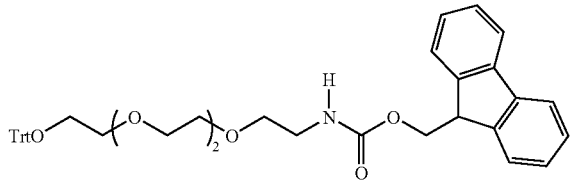

To 11-triphenylmethyloxy-1-amino-3,6,9-trioxaundecane (3) (8.7 g, 20 mmol) and N-methylmorpholine (4.4 ml, 4.05 g, 40 mmol) under argon, at 0° C. in dry dichloromethane (100 ml) was added dropwise 9-fluorenylmethyl chloroformate (9.03 g, 35 mmol, 1.5 eq.) in dry dichloromethane (40 ml). Once addition was complete, the reaction was left to stir at room temperature for 24 hours. Dichloromethane (100 ml) was added and the resulting solution was partitioned with citric acid solution (pH 6, 150 ml). The organic phase was then partitioned with sat. aq. NaCl (200 ml), dried over anhydrous sodium sulphate and concentrate in vacuo. The product was isolated by N.P.S.G. chromatography, eluting with chloroform only to yield 12.93 g (95%) of a viscous yellow oil.

$^1$H NMR (CDCl$_3$) δ: 3.25 (2H, t, J=5.16 Hz, (C$_6$H$_5$)$_3$COCH$_2$(CH$_2$OCH$_2$)$_3$CH$_2$NHCO$_2$CH$_2$C$_{13}$H$_9$), 3.36 (2H, q, J=4.5 Hz, (C$_6$H$_5$)$_3$COCH$_2$(CH$_2$OCH$_2$)$_3$CH$_2$NHFmoc), 3.55-3.68 (12H, m, (C$_6$H$_5$)$_3$COCH$_2$(CH$_2$OCH$_2$)$_3$CH$_2$Nmoc), 4.21 (1H, t, J=6.7 Hz, Fmoc H9), 4.40 (2H, d, J=6.7 Hz, Fmoc H), 5.40 (1H, bs, —NH—), 7.22-7.49 (15H, m, Fmoc & trityl), 7.59 (2H, d, Fmoc H4 & H5), 7.77 (2H, d, J=7.40 Hz, Fmoc H1 & H8). $^{13}$C NMR (CDCl$_3$) δ: 41.38 (1C, C1), 47.74 (1C, Fmoc C9), 63.77 (1C, C11), 66.99 (1C, Fmoc —CH$_2$—), 70.46, 70.82, 71.07, 71.12, 71.24 (6C, C2-C10), 87.01 (1C, —OC(CH$_6$H$_5$)$_3$), 120.34, 125.49, 127.44, 128.05 (8C, Fmoc C1-C8), 127.35, 128.16, 129.16 (15C, trityl), 141.74, 144.47 (4C, Fmoc C4a, C4b, C8a & C9a), 144.56 (3C, trityl), 156.92 (1C, carbamate C=O). IR v/cm$^{-1}$ (NaCl): 3350 (med., N—H stretch), 3060 (wk., Aryl-H stretch), 2860 (st., C—H stretch), 1700 (st., carbamate C=O stretch), 1570-1460 (med., carbamate N—H bend & C—C aromatic stretch), 1100 (st. C—O stretch). MS m/z (+ve ESI): 697 (M+K$^+$, 19%), 681 (M+Na$^+$, 99%). HRMS (+ve ESI): Measured mass −680.29881. Actual mass for M+Na$^+$ −680.29826.

EXAMPLE 8.5

11-(9-Fluorenylmethyloxycarbonylamido)-3,6,9-trioxaundecan-1-ol (5)

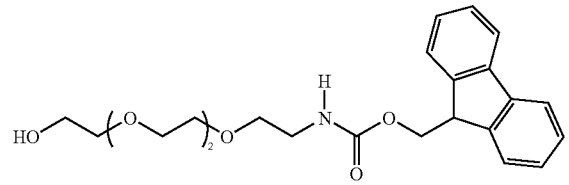

11-Triphenylmethyloxy-1-(9-fluorenylmethyloxycarbonylamido)-3,6,9-trioxaundecane (4) (12.93 g, 19 mmol) was dissolved in a solution of dichloromethane, trifluoroacetic acid and triethylsilane (100 ml, 8:1:1). The reaction was left to stir at room temperature under argon for one hour. Water (100 ml) was then added to the reaction and the resulting mixture was adjusted to pH 7 with sat aq. NaHCO$_3$ whilst being vigorously stirred. The two layers were separated and the aqueous solution was partitioned with another volume of dichloromethane (100 ml). The organic fractions were combined, dried over anhydrous sodium sulphate and concentrated in vacuo. The product was isolated by N.P.S.G. chromatography, eluting initially with a large volume of chloroform and then gradually changing the eluent to ethyl acetate only to yield 7.56 g (94%) of a yellow oil.

$^1$H NMR (CDCl$_3$) δ: 3.40 (2H, bs, HOC$\underline{H}_2$(CH$_2$OCH$_2$)$_3$C$\underline{H}_2$NHFmoc), 3.57-3.74 (14H, m, HOC$\underline{H}_2$(C$\underline{H}_2$OC$\underline{H}_2$)$_3$CH$_2$NHFmoc), 4.21 (1H, t, J=6.6 Hz, Fmoc H9), 4.42 (2H, d, J=6.6 Hz, Fmoc H), 4.76, 6.06 (1H & 1H, bs, —N$\underline{H}$— & —O$\underline{H}$), 7.30 (2H, t, J=7.4 Hz, *H3 and *H6), 7.39 (2H, t, J=7.4 Hz, *H2 and *H7), 7.61 (2H, d, J=7.4 Hz, *H4 and *H5), 7.76 (2H, d, J=7.4 z, *H1 and *H8). $^{13}$C NMR (CDCl$_3$) δ: 41.43 (1C, C11), 47.76 (1C, Fmoc C9), 61.72 (1C, C1), 67.08 (1C, Fmoc —$\underline{C}$H$_2$—), 70.10, 70.37, 71.50, 71.26, 72.46 (6C, C2-C10), 120.18, 125.371 127.35, 127.94 (8C, Fmoc C1-C8), 141.61, 144.27 (4C, Fmoc C4a, C4b, C8a & C9a), 157.64 (1C, carbamate C═O). IR v/cm$^{-1}$ (NaCl): 3324 (st., N—H & O—H stretch), 3067, 3041, 3020 (wk., Aryl-H stretch), 2882 (st., C—H stretch). 1672 (st., carbamate C═O stretch), 1535 (med., carbamate N—H bend), 1451 (st., C═C aromatic stretch), 1100 (st., C—O stretch). MS m/z (+ve Ion FAB): 454 (M+K$^+$, 92%), 438 (M+Na$^+$, 99%), 179 ([C$_{14}$H$_{11}$]$^+$, 34%). HRMS (+ve ion FAB): Measured mass −438.1886. Actual mass for M+Na$^+$ −438.1893.

EXAMPLE 8.6

11-(9-Fluorenylmethyloxycarbonylamido)-3,6,9-trioxaundecanoic acid (Fmoc-Haa4), (6)

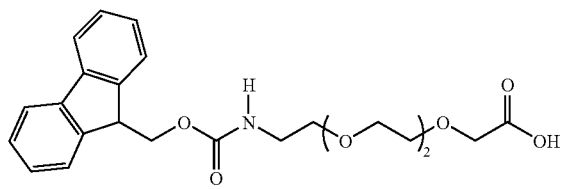

To vigorously stirring 11-(9-fluorenylmethyloxycarbonylamido)-3,6,9-trioxaundecan-1-ol (5) (4.15 g, 10 mmol) in acetone (100 ml) at 0° C. was very slowly added chromium trioxide (3.0 g, 30.0 mmol, 3 eq.) in sulphuric acid (1.5 M, 60.0 ml, 90 mmol, 9 eq.). Once addition was complete the reaction was left to warm to room temperature and to stir for 24 hours.

After 24 hours water (300 ml) was added to the reaction along with reverse phase silica gel (100 g). The reaction mixture was concentrated in vacuo until the volume had decreased by approximately one quarter and more water (100 ml) was added. The reaction mixture was once again concentrated in vacuo until no acetone could be detected to be present in the mixture. The mixture was then filtered to recover the R.P. silica gel, which was washed with copious amounts of water until the silica gel was almost colourless. The R.P. silica gel was then washed with acetonitrile (4×200 ml) and chloroform (3×150 ml). The organic fractions were combined and concentrated in vacuo to give a pale green oil. The product was isolated by N.P.S.G. chromatography, eluting initially with chloroform only, then gradually changing to chloroform/methanol (95:5) and finally gradually changing to chloroform/methanol/acetic acid (80:5:5) to yield 2.93 g (68.2%) of a yellow oil.

$^1$H NMR (CDCl$_3$) δ: 3.39 (2H, m, HO$_2$C(CH$_2$OCH$_2$)$_3$C$\underline{H}_2$NHFmoc), 3.54-3.71 (10H, m, HO$_2$CCH$_2$OC$\underline{H}_2$(C$\underline{H}_2$OC$\underline{H}_2$)$_2$CH$_2$NHFmoc) 4.12 (2H, s, HO$_2$CC$\underline{H}_{22}$(OCH$_2$CH$_2$)$_3$NHFmoc), 4.21 (1H, t, J=6.7 Hz, *H9), 4.39 (2H, d, J=6.7 Hz, HO$_2$C(CH$_2$OCH$_2$)$_3$CH$_2$NHCOC$\underline{H}_2$), 5.70 (1H, bs, —N$\underline{H}$—), 7.30 (2H, t, J=7.4 Hz, *H3 & *H6), 7.38 (2H, t, J=7.4 Hz, *H2 & *H7), 7.59 (2H, d, J=7.4 Hz, *H4 & *H5), 7.74 (2H, d, J=7.4 Hz, *H1 & *H8). $^{13}$C NMR (CDCl$_3$) δ: 41.26 (1C, C11), 47.66 (1C, *C9), 67.09 (1C, —NHCO$\underline{C}$H$_2$C$_{13}$H$_9$), 69.08 (1C, C2), 70.44, 70.61, 70.84, 71.46 (16C, C2-C25), 120.32, 125.48, 127.45, 128.05 (8C, *C1, *C$_2$, *C3, *C4, *C5, *C6, *C7 and *C8), 141.70, 144.39 (4C, *C4a, *C4b, *C8a and *C9a), 157.26 (1C, carbamate C═O), 173.12 (1C, C═O). IR v/cm$^{-1}$ (NaCl): 3336 (st., carboxylic O—H stretch), 3060 (wk., Aryl-H stretch), 2880 (st., C—H stretch), 1715, 1700 (vst., carbamate C═O stretch & carboxylic acid C═O stretch), 1611 (st., carbamate N—H bend), 1450 (st, carboxylic O—H bend), 1251 (st., carbamate & carboxylic C—O stretch), 1106 (vst., C—O stretch). MS m/z (+ve ES): 452 (M+Na$^+$, 99%). 430 (M+H$^+$, 3%). HRMS (+ve ESI): Measured mass −452.16899. Actual mass for M+Na$^+$ −452.16797.

EXAMPLE 9

Synthesis of Fmoc-Haa7

A reaction scheme for the production of the protected amino acid Fmoc-Haa7 is as follows:

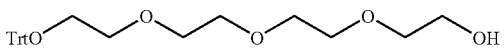

(1)

MaCl, Et$_3$N, DCM ↓

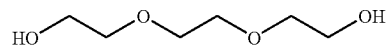

NaH, BnCl, $^n$Bu$_4$NBr, THF, rfx (99%) ↓

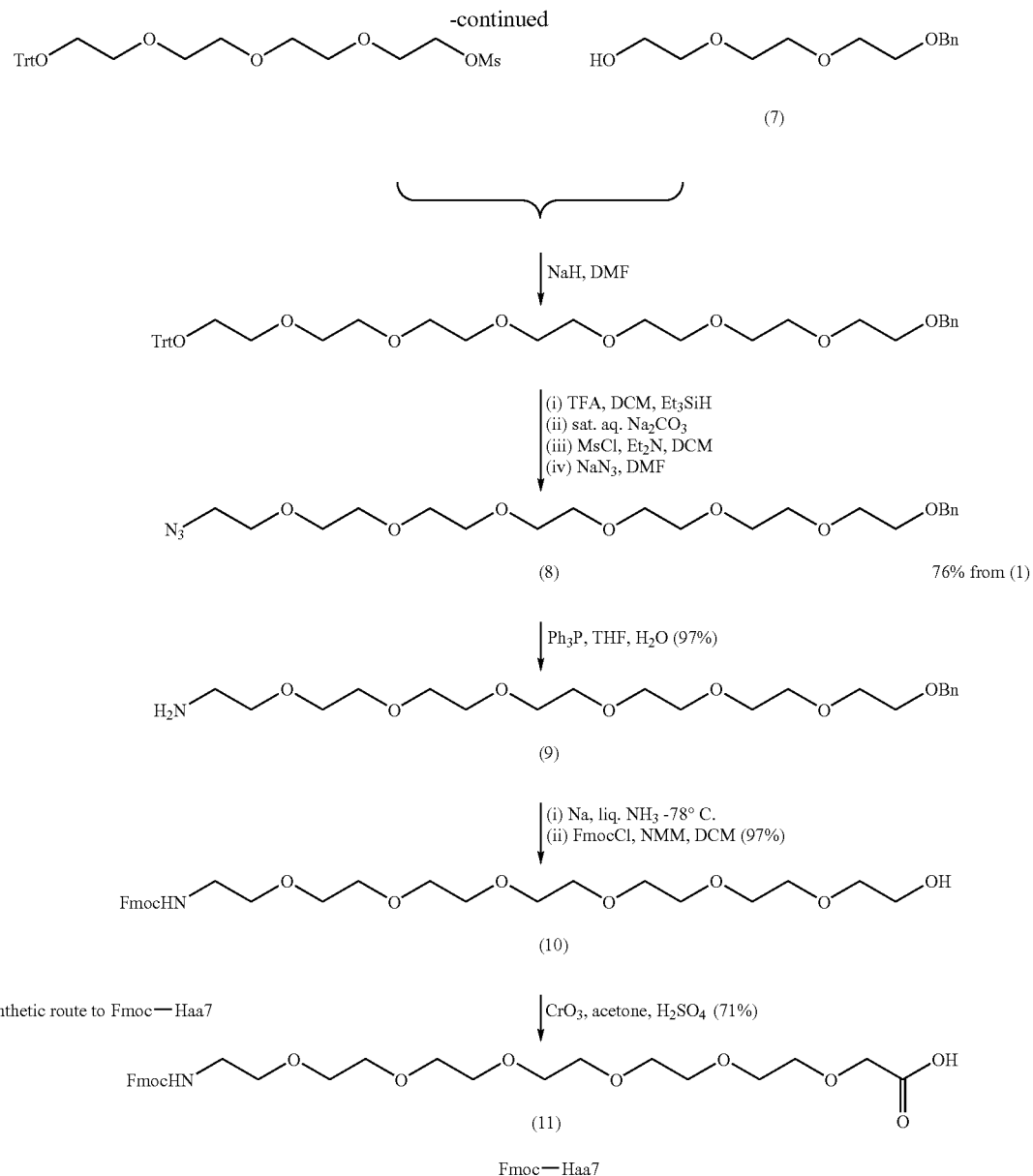

This scheme will now be described in more detail. The compound numbers shown in parentheses in the following description correspond to the numbers on the scheme shown above.

EXAMPLE 9.1

8-Phenylmethyloxy-3,6-dioxaoctan-1-ol (7)

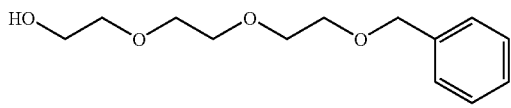

To triethylene glycol (30.0 g, 200 mmol) and tetrabutylammonium bromide (0.5 g, cat.) in dry tetrahydrofuran (150 ml) was added cautiously sodium hydride (1.20 g, 30 mmol, 60% w/w in mineral oil). After stirring for 20 minutes, benzyl chloride (2.53 s, 20 mmol) was added to the reaction and the reaction was heated to reflux under nitrogen for 24 hours. The reaction was then cooled to room temperature and concentrated in vacuo to give an oil. This oil was dissolved in dichloromethane (300 ml) and partitioned with sat. aq. NaCl (2×200 ml). The organic phase was dried over anhydrous sodium sulphate and concentrated in vacuo to give a yellow oil. This was purified by N.P.S.G. chromatography, eluting initially with chloroform and then gradually changing to chloroform/methanol (90:10), to yield 4.94 g (99%) of a pale yellow oil.

$^1$H NMR (CDCl$_3$) δ: 2.74 (1H, bt, C$_6$H$_5$CH$_2$OCH$_2$(CH$_2$OCH$_2$)$_2$CH$_2$OH), 3.60-3.70 (12H, m, C$_6$H$_5$CH$_2$OCH$_2$(CH$_2$OCH$_2$)$_2$CH$_2$OH), 4.57 (2H, s, C$_6$H$_5$CH$_2$OCH$_2$(CH$_2$OCH$_2$)$_2$CH$_2$OH), 7.25-7.35 (5H, m, C$_6$H$_5$CH$_2$OCH$_2$(CH$_2$OCH$_2$)$_2$CH$_2$OH.) $^{13}$C NMR (CDCl$_3$) δ:

62.1 (1C, C1), 69.82, 70.79, 71.01, 71.07 (4C, C4-C8), 72.94 (1C, C2), 73.65 (1C, —O$\underline{C}$H$_2$C$_5$H$_5$), 128.0, 128.13, 128.74, 138.61 (6C, benzyl). IR v/cm$^{-1}$ (NaCl): 3449 (st., O—H stretch), 3030 (wk., Aryl-H stretch), 2868 (st., C—H stretch). 1454 (wk., C—H deformation), 1350, 1294, 1248 (med., O—H bending), 1099 (vst., C—O stretch). MS m/z (+ve Ion FAB): 263 (M+Na$^+$, 4%), 241 (M+H$^+$, 99%), 91 ([C$_7$H$_7$]$^+$, 100%). HRMS (+ve ion FAB): Measured mass −241.1442. Actual mass for M+H$^+$ −241.1440.

EXAMPLE 9.2

20-Phenylmethyloxy-1-azido-3,6,9,12,15,18-hexaoxaeicosane (8)

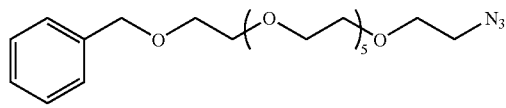

To 11-triphenylmethyloxy-3,6,9-trioxaundecan-1-ol (1) (43.65 g, 100 mmol) and triethylamine (30.66 ml, 22.26 g, 220 mmol, 2.2 eq.) in dry dichloromethane (250 ml), under argon at 0° C. was added dropwise methanesulfonyl chloride (15.48 ml, 22.91 g, 200 mmol, 2 eq.) in dry dichloromethane (100 ml). Once addition was complete, the reaction was left to stir for five hours at room temperature. A further volume of dichloromethane (250 ml) was then added to the reaction and the organic solution was partitioned with sat. aq. NaHCO$_3$ (2×300 ml). The organic phase was then partitioned with sat. aq. NaCl (400 ml), dried over anhydrous sodium sulphate and concentrated in vacuo to give a brown oil. This oil was azeotroped several times with toluene to remove water and then placed under high vacuum until the oil became an orange solid.

To the orange solid, under argon was added 8-phenylmethyloxy-3,6-dioxaoctan-1-ol (7) (28.34 g, 100 mmol) in dry dimethylformamide (200 ml) followed by sodium hydride (12.0 g, 300 mmol, 3 eq., 60% w/w in mineral oil). The reaction was left to stir for 5 days at room temperature. The reaction was then concentrated in vacuo and then re-dissolved in diethyl ether (1000 ml) and water (500 ml). The organic phase was then partitioned with aq. sat. NaCl with a little NaHCO$_3$ (500 ml), dried over anhydrous sodium sulphate and concentrated in vacuo to give a brown oil.

To this brown oil was added a solution made up of dichloromethane, triethylsilane and trifluoroacetic acid (300 ml, 80:10:10). The reaction was left to stir at room temperature for 2 hours. After one hour sat. aq. Na$_2$CO$_3$ was slowly added to the reaction with vigorous stirring until the reaction reached pH 12. The two layers were partitioned and the aqueous fraction was back-extracted several times with dichloromethane (9×100 ml). The organic fractions were combined, dried over anhydrous sodium sulphate and concentrated in vacuo to give a yellow solid/oil. This oil was re-dissolved in water (200 ml) and the aqueous solution was partitioned twice with hexane (2×200 ml). The aqueous solution was then concentrated in vacuo to give a pale yellow oil. The resulting oil was azeotroped with anhydrous acetonitrile several times.

To this oil and triethylamine (30.66 ml, 22.26 g, 220 mmol, 2.2 eq.) in dry dichloromethane (250 ml), under argon at 0° C. was added dropwise methanesulfonyl chloride (15.48 ml, 22.91 g, 200 mmol, 2 eq.) in dry dichloromethane (75 ml). Once addition was complete, the reaction was left to stir for five hours at room temperature. After five hours another volume of dichloromethane (300 ml) was added to the reaction and the organic solution was partitioned with sat. aq. NaHCO$_3$ (2×300 ml). The organic phase was then partitioned with sat. aq. NaCl (300 ml), dried over anhydrous sodium sulphate and concentrated in vacuo to give a brown oil. This oil was azeotroped several times with toluene to remove water.

The brown oil was dissolved in dimethylformamide (150 ml) and sodium azide (32.51 g, 500 mmol, 5 eq.) was added. The reaction was left to stir for four days after which time it was concentrated in vacuo and then re-dissolved in diethyl ether (1000 ml). The ethereal solution was filtered and the filtrate was concentrated in vacuo to give a brown oil. This oil was purified by N.P.S.G. chromatography, eluting with diethyl ether only to yield the title compound (8) as a yellow oil (33.39 g, 75.6% from (1)).

$^1$H NMR (CDCl$_3$) δ: 3.37 (2H, t, J=5.1 Hz, C$_5$H$_5$CH$_2$O (CH$_2$CH$_2$O)$_6$CH$_2$C$\underline{H}$$_2$N$_3$), 3.60-3.69 (26H, m, C$_6$H$_5$CH$_2$O(C$\underline{H}$$_2$C$\underline{H}$$_2$O)$_6$CH$_2$CH$_2$N$_3$), 4.56 (2H, s, C$_6$H$_5$C$\underline{H}$$_2$O(CH$_2$CH$_2$O)$_6$CH$_2$CH$_2$N$_3$), 7.22-7.35 (5H, m, —OCH$_2$C$_6$$\underline{H}$$_5$). $^{13}$C NMR (CDCl$_3$) δ: 50.66 (1C, C1), 69.43, 70.03, 70.57, 70.59, 70.64, 70.68 (13C, C2-C20), 73.21 (1C, —O$\underline{C}$H$_2$C$_6$H$_5$), 127.58, 127.73, 128.35, 138.37 (7C, benzyl). IR v/cm$^{-1}$ (NaCl): 3010 (wk., Aryl-H stretch), 2867 (st., C—H stretch), 2106 (st., azide stretch), 1453 (med., C═C aromatic stretch), 1104 (vst., C═O stretch). MS m/z (+ve ES): 464 (M+Na$^+$, 99.9%), 436 ([C$_{21}$H$_{35}$O$_7$N]+Na$^+$, 4%). HRMS (+ve ion FAB): Measured mass −442.2566. Actual mass for M+H$^+$ −442.2553.

EXAMPLE 9.3

20-Phenylmethyloxy-3,6,9,12,15,18-hexaoxaeicosylamine (9)

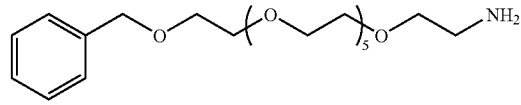

To 20-phenylmethyloxy-1-azido-3,6,9,12,15,18-hexaoxaeicosane (8) (32.70 g, 74.06 mmol) in tetahydrofuran (200 ml) was added triphenylphosphine (23.32 g, 88.88 mmol, 1.2 eq.). The solution was left to stir for 3 hours at room temperature before the addition of water (5.4 g, 296 mmol, 4 eq.). The reaction was then left to stir at room temperature for 48 hours.

After 48 hours the reaction was concentrated in vacuo and to the remaining oil was added water (500 ml). The reaction was then filtered to remove the precipitate, the precipitate being washed twice with water (2×150 ml). The filtrate was combined and acidified to pH 2 with concentrated hydrochloric acid. This solution was partitioned four times with diethyl ether (4×300 ml). The aqueous solution was then adjusted to pH 11 by addition of solid Na$_2$CO$_3$ and also saturated with NaCl. The resulting solution was partitioned four times with dichloromethane (4×300 ml). The organic fractions were combined, dried over anhydrous sodium sulphate and concentrated in vacuo to yield 29.77 g (96.8%) of a colourless oil, which required no further purification.

$^1$H NMR (DMSO) δ: 2.65 (2H, t, J=5.82 Hz, C$_6$H$_5$CH$_2$OCH$_2$(CH$_2$OCH$_2$)$_6$C$\underline{H}$$_2$NH$_2$), 3.36 (2H, t, J=5.82 Hz, C$_6$H$_5$CH$_2$O(CH$_2$CH$_2$O)$_6$C$\underline{H}$$_2$CH$_2$NH$_2$), 3.49-3.61 (24H, m, C$_6$H$_5$CH$_2$O(C$\underline{H}$$_2$C$\underline{H}$$_2$O)$_6$CH$_2$CH$_2$NH$_2$), 4.51 (2H, s, $C_6H_5C\underline{H}_2OCH_2(CH_2OCH_2)_6CH_2NH_2$), 7.27-7.39 (5H, m, $C_6\underline{H}_5CH_2OCH_2(CH_2OCH_2)_6CH_2NH_2$). $^{13}C$ NMR (DMSO) δ: 42.33 (1C, C1), 70.06, 70.52, 70.72 (12C, C4-C20), 72.96 (1C, C2), 74.08 (1C. —O$\underline{C}H_2C_6H_5$), 128.28, 128.40, 129.14, 139.42 (7C, benzyl). IR v/cm$^{-1}$ (NaCl): 3377, 3313 (wk., N—H stretch), 3086, 3062, 3028 (wk., Aryl-H stretch), 2865 (st., C—H stretch), 1959, 1886 (wk., aromatic overtones), 1583 (med., N—H bend), 1454 (med., C=C aromatic stretch), 1106 (vst., C—O stretch). MS m/z (+ve ES): 438 (M+Na$^+$, 12%), 416 (M+H$^+$, 99%). 524 ([$C_7H_7$]$^+$, 13%). HRMS (+ve ESI): Measured mass −416.26396. Actual mass for M+H$^+$ −416.26428.

EXAMPLE 9.4

20-(9-Fluorenylmethyloxycarbonylamido)-3,6,9,12,15,18-hexaoxaeicosan-1-ol (10)

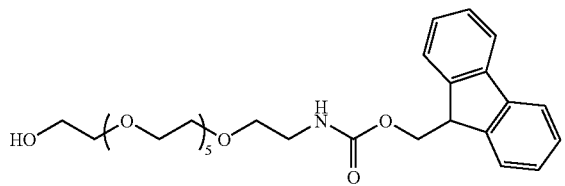

A solution of 20-pheylmethyloxy-1-amino-3,6,9,12,15,18-hexaoxaeicosane (9) (29.76 g, 71.6 mmol) in dry diethyl ether (200 ml) under argon was cooled to −78° C. Into this solution was condensed ammonia until the volume of the solution had almost doubled (c. 400 ml). To the solution under argon at −78° C. were added sodium pellets until a dark blue colour persisted. The reaction was allowed to warm to from −78° C. to −30° C. and then cooled back to −78° C. A saturated methanolic solution of ammonium chloride was slowly added to the reaction at −78° C. under argon until the solution was no longer blue in colour. The reaction was then allowed to warm to room temperature and once most of the ammonia had evaporated, the reaction was concentrated in vacuo. To the remaining residue was added water (400 ml) and the pH was adjusted to 4 with concentrated hydrochloric acid. The pH of the solution was then adjusted to 7 by addition of solid sodium hydrogen carbonate. Once the solution had been neutralized, sodium hydrogen carbonate (9.02 g, 107.4 mmol, 1.5 eq.) was again added, followed by dioxane (200 ml). This solution was cooled to 0° C. and fluorenylmethyl chloroformate (27.78 g, 107.4 mmol, 1.5 eq.) in dioxane (250 ml) was slowly added. Once addition was complete the reaction was allowed to warm to room temperature and left to stir for 24 hours.

After 24 hours the solution was acidified to pH 6 by addition of solid citric acid and then concentrated in vacuo to remove dioxane. The remaining aqueous solution was partitioned three times with chloroform (3×350 ml). The organic fractions were combined, dried over anhydrous sodium sulphate and concentrated in vacuo to give a yellow oil. This oil was purified by N.P.S.G. chromatography, eluting initially with ethyl acetate only and then gradually changing to ethyl acetate/methanol (4:1) to yield 38.04 g (97.0%) of a yellow oil.

$^1H$ NMR (CDCl$_3$) δ: 2.88 (1H, bs, —O$\underline{H}$), 3.39 (2H, q, J=5.2 Hz, HOCH$_2$(CH$_2$OCH$_2$)$_6$C$\underline{H}_2$NHFmoc), 3.55-3.63 (34H, m, HOCH$_2$(C$\underline{H}_2$OC$\underline{H}_2$)$_6$CH$_2$NHFmoc), 3.70 (2H, m, HOC$\underline{H}_2$(CH$_2$OCH$_2$)$_5$CH$_2$NHFmoc), 4.22 (1H, t, J=6.90 Hz, *H9), 4.41 (2H, d, J=6.90 Hz, HOCH$_2$(CH$_2$OCH$_2$)$_6$CH$_2$NHCOC$\underline{H}_2$), 5.57 (1H, t, J=5.2 Hz, N$\underline{H}$), 7.31 (2H, t, J=7.4 Hz, *H3 & *H6), 7.39 (2H, t, J=7.4 Hz, *H2 & *H7), 7.61 (2H, d, J=7.4 Hz, *H4 & *H5), 7.76 (2H, d, J=7.4 Hz, *H1 & *H8). $^{13}C$ NMR (CDCl$_3$) δ: 40.95 (1C, C20), 47.30 (1C, *C9), 61.71 (1C, C1), 66.54 (1C, —NHCO$\underline{C}H_2C_{13}H_9$), 70.09, 70.34, 70.57 (11C, C4-C19), 72.56 (1C, C2), 119.96, 125.10, 127.06, 127.65 (8C, *C1, *C2, *C3, *C4, *C5, *C6, *C7 and *C8), 141.32, 144.04 (4C, *C4a, *C4b, *C8a and *C9a), 156.59 (1C, carbamate C—O). IR v/cm$^{-1}$ (NaCl): 3326 (st., O—H & N—H stretch), 3041, 3020 (wk., Aryl-H stretch), 2884 (st. C—H stretch), 1672 (vst., carbamate C=O stretch & N—H bend), 1452 (med., C=C aromatic stretch), 1346 (med., carbamate C—O stretch), 1105 (vst., C—O stretch). MS m/z (eve ES): 548 (M+H$^+$, 9%), 178 ([$C_{14}H_{11}$]$^+$, 35%). HRMS (FAB, NOBA matrix): Measured mass −548.2868. Actual mass for M+H$^+$ −548.2859.

EXAMPLE 9.5

20-(9-Fluorenylmethyloxycarbonylamido)-3,6,9,12,15,18-hexaoxaeicosanoic acid (Fmoc-Haa7), (11)

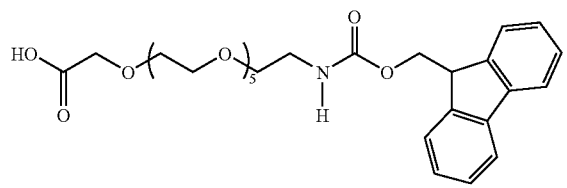

To vigorously stirring 20-(9-fluoranylmethyloxycarbonylamido)-3,6,9,12,15,18-hexaoxaeicosan-1-ol (10) (19.17 g, 35.0 mmol) in acetone (500 ml) at 0° C. was very slowly added chromium trioxide (10.50 g, 105 mmol, 3 eq.) in sulphuric acid (1.5 M, 210 ml, 315 mmol, 9 eq.). Once addition was complete the reaction was left to warm to room temperature and to stir for 24 hours.

After 24 hours water (1000 ml) was added to the reaction along with reverse phase silica gel (250 g). The reaction mixture was concentrated in vacuo until the volume had decreased by approximately one quarter and more water (500 ml) was added. The reaction mixture was once again concentrated in vacuo until no acetone could be detected to be present in the mixture. The mixture was then filtered to recover the R.P. silica gel which was washed with copious amounts of water until the silica gel was almost colourless. The R.P. silica gel was then washed with acetonitrile (4×400 ml) and chloroform (3×300 ml). The organic fractions were combined and concentrated in vacuo to give a green oil. This oil was purified by N.P.S.G. chromatography, eluting initially with chloroform only, then gradually changing to chloroform/methanol (95:5) and finally gradually changing to chloroform/methanol/acetic acid (85:10:5) to yield 14.2 g (71.0%) of a yellow oil.

$^1H$ NMR (CDCl$_3$) δ: 3.38 (2H, m, FmocHNC$\underline{H}_2$(CH$_2$OCH$_2$)$_6$CO$_2$H), 3.59-3.62 (22H, m, FmocHNCH$_2$(C$\underline{H}_2$OCH$_2$)$_5$C$\underline{H}_2$OCH$_2$CO$_2$H), 4.04 (2H, s, FmocHNCH$_2$(CH$_2$OCH$_2$)$_5$CH$_2$OC$\underline{H}_2$CO$_2$H), 4.22 (1H, t, J=6.7 Hz, *H9), 4.42 (2H, d, J=6.7 Hz, —NHCOOC$\underline{H}_2$), 5.73 (1H, bs, —N$\underline{H}$—), 7.31 (2H, t, J=7.4 Hz, *H3 and *H6), 7.41 (2H, t, J=7.4 Hz, *H2 and *H7), 7.61 (2H, d, J=7.4 Hz, *H4 and *H5), 7.77 (2H, d, J=7.4 Hz, *H1 and *H8). $^{13}C$ NMR (CDCl$_3$) δ: 47.49 (1C, *C9), 66.61 (1C, —NHCOO$\underline{C}H_2C_{13}H_9$), 69.98, 70.02, 70.12, 70.25 (12C, C2-C19), 120.12, 125.25, 127.25. 127.85 (8C, *C1, *C2, *C3, *C4, *C5, C6, *C7 and *C8), 141.50, 144.21 (4C, *C4a, *C4b, *C8a and *C9a), 156.85 (1C, carbamate C=O), 172.84 (1C, C1, C=O). IR ν/cm$^{-1}$ NaCl): 3333 (st., O—H & N—H stretch), 2871 (st., C—H stretch), 2550 (wk., O—H stretch), 1717 (st., acid C=O stretch), 1605 (st., carbamate C=O stretch), 1538 (med., carbamate N—H bend), 1450 (wk., C—H deformation), 1252 (st., carbamate C—O stretch)., 1109 (st., C—O stretch). MS m/z (+ve Ion FAB): 584 (M+Na$^+$, 57.5%), 562 (M+H$^+$, 2.3%), 179 ([C$_{14}$H$_{11}$]$^+$, 44.6%), 165 ([C$_{13}$H$_9$]$^+$, 5.5%), 23 (Na$^+$, 100%). MS m/z (+ve ES): 600 (M+K$^+$, 27%), 584 (M+Na$^+$, 99%), 362 ([C$_{14}$H$_{29}$O$_8$N]+Na$^+$, 3%), 340 ([C$_{14}$H$_{30}$O$_8$N]$^+$, 2%). HRMS (FAB, NOBA matrix): Measured mass −584.2495. Actual mass for M+Na$^+$ −584.2472.

EXAMPLE 10

Synthesis of Fmoc-Haa9

A reaction scheme for the production of the protected amino acid, Fmoc-Haa9, is as follows.

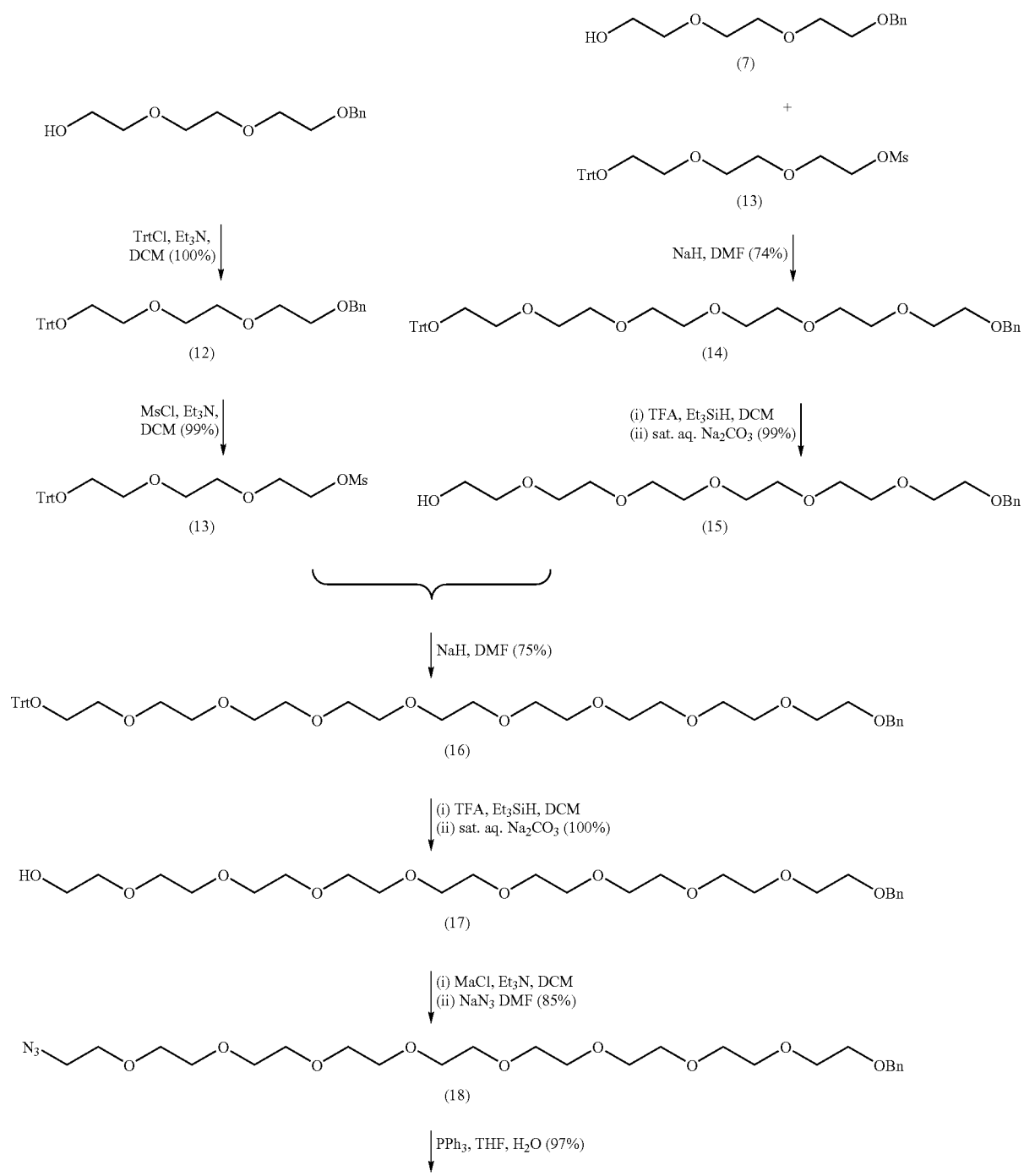

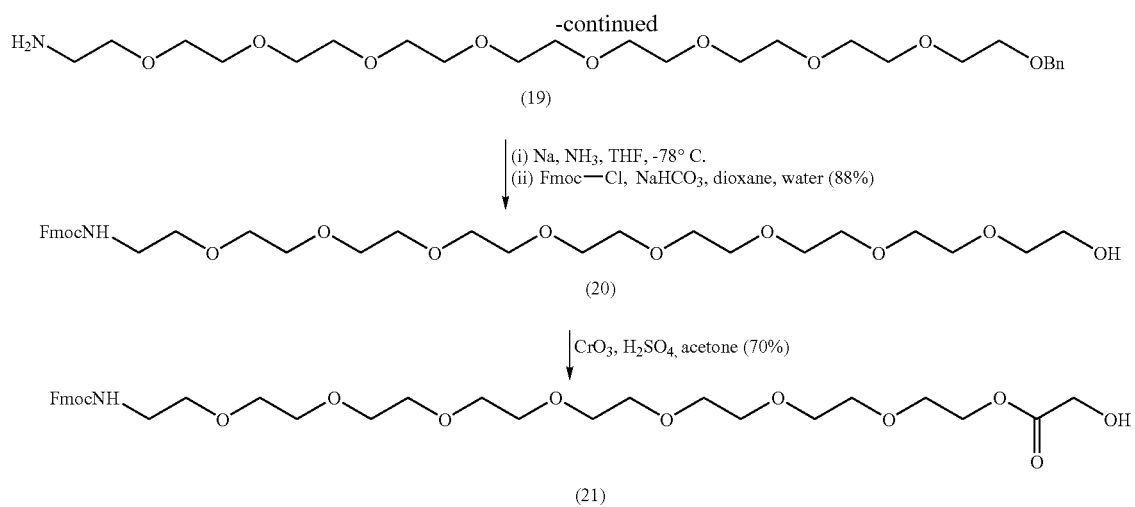

(19)

(i) Na, NH$_3$, THF, -78° C.
(ii) Fmoc—Cl, NaHCO$_3$, dioxane, water (88%)

(20)

CrO$_3$, H$_2$SO$_4$, acetone (70%)

(21)

Synthetic route to Fmoc—Haa9       Fmoc—Haa9

This scheme will now be described in more detail. The compound numbers shown in parentheses in the following description correspond to the numbers on the scheme shown above.

EXAMPLE 10.1

8-Triphenylmethyloxy-3-dioxaoctan-1-ol (12)

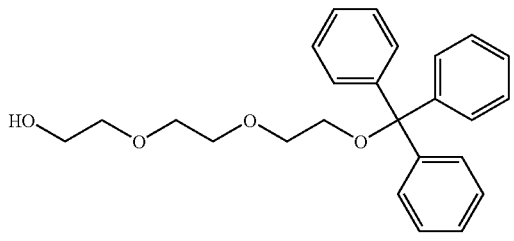

To triethylene glycol (90.10 g, 600 mmol) and triethylamine (6.07 g, 8.36 ml, 60 mmol) in dry dichloromethane (500 ml) was added dropwise triphenylmethyl chloride (6.07 g, 30 mmol) in dry dichloromethane (150 ml). This solution was left to stir under nitrogen at room temperature for 24 hours. The reaction was then concentrated in vacuo to give a mixture of product and starting material as a yellow oil. This oil was then redissolved in dichloromethane (400 ml), partitioned with sat. aq. NaHCO$_3$ (200 ml), water (4×250 ml) and finally sat. aq. NaCl (250 ml). The organic layer was separated, dried over anhydrous sodium sulphate and concentrated in vacuo to give a yellow oil. This oil was purified by N.P.S.G. chromatography, eluting initially with chloroform and then gradually changing to chloroform/methanol (98:2), to yield 12.04 g (100%) of a pale yellow oil.

$^1$H NMR (CDCl$_3$) δ: 2.35 (1H, bs. (C$_6$H$_5$)$_3$COCH$_2$ (CH$_2$OCH$_2$)$_2$CH$_2$OH), 3.25 (2H, t, J=5.09 Hz, (C$_6$H$_5$)$_3$COCH$_2$(CH$_2$OCH$_2$)$_2$CH$_2$OH), 3.58-3.71 (10H, m, (C$_6$H$_5$)$_3$COCH$_2$(CH$_2$OCH$_2$)$_2$CH$_2$OH), 7.18-7.47 (15H, m, (C$_6$H$_5$)$_3$COCH$_2$(CH$_2$OCH$_2$)$_2$CH$_2$OH). $^{13}$C NMR (CDCl$_3$) δ: 62.21 (1C, C1), 63.74 (1C, C$_8$), 70.95, 71.14, 71.24, 72.98 (4C, C2-C7), 87.08 (1C, —OC(C$_6$H$_5$)$_3$), 127.37, 128.18, 129.14, 144.52 (18C, —OC(C$_6$H$_5$)$_3$). IR ν/cm$^{-1}$ (NaCl): 3440 (vst., O—H stretch), 3057 (wk., Aryl-H stretch), 2872 (st., C—H stretch), 1597 (wk., C=C aromatic stretch), 1489, 1448 (med., O—H bend or aromatic), 1080 (vst., C—O stretch). MS m/z (+ve Ion FAB): 415 (M+Na$^+$, 25%). HRMS (+ve ion FAB): Measured mass –415.1876. Actual mass for M+Na$^+$ –415.1885.

EXAMPLE 10.2

8-Triphenylmethyloxy-3,6-dioxaoctyl methanesulfonate (13)

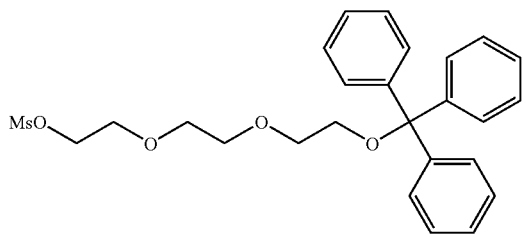

To 8-triphenylmethyloxy-3,6-dioxaoctan-1-ol (12) (12.0 g, 30 mmol) and triethylamine (9.1 g, 12.5 ml, 90 mmol) in dry dichloromethane (100 ml), under nitrogen, at 0° C. was slowly added methanesulphenyl chloride (5.80 ml, 8.59 g, 75 mmol, 2.5 eq.) in dry dichloromethane (40 ml). Once addition was complete, the reaction was left to warm to room temperature. After 2.5 hours, excess sat. aq. NaHCO$_3$ was added and the reaction was left to stir for 10 minutes. Additional dichloromethane (200 ml) was added, the aqueous and organic layers were separated and the organic solution was partitioned with sat. aq. NaCl (100 ml). The aqueous solution was back-extracted with dichloromethane (150 ml), the organic solutions were combined, dried over anhydrous sodium sulphate and concentrated in vacuo to give an orange oil. The oil was then azeotroped several times with dry toluene to remove water. This oil became a red solid (14.1 g, 99.8%) after several hours in high vacuo. The product was used without further purification.

¹H NMR (CDCl₃) δ: 2.94 (3H, s, CH₃SO₃CH₂CH₂O(CH₂)₂OCH₂CH₂OC(C₆H₅)₃), 3.25 (2H, t, J=5.11 Hz, CH₃SO₃CH₂CH₂O(CH₂)₂OCH₂CH₂OC(C₆H₅)₃), 3.64-3.76 (6H, m, CH₃SO₃CH₂CH₂O(CH₂)₂OCH₂CH₂OC(C₆H₅)₃), 3.78 (2H m, CH₃SO₃CH₂CH₂O(CH₂)₂OCH₂CH₂OC(C₆H₅)₃), 4.35 (2H, m, CH₃SO₃CH₂CH₂O(CH₂)₂OCH₂CH₂OC(C₆H₅)₃). ¹³C NMR (CDCl₂) δ: 38.03 (1C, —OSO₂CH₃), 63.76 (1C, C8), 69.50, 69.65 (2C, CH₃SO₃CH₂CH₂O(CH₂)₂OCH₂CH₂OC(C₆H₅)₃) 71.15, 71.2 (3C, CH₃SO₃CH₂CH₂O(CH₂)₂OCH₂CH₂OC(C₆H₅)₃) 87.04 (1C, —OC(C₆H₅)₃), 127.41, 128.19, 129.13, 144.49 (18C, —OC(C₆H₅)₃).

EXAMPLE 10.3

1-Triphenylmethyloxy-17-phenylmethyloxy-3,6,9,12,15-pentaoxaheptadecane (14)

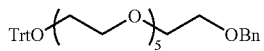

To 8-phenylmethyloxy-3,6-dioxaoctan-1-ol (7) (4.94 g, 20 mmol) and 8-triphenylmethyloxy-3,6-dioxaoctyl methanesulfonate (13) (9.88 g, 21 mmol) in dry dimethylformamide (50 ml) under argon was added sodium hydride (2.4 g, 60 mmol, 3 eq., 60% w/w in mineral oil). This solution was left to stir for 5 days at room temperature. The reaction was then concentrated in vacuo and then re-dissolved in diethyl ether (200 ml) and water (200 ml). The organic phase was then partitioned with aq. sat. NaCl with a little NaHCO₃ (200 ml), dried over anhydrous sodium sulphate and concentrated in vacuo to give a viscous dark brown oil. This oil was purified by N.P.S.G. chromatography, eluting initially with chloroform and then gradually changing to chloroform/methanol (98:2), to yield 9.11 g (74.1%) of an orange oil.

¹H NMR (CDCl₃) δ: 3.25 (2H, t, J=5.21 Hz, C₆H₅CH₂OCH₂(CH₂OCH₂)₅CH₂OC(C₆H₅)₃), 3.64-3.69 (22H, m, C₆H₅CH₂OCH₂(CH₂OCH₂)₅CH₂OC(C₆H₅)₃), 4.57 (2H, s, C₅H₅CH₂OCH₂(CH₂OCH₂)₅CH₂OC(C₆H₅)₃), 7.20-7.52 (20H, m, C₆H₅CH₂OCH₂(CH₂OCH₂)₅CH₂OC(C₆H₅)₃). ¹³C NMR (CDCl₃) δ: 63.78 (1C, C1), 69.91, 71.03, 71.07, 71.10, 71.21 (11C, C2-C17), 73.65 (1C, —OCH₂C₆H₄₅), 86.98 (1C, —OC(C₆H₅)₃), 127.31, 127.96, 128.12, 128.15, 128.74, 129.15 (20C, trityl & benzyl), 138.76 (1C, benzyl), 144.58 (3C, trityl). IR ν/cm⁻¹ (NaCl): 3030 (wk., Aryl-H stretch), 2869 (st., C—H stretch), 1600, 1570, 1480, 1450 (med., C=C aromatic stretch), 1109 (vst., C—O stretch). MS m/z (+ve Ion FAB): 637 (M+Na⁺, 0.6%), 613 ([C₃₈H₄₅O₇]⁺, 1.25%), 243 ([C₁₉H₁₅]⁺, 100%). HRMS (+ve ion FAB, NOBA matrix): Measured mass –637.3148. Actual mass for M+Na⁺ –637.3141.

EXAMPLE 10.4

17-Phenylmethyloxy-3,6,9,12,15-pentaoxaheptadecan-1-ol (15)

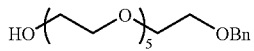

To 1-triphenylmethyloxy-17-phenylmethyloxy-3,6,9,12,15-pentaoxaheptadecane (14) (9.11 g, 14.82 mmol) was added a solution made up of dichloromethane, triethylsilane and trifluoroacetic acid (100 ml, 80:10:10). The reaction was left to stir at room temperature for 1 hour. Sat. aq. Na₂CO₃ was then slowly added to the reaction with vigorous stirring until the reaction reached pH 12. The two layers were partitioned and the aqueous fraction was back-extracted several times with dichloromethane (6×100 ml). The organic fractions were combined, dried over anhydrous sodium sulphate and concentrated in vacuo to give a yellow solid/oil. This oil was re-dissolved in water (100 ml) and the aqueous solution was partitioned twice with hexane (2×100 ml). The aqueous solution was then concentrated in vacuo to give a yellow oil. The resulting oil was azeotroped with anhydrous acetonitrile until 5.51 g (99%) of oil was recovered which required no further purification.

¹H NMR (CD₂Cl₂) δ: 3.62-3.79 (22H, m, C₆H₅CH₂OCH₂(CH₂OCH₂)₅CH₂OH), 4.60 (2H, s, C₆H₅CH₂OCH₂(CH₂OCH₂)₅CH₂OH), 7.29-7.38 (5H, m, C₆H₅CH₂OCH₂(CH₂OCH₂)₅CH₂OH). ¹³C NMR (CD₂Cl₂) δ: 60.90 (1C, C1), 69.13, 69.79, 69.82, 69.93, 70.10, 70.14, 70.24, 70.46 (10C, C4-C17), 72.08 (1C, C2), 73.86 (1C, –OCH₂C₆H₅), 127.57, 127.68, 128.30, 138.11 (6C, benzyl). IR ν/cm⁻¹ (NaCl): 3474 (st., O—H stretch), 3030 (wk., Aryl-H stretch), 2868 (st., C—H stretch), 1454, 1348 (med., O—H bond), 1109 (vst., C—O stretch). MS m/z (+ve Ion FAB): 395 (M+Na⁺, 5%), 373 ([C₁₉H₃₃O₇]⁺, 16%). HRMS (+ve ion FAB, NOBA matrix): Measured mass –395.2051. Actual mass for M+Na⁺ –395.2046.

EXAMPLE 10.5

1-Triphenylmethyloxy-26-phenylmethyloxy-3,6,9,12,15,18,21,24-octaoxahexaeicosane (16)

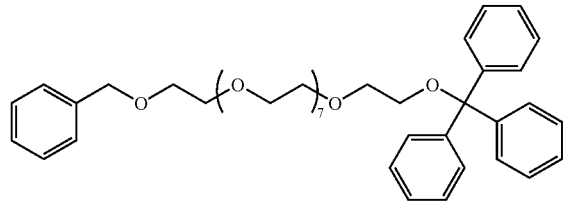

To 17-phenylmethyloxy-3,6,9,12,15-pentaoxaheptadecan-1-ol (15) (16.38 g, 43.9 mmol) in dry dimethylformamide (250 ml) was added 8-triphenylmethyloxy-3,6-dioxaoctyl methanesulfonate (13) (28.23 g, 60 mmol, 1.35 eq.) and sodium hydride (4.0 g, 100 mmol, 2.3 eq., 60% w/w in mineral oil). The reaction was left to stir for four days at room temperature after which time it was concentrated in vacuo. The reaction mixture was re-dissolved in diethyl ether (400 ml) and cooled in an ice bath to 0° C. Water was then slowly added until hydrogen was no longer evolved. The organic phase was ten partitioned twice with aq. sat. NaCl with a little NaHCO₃ (2×300 ml), dried over anhydrous sodium sulphate and concentrated in vacuo to give a viscous dark brown oil. The product was isolated by N.P.S.G. chromatography, eluting with ethyl acetate only to yield (16) as a yellow oil (24.2 g, 75.0%).

¹H NMR (CDCl₂) δ: 3.24 (2H, t, J=5.24 Hz, C₆H₅CH₂OCH₂(CH₂OCH₂)₈CH₂OC(C₆H₅)₃), 3.57-3.69 (34H, m, C₆H₅CH₂OCH₂(CH₂OCH₂)₈CH₂OC(C₆H₅)₃), 5.56 (2H, s, C₆H₅CH₂OCH₂(CH₂OCH₂)₈CH₂OC(C₆H₅)₃), 7.21-7.48 (20H, m, C₆H₅CH₂OCH₂(CH₂OCH₂)₈CH₂OC(C₆H₅)₃). ¹³C NMR (CDCl₃) δ: 63.38 (1C, C1), 69.51, 70.60, 70.67, 70.81 (17C, C2-C26), 73.24 (1C, —OCH$_2$C$_6$H$_5$), 86.57 (1C, —OC(C$_6$H$_5$)$_3$), 126.91, 127.56, 127.74, 128.39, 128.74 (20C, trityl & benzyl), 138.36 (1C, benzyl), 144.18 (3C, trityl). IR v/cm$^{-1}$ (NaCl): 3058, 3031 (wk., Aryl-H stretch), 2868 (st., C—H stretch), 1962 (wk., aromatic), 1596 (wk., aryl C—C stretch), 1489, 1449 (med., C=C aromatic stretch), 1105 (vst., C—O stretch). MS m/z (+ve Ion FAB): 769 (M+Na$^+$, 75%), 243 ([(C$_6$H$_5$)$_3$C]$^+$, 39%). HRMS (+ve ion FAB): Measured mass −769.39298. Actual mass for M+Na$^+$ −769.39222.

EXAMPLE 10.6

26-Phenylmethyloxy-3,6,9,12,15,18,21,24-octaoxa-hexaeicosan-1-ol (17)

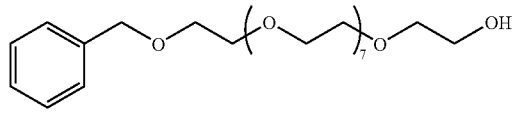

To 1-triphenylmethyloxy-26-phenylmethyloxy-3,6,9,12,15,18,21,24-octaoxahexaeicosane (16) (24.0 g, 32.1 mmol) was added a solution of trifluoroacetic acid (20 ml) and triethylsilane (20 ml) in dichloromethane (160 ml). The reaction was left to stir at room temperature for 1 hour. After one hour sat. aq. Na$_2$CO$_3$ was slowly added to the reaction with vigorous stirring until the reaction reached pH 12. The two layers were partitioned and the aqueous fraction was back-extracted several times with dichloromethane (9×100 ml). The organic fractions were combined, dried over anhydrous sodium sulphate and concentrated in vacuo to give a yellow solid/oil. This oil was re-dissolved in water (200 ml) and the aqueous solution was partitioned twice with hexane (2×200 ml). The aqueous solution was then concentrated in vacuo to give a yellow oil. The resulting opaque oil was azeotroped with anhydrous acetonitrile until 16.2 g (99.9%) of a colourless oil was obtained.

$^1$H NMR (CDCl$_3$) δ: 3.57-3.73 (36H, m, C$_6$H$_5$CH$_2$OCH$_2$(CH$_2$OCH$_2$)$_8$CH$_2$OH), 4.55 (2H, s, C$_6$H$_5$CH$_2$OCH$_2$(CH$_2$OCH$_2$)$_8$CH$_2$OH), 7.21-7.33 (5H, m, C$_6$H$_5$CH$_2$OCH$_2$(CH$_2$OCH$_2$)$_8$CH$_2$OH). $^{13}$C NMR (CDCl$_3$) δ: 61.57 (1C, C1), 69.46, 70.19, 70.44, 70.46, 70.55, 70.62 (16C, C4-C26), 72.38 (1C, C2), 73.22 (1C, —OCH$_2$C$_6$H$_5$), 127.55, 127.69, 128.32, 138.30 (7C, benzyl). IR v/cm$^{-1}$ (NaCl): 3333 (vst., O—H stretch), 3030 (wk., Aryl-H stretch), 2869 (st., C—H stretch), 1455 (med., C=C aromatic stretch), 1104 (vst., C—O stretch).

EXAMPLE 10.7

26-Phenylmethyloxy-1-azido-3,6,9,12,15,18,21,24-octaoxahexaeicosane (18)

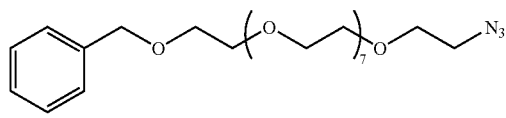

To 26-pheylmethyloxy-3,6,9,12,15,18,21,24-octaoxahexaeicosan-1-ol (17) (16.28 g, 32.1 mmol) and triethylamine (11.33 g, 15.6 ml, 112 mmol) in dry dichloromethane (200 ml), undo nitrogen, at 0° C. was slowly added methanesulphonyl chloride (7.43 ml, 10.99 g, 96 mmol, 3 eq.) in dry dichloromethane (75 ml). Once addition was complete, the reaction was left to warm to room temperature. After 4 hours, excess sat. aq. NaCO$_3$ was added and the reaction was left to stir for 10 minutes. Additional dichloromethane (300 ml) was added, the aqueous and organic layers were separated and the organic solution was partitioned with sat. aq. NaCl (250 ml). The aqueous solution was back-extracted with dichloromethane (2×250 ml), the organic solutions were combined, dried over anhydrous sodium sulphate and concentrated in vacuo to give an orange oil. The oil was then azeotroped several times with dry toluene to remove water. This oil became a red solid after several hours in high vacuo.

This red solid was redissolved in dry dimethylformamide (200 ml) and sodium azide (10.4 g, 160 mmol, 5 eq.) was added. The reaction was left to stir for 72 hours at room temperature, under argon. After 72 hours the reaction was concentrated in vacuo, xylene (250 ml) was then added and the reaction was once again concentrated in vacuo. The reaction mixture was triturated with diethyl ether (750 ml) and filtered, the filtrate, being concentrated in vacuo to give an orange oil. The product was isolated by N.P.S.G. chromatography, eluting initially with ethyl acetate and then gradually changing to ethyl acetate/methanol (95:5) to yield 14.4 g (85.0%) of a yellow oil.

$^1$H NMR (CDCl$_3$) δ: 3.36 (2H, t, J=5.1 Hz, C$_6$H$_5$CH$_2$OCH$_2$(CH$_2$OCH$_2$)$_8$CH$_2$N$_3$), 3.58-3.70 (34H, m, C$_6$H$_5$CH$_2$OCH$_2$(CH$_2$OCH$_2$)$_8$CH$_2$N$_3$), 4.55 (2H, s, C$_6$H$_5$CH$_2$OCH$_2$(CH$_2$OCH$_2$)$_8$CH$_2$N$_3$), 7.21-7.33 (5H, m, C$_6$H$_5$CH$_2$OCH$_2$(CH$_2$OCH$_2$)$_8$CH$_2$N$_3$). $^{13}$C NMR (CDCl$_3$) δ: 50.70 (1C, C1), 69.48, 70.0, 70.59, 70.65 (17C, C2-C26), 73.22 (1C, —OCH$_2$C$_6$H$_5$), 127.54, 127.69, 128.32, 138.33 (7C, benzyl). IR v/cm$^{-1}$ (NaCl): 3020 (wk., Aryl-H stretch), 2866 (st., C—H stretch), 2106 (st., azide stretch), 1454 (med., C=C aromatic stretch), 1105 (vst., C—O stretch). MS m/z (+ve ES): 568 (M+K$^+$, 2%), 552 (M+Na$^+$, 99%), 524 ([C$_{25}$H$_{43}$O$_9$N]+Na$^+$, 3%). HRMS (+ve ion FAB): Measured mass −552.2906. Actual mass for M+Na$^+$ −552.2897.

EXAMPLE 10.8

26-Phenylmethyloxy-1-amino-3,6,9,12,15,18,21,24-octaoxahexaeicosane (19)

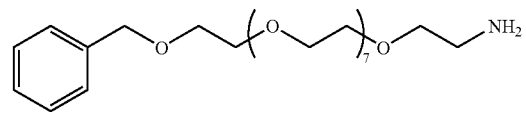

To 26-phenylmethyloxy-1-azido-3,6,9,12,15,18,21.24-octaoxahexaeicosane (18) (5.29 g, 10 mmol) in tetrahydrofuran (50 ml) was added triphenylphosphine (2.89 g, 11 mmol, 1.1 eq.). The reaction was left to stir for two hour at room temperature before water (0.8 ml, 44 mmol, 4.4 eq.) was added. The reaction was then left to stir for 48 hours at room temperature.

The reaction mixture was then concentrated in vacuo, redissolved in toluene (100 ml) and then concentrated in vacuo once more. The product was isolated from the resulting oil/solid by N.P.S.G. chromatography, eluting initially with copious amounts of chloroform and then gradually changing to chloroform/methanol/triethylamine (90:5:5) to yield 4.86 g (96.5%) of a pale yellow oil.

¹H NMR (DMSO) δ: 2.67 (2H, t, J=5.78 Hz, C₆H₅CH₂OCH₂(CH₂OCH₂)₈CH₂NH₂), 3.38 (2H, t, J=5.78 Hz, C₆H₅CH₂O(CH₂CH₂O)₈CH₂CH₂NH₂), 3.49-3.61 (32H, m, C₆H₅CH₂O(CH₂OCH₂)₈CH₂CH₂), 4.51 (21, s, C₆H₅CH₂OCH₂(CH₂OCH₂)₈CH₂NH₂), 7.27-7.39 (5H, m, C₆H₅CH₂OCH₂(CH₂OCH₂)₈CH₂NH₂). ¹³C NMR (DMSO) δ: 42.19 (1C, C1), 70.05, 70.50, 70.70 (16C, C4-C26), 72.94 (1C, C2), 73.78 (1C, —OCH₂C₆H₅), 128.24, 128.35, 129.09, 139.41 (7C, benzyl). IR ν/cm⁻¹ (NaCl): 3269 (med., N—H stretch), 3050 (wk., Aryl-H stretch), 2869 (st., C—H stretch), 1601 (med., N—H bend), 1452 (med., C=C aromatic stretch), 1252 (med., C—O & C—N stretch), 1106 (vst., C—O stretch). MS m/z (+ve ES): 526 (M+Na⁺, 8%), 504 (M+H⁺, 99%), 524 ([C₁₈H₄₀O₉N]⁺, 13%). HRMS (+ve ESI): Measured mass −504.31645. Actual mass for M+H⁺ −504.31671.

EXAMPLE 10.9

26-(9-Fluorenylmethyloxycarbonylamido)-3,6,9,12,15,18,21,24-octaoxahexaeicosan-1-ol (20)

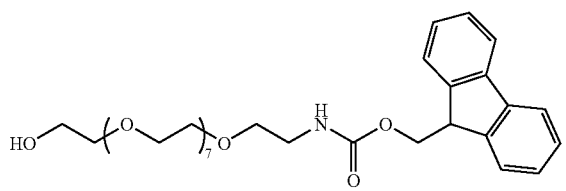

A solution of 26-phenylmethyloxy-1-amino-3,6,9,12,15,18,21,24-octaoxahexaeicosane (19) (5.51 g, 10.94 mmol) in dry diethyl ether (50 ml) under argon was cooled to −78° C. Into this solution was condensed ammonia until the volume of the solution had almost doubled (c. 100 ml). To the solution under argon at −78° C. were added sodium pellets until a dark blue colour persisted. The reaction was allowed to warm to from −78° C. to −30° C. and then cooled back to −78° C. Methanol was then slowly added to the reaction at −78° C. under argon until the solution was no longer blue in colour. The reaction was then allowed to warm to room temperature and the majority of the ammonia was allowed to evaporate. The reaction was concentrated in vacuo and then kept under high vacuum for 24 hours.

To the remaining residue was then added water (100 ml) and the pH was adjusted to 4 with concentrated hydrochloric acid. The pH of the solution was then adjusted to 7 by addition of solid sodium hydrogencarbonate. Once the solution had been neutralised, sodium hydrogencarbonate (1.38 g, 16.41 mmol, 1.5 eq.) was again added followed by water (50 ml) and dioxane (100 ml). To this solution cooled to 0° C. was slowly added fluorenylmethyl chloroformate (4.25 g, 16.41 mmol, 1.5 eq.) in dioxane (50 ml). Once addition was complete the reaction was allowed to warm to room temperature and left to stir for 6 hours.

After 6 hours the solution was acidified to pH 6 by addition of solid citric acid and then concentrated in vacuo to remove dioxane. The remaining aqueous solution was partitioned three times with chloroform (3×250 ml). The organic fractions were combined, dried over anhydrous sodium sulphate and concentrated in vacuo to give a yellow oil. This oil was purified by N.P.S.G. chromatography, eluting with ethyl acetate/methanol (4:1) to yield 6.1 g (87.7%) of a yellow oil.

¹H NMR (CDCl₃) δ: 2.71 (1H, bs, —OH), 3.39 (2H, m, HOCH₂(CH₂OCH₂)₈CH₂NHFmoc), 3.55-3.73 (34H, m, HOCH₂(CH₂OCH₂)₈CH₂NHFmoc), 4.22 (1H t, J=6.8 Hz, *H9), 4.41 (2H, d, J=6.8 Hz, HOCH₂(CH₂OCH₂)₈CH₂NHCOCH₂), 5.50 (1H, bs, —NH—), 7.31 (2H, t, J=7.4 Hz, *H3 & *H6), 7.39 (2H, t, J=7.4 Hz, *H2 & *H7), 7.61 (2H, d, J=7.4 Hz, *H4 & *H5), 7.76 (2H, d, J=7.4 Hz. *H1 & *H8). ¹³C NMR (CDCl₃) δ: 40.96 (1C, C₂₆), 47.31 (1C, *C9), 61.72 (1C, C1), 66.55 (1C, —NHCOCH₂C₁₃H₉), 70.06, 70.35, 70.57 (15C, C4-C25), 72.55 (1C, C2), 119.94, 125.08, 127.04, 127.65 (8C, *C1, *C2, *C3, *C4, *C5, *C₆, *C7 and *C8), 141.32, 144.04 (4C, *C4a, *C4b, *C8a and *C9a), 156.56 (1C, carbamate C=O). IR ν/cm⁻¹ (NaCl): 3325 (st., O—H & N—H stretch), 3066, 3041, 3020 (wk., Aryl-H stretch), 2883 (st., C—H stretch), 1672 (vst. carbamate C=O stretch & N—H bend), 1452 (med, C=C aromatic stretch), 1346 (med., carbamate C—Ostretch), 1105 (vst., C—O stretch). MS m/z (+ve ion FAB): 658 (M+Na⁺, 8%). 636 (M+H⁺, 32%), 414 ([C₁₈H₄₀O₉N]⁺, 21%), 179 ([C₁₄H₁₁]⁺, 68%). HRMS (+ve ion FAB): Measured mass −636.3380. Actual mass for M+H⁺ −636.3384.

EXAMPLE 10.10

26-(9-Fluorenylmethyloxycarbonylamido)-3,6,9,12,15,18,21,24-octaoxahexaeicosanoic acid (Fmoc-Haa9) (21)

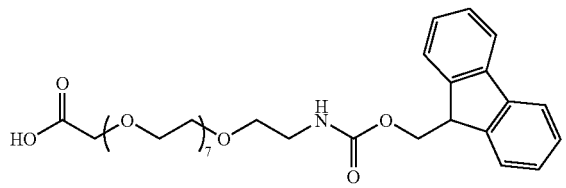

To vigorously stirring 26-(9-fluorenylmethyloxycarbonylamido)-3,6,9,12,15,18,21,24-octaoxahexa-eicosan-1-ol (20) (6.10 g, 9.60 mmol) in acetone (125 ml) at 0° C. was very slowly added chromium trioxide (2.878 g, 28.8 mmol, 3 eq.) in sulphuric acid (1.5 M, 57.6 ml, 86.4 mmol, 9 eq.). Once addition was complete the reaction was left to warm to room temperature and to stir for 24 hours.

After 24 hours water (400 ml) was added to the reaction along with reverse phase silica gel (120 g). The reason mixture was concentrated in vacuo until the volume had decreased by approximately one quarter and more water (100 ml) was added. The reaction mixture was once again concentrated in vacuo until no acetone could be detected to be present in the mixture. The mixture was then filtered to recover the R.P. silica gel which was washed with copious amounts of water until the silica gel was almost colourless. The R.P. silica gel was then washed with acetonitrile (4×200 ml) and chloroform (3×150 ml). The organic fractions were combined and concentrated in vacuo to give a pale green oil. The product was isolated by N.P.S.G. chromatography, eluting initially with chloroform only, then gradually changing to chloroform/methanol (95:5) and finally gradually changing to chloroform/methanol/acetic acid (80:15:5) to yield 4.38 g (70.0%) of a yellow oil.

¹H NMR (CDCl₃) δ: 3.38 (2H, m, HO₂C(CH₂OCH₂)₈CH₂NHCOCH₂C₁₃H₉), 3.54-3.73 (30H, m, HO₂CCH₂OCH₂(CH₂OCH₂)₇CH₂NHCOCH₂C₁₃H₉), 4.14 (2H, s, HO₂CCH₂(OCH₂CH₂)₈NHCOCH₂C₁₃H₉), 4.21 (1H, t, J=6.9 Hz, *H9), 4.39 (2H, d, J=6.9 Hz, HO₂C(CH₂OCH₂)₈CH₂NHCOCH₂C₁₃H₉), 5.54 (1H, bs, —NH—), 7.31

(2H, t, J=7.4 Hz, *H3 & *H6), 7.38 (2H, t, J=7.4 Hz, *H2 & *H7), 7.59 (2H, d, J=7.4 Hz, *H4 & *H5), 7.74 (2H, d, J=7.4 Hz, *H1 & *H8). $^{13}$C NMR (CDCl$_3$) δ: 40.94 (1C, C$_{26}$), 47.27 (1C, *C9), 66.59 (1C, —NHCOCH$_2$C$_{13}$H$_9$g), 70.05, 70.33, 70.49, 70.58, 71.11 (16C, C2-C25), 119.94, 125.09, 127.05, 127.66 (8C, *C1, *C2, *C3, *C4, *C5, *C6, *C7 and *C8), 141.30, 144.00 (4C, *C4a, *C4b, *C8a and *C9a), 156.65 (1C, carbamate C=O), 171.64 (1C, C=O). IR v/cm$^{-1}$ (NaCl): 3336 (st., carboxylic O—H stretch), 3060 (wk., Aryl-H stretch), 2881 (st., C—H stretch), 1714, 1700 (vst., carbamate C=O stretch & carboxylic acid C=O stretch), 1600 (st., carbamate N—H bend), 1451 (st., carboxylic O—H bend), 1251 (st., carbamate & carboxylic C—O stretch), 1106 (vst., C—O stretch). MS m/z (+ve ES): 672 (M+Na$^+$, 2%). 650 (M+H$^+$, 99%), 428 ([C$_{18}$H$_{38}$O$_{10}$N]$^+$, 4%). HRMS (+ve ESI): Measured mass −672.299822. Actual mass for M+Na$^+$ −672.29905.

EXAMPLE 11

General Synthesis of Peptides Containing PEG Amino Acids

Standard Procedures

Solid-phase peptide synthesis was carried out either manually on a Merrifield Bubbler or automatically on a peptide synthesiser module (MilliGen 9050Plus PepSynthesiser). All reagents used for either manual or automatic synthesis were purchased from commercial suppliers, with the exception of the Fmoc-protected amino acids Haa4, Haa7 and Haa9 whose syntheses have been described earlier in Examples 8 to 10. HIPERSOLV© DMF of HPLC grade was used straight from the bottle, whilst dichloromethane and piperidine were freshly distilled over calcium hydride before use. All peptide syntheses were carried out under nitrogen.

The solid support used for SPPS was a NovaSyn-TGT resin pre-loaded with N-α-Fmoc-glycine. All SPPS reactions were carried out at room temperature.

| Reagent/Solution | Concentration |
| --- | --- |
| De-block reagent | 30% Piperidine in DMF |
| Coupling reagent 1 | 0.6M DIPCI in DMF (A1) or 0.6M TBTU & 0.6M HOBt in DMF (B1) |
| Coupling reagent 2 | 0.6M HOBt in DMF (A2) or 1.0M DIPEA (B2) |
| Auxiliary wash | 0.3M NAI in DMF |
| Wash solution | DMF/DCM (3:2) |

Peptide-Resin Cleavage and Peptide Deprotection

To the dry resin-bound peptide (0.110 mmol) in a Merrifield bubbler was added a solution (10 ml) consisting of trifluoroacetic acid (85%), thioanisole (5%), phenol (5%), water (2.5%) and triethylsilane (2.5%). The resin-bound peptide in the solution was left to agitate for 10 minutes by bubbling with a stream of nitrogen. After 10 minutes, the solution was drained into a flask. Another volume of the solution (10 ml) was then added to the resin-bound peptide and again bubbling with N$_2$ was re-commenced for 10 minutes. The solution was drained into the flask and the above procedure was repeated four more times. Once this was complete, the content of the flask was left to stir at room temperature, under nitrogen for 6 hours.

After 6 hours, the solution was concentrated in vacuo and, to the residue that remained was added diethyl ether/hexane (1:1, 50 ml). The organic solution was carefully decanted to retain the solid precipitate that had formed, which was then dried under vacuum. The solid was then re-dissolved in water, degassed under vacuum and freeze-dried.

EXAMPLE 12

Synthesis of M109

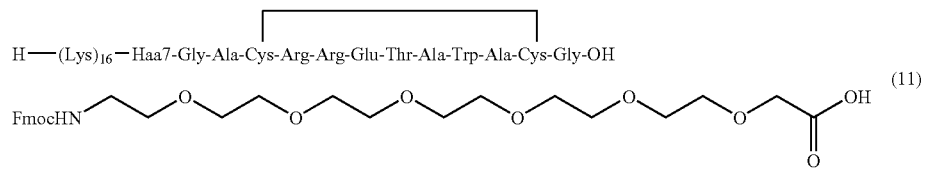

M109 is an I-peptide formed from Fmoc-Haa7, the synthesis for which is shown in Example 9. The structure of M109 is shown above, above the structure of Fmoc-Haa7 (11).

The sequence Gly-Ala-Cys(Trt)-Arg(Pbf)-Arg(Pbf)-Glu(OtBu)-Thr(tBu)-Ala-Trp(Boc)-Ala-Cys(Trt)-Gly was assembled on the MilliGen 9050 using standard procedures, coupling with 0.6 M DIPCI in DMF/0.6 M HOBt in DMF.

The protected PEG amino acid, Fmoc-Haa7, was then added manually, as follows. The resin-bound peptide (0.37 g, 0.055 mmol) was then pre-swelled with DMF on a Merrifield Bubbler under nitrogen. The DMF was removed, 1,8-diazabicyclo[5.4.0]undec-7-ene/piperidine/DMF (1:1:48, 8 ml) was added to cover the resin-bound peptide and the reaction was agitated by nitrogen bubbling over 10 minutes. After 10 minutes, the deprotection solution was removed and the resin-bound peptide was washed with DMF (2×10 ml). A further quantity of 1,8-diazabicyclo[5.4.0]undec-7-ene/piperidine/DMF (1:1:48, 8 ml) was again added and bubbling was re-commenced for 10 minutes, followed by washing with DMF. This procedure was repeated further three times. After the final de-protection, the resin-bound peptide was thoroughly washed with DMF (50 ml). 20-(9-Fluorenylmethyloxycarbonylamido)-3,6,9,12,15,18-hexaoxoeicosanoic acid (11) (0.123 g, 0.22 mmol), HATU (0.083 g, 0.22 mmol) and HOAt (0.029 g, 0.22 mmol) were dissolved in the minimum quantity of DMF (5 ml). To this solution was added N,N-diisopropylethylamine (0.096 ml, 0.0711 g, 0.55 mmol) and the resulting solution was immediately added to the resin-bound peptide. The reaction was agitated by bubbling with $N_2$ for one hour.

After one hour, the reagent solution was removed and the resin-bound peptide was washed with DMF (2×20 ml). 1,8-diazabicyclo[5.4.0]undec-7-ene/piperidine/DMF (1:1:48, 8 ml) was added to cover the resin-bound peptide and the reaction was agitated by nitrogen bubbling over 10 minutes. After 10 minutes, the de-protection solution was removed and the resin-bound peptide was washed with DMF (2×10 ml). A further quantity of 1,8-diazabicyclo[5.4.0]undec-7-ene/piperidine/DMF (1:1:48, 8 ml) was again added and bubbling was re-commenced for 10 minutes, followed by washing with DMF. This procedure was repeated a further three times. After the final de-protection, the resin-bound peptide was thoroughly washed with DMF (50 ml). Fmoc-Lysine(Boc)-OH (0.103 g, 0.22 mmol), HATU (0.083 g, 0.22 mmol) and HOAt (0.029 g, 0.22 mmol) were dissolved in the minimum quantity of DMF (5 ml). To this solution was added N,N-diisopropylethylamine (0.096 ml, 0.0711 g, 0.55 mmol) and the resulting solution was immediately added to the resin-bound peptide. The reaction was agitated by bubbling with $N_2$ for one hour.

After one hour, the reagent solution was removed and the resin-bound peptide was washed with DMF, dichloromethane, and diethyl ether, then dried under vacuum. A small quantity of the resin-bound peptide (~40 mg) was cleaved and deprotected by the standard procedure. The residue recovered from cleavage/deprotection was analysed by mass spectroscopy and was found by mass spectrometry to contain almost exclusively the desired product:

MS m/z (+ve ES): Measured mass –1953.01 (652.1 [M+3H$^+$]/3,977.4 [M+2H$^+$]/2). Calculated mass –1952.24.

The remaining resin-bound peptide was re-loaded onto the reaction column in DMF and the remainder of the sequence was assembled on the MilliGen 9050 using standard procedures, coupling Fmoc-Lys(Boc) with 0.6M TBTU & 0.6 M HOBt in DMF/1.0 M DIPEA. The peptide was cleaved from the resin and deprotected using the general procedure. The residue was analysed by MS and was found to contain the desired peptide. The residue was then re-dissolved in water, de-gassed under vacuum and freeze-dried.

The residue was then purified by preparative reverse phase HPLC, using the solvent gradient profile given below (Table 1). Both water and acetonitrile contained 0.1% trifluoroacetic acid. The retention time of the product was approximately 20 minutes ($H_2O$/MeCN, 83:17).

TABLE 1

| Solvent gradients (flow - 15 ml/min) | | |
|---|---|---|
| Time (min) | % Water | % Acetonitrile |
| 0 | 95 | 5 |
| 30 | 75 | 25 |
| 40 | 0 | 100 |

MS analysis of the peptide recovered from HPLC purification showed that the peptide had been purified and recovered:

MS m/z (+ve ES): Measured mass –3652.56 (457.6 [M+8H$^+$]/8, 522.8 [M+7H$^+$]/7, 609.7 [M+6H$^+$]/6, 731.6 [M+5H$^+$]/5). Calculated mass –3652.61.

The peptide was dissolved in degassed water to make a final concentration of ~0.25 mg/ml. The solution was left to stir at room temperature exposed to the atmosphere for one week. After one week the reaction was concentrated in vacuo, the remaining residue was re-dissolved in degassed water and freeze-dried.

The residue was then purified by preparative reverse phase HPLC, using the solvent gradient profile given below (Table 2). Both water and acetonitrile contained 0.1% trifluoroacetic acid. The retention time of the product was approximately 22 minutes ($H_2O$/MeCN, 81:19).

TABLE 2

| Solvent gradients (flow - 15 ml/min). | | |
|---|---|---|
| Time (min) | % Water | % Acetonitrile |
| 0 | 95 | 5 |
| 30 | 75 | 25 |
| 40 | 0 | 100 |

MS analysis of the peptide recovered from HPLC purification showed that the peptide had been successfully oxidised:

MS m/z (+ve ES): Measured mass –3651.01 (457.4 [M+8H$^+$]/8, 522.6 [M+7H$^+$]/7, 609.5 [M+6H$^+$]/6, 731.1 [M+5H$^+$]/5). Calculated mass –3650.60.

EXAMPLE 13

Synthesis of 1HAA

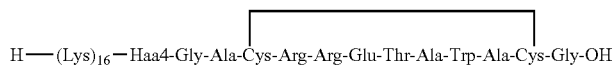

(6)

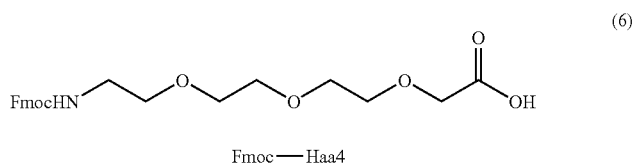

Fmoc—Haa4

1HAA is an I-peptide formed from Fmoc-Haa4, the synthesis for which is shown earlier in Example 8. The structure of 1HAA is shown above, above the structure of Fmoc-Haa4 (6).

The sequence Gly-Ala-Cys(Trt)-Arg(Pbf)-Arg(Pbf)-Glu (OtBu)-Thr(tBu)-Ala-Trp(Boc)-Ala-Cys(Trt)-Gly was assembled on the MilliGen 9050 using standard procedures, coupling with 0.6 M DIPCI in DMF/0.6 M HOBt in DMF. Fmoc-Haa4 (6) was then added, coupling with 0.6M TBTU & 0.6 M HOBt in DMF/1.0 M DIPEA; the Fmoc de-protection time was extended by 10 minutes and the recycle time extended by 10 minutes. The remainder of the sequence was then also assembled on the MilliGen 9050 using standard procedures, coupling Fmoc-Lys(Boc) with 0.6M TBTU & 0.6 M HOBt in DMF/1.0 M DIPEA.

The peptide was cleaved from the resin and deprotected by the standard procedure. The residue was analysed by MS and was found to contain the desired peptide. The residue was then re-dissolved in water, de-gassed under vacuum and freeze-dried.

The residue was purified by preparative reverse phase HPLC, using the solvent gradient profile given below (Table 3). Both water and acetonitrile contained 0.1% trifluoroacetic acid. The retention time of the product was approximately 27 minutes ($H_2O$/MeCN, 81:19).

TABLE 3

| Solvent gradients (flow - 15 ml/min) | | |
|---|---|---|
| Time (min) | % Water | % Acetonitrile |
| 0 | 95 | 5 |
| 30 | 80 | 20 |

MS analysis of the peptide recovered from HPLC purification showed that the peptide had been purified and recovered:

MS m/z (+ve ES): Measured mass −3518.80 (503.76 [M+7H$^+$]/7, 587.45 [M+6H$^+$]/6, 704.69 [M+5H$^+$]/5, 880.70 [M+4H$^+$]/4, 1174.04 [M+3H$^+$/3]). Calculated mass −3520.40.

The peptide was then dissolved in degassed water to make a final concentration of ~0.25 mg/ml. The solution was left to stir at room temperature exposed to the atmosphere for one week. After one week the reaction was concentrated in vacuo, the remaining residue was redissolved in degassed water and freeze-dried.

The residue was then purified by preparative reverse phase HPLC, using the solvent gradient profile given below (Table 4). Both water and acetonitrile contained 0.1% trifluoroacetic acid. The retention time of the product was approximately 29 minutes ($H_2O$/MeCN, 80:20).

TABLE 4

| Solvent gradients (flow - 15 ml/min) | | |
|---|---|---|
| Time (min) | % Water | % Acetonitrile |
| 0 | 95 | 5 |
| 30 | 80 | 20 |

MS analysis of the peptide recovered from HPLC purification showed that the peptide had been successfully oxidised;

MS m/z (+ve ES): Measured mass −3515.75 (704.12 [M+5H$^+$]/5, 879.89 [M+4H$^+$/4, 1172.92 [M+3H$^+$/3). Calculated mass −3518.38.

EXAMPLE 14

Synthesis of 2HAA

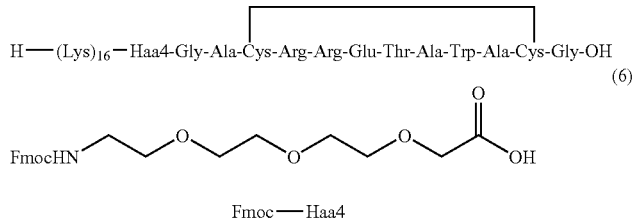

Fmoc—Haa4

2HAA is an I-peptide formed from Fmoc-Haa4, the synthesis for which is shown earlier in Example 8. The structure of 2HAA is shown above, above the structure of Fmoc-Haa4 (6).

The sequence Gly-Ala-Cys(Trt)-Arg(Pbf)-Arg(Pbf)-Glu (OtBu)-Thr(tBu)-Ala-Trp(Boc)-Ala-Cys(Trt)-Gly was assembled on the MilliGen 9050 using standard procedures, coupling with 0.6 M DIPCI in DMF/0.6 M HOBt in DMF. Two Fmoc-Haa4 (6) were then added sequentially, coupling with 0.6M TBTU & 0.6 M HOBt in DMF/1.0 M DIPEA; the Fmoc de-protection time was extended by 10 minutes and the recycle time extended by 10 minutes. The remainder of the sequence was then also assembled on the MilliGen 9050 using standard procedures, coupling Fmoc-Lys(Boc) with 0.6M TBTU & 0.6 M HOBt in DMF/1.0 M DIPEA.

The peptide was cleaved from the resin and de-protected by the standard procedure. The residue was analysed by MS and was found to contain the desired peptide. The residue was then re-dissolved in water, de-gassed under vacuum and freeze-dried.

The residue was purified by preparative reverse phase HPLC, using the solvent gradient profile given below (Table 5). Both water and acetonitrile contained 0.1% trifluoroacetic acid. The retention time of the product was approximately 28 minutes ($H_2O$/MeCN, 81:19).

TABLE 5

| Solvent gradients (flow - 15 ml/min) | | |
|---|---|---|
| Time (min) | % Water | % Acetonitrile |
| 0 | 95 | 5 |
| 30 | 80 | 20 |

MS analysis of the peptide recovered from HPLC purification showed that the peptide had been purified and recovered;

MS m/z (+ve ES): Measured mass −3708.78 (464.72 [M+8H$^+$]/8, 530.86 [M+7H$^+$]/7, 619.14 [M+6H$^+$]/6, 742.75 [M+5H$^+$]/5, 928.05 [M+4H$^+$/4). Calculated mass −3709.05.

The peptide was then dissolved in degassed water to make a final concentration of ~0.25 mg/ml. The solution was left to stir at room temperature exposed to the atmosphere for one week. After one week the reaction was concentrated in vacuo, the remaining residue was re-dissolved in de-gassed water and freeze-dried.

The residue was then purified by preparative reverse phase HPLC, using the solvent gradient profile given below (Table 6). Both water and acetonitrile contained 0.1% trifluoroacetic acid. The retention time of the product was approximately 29 minutes (H$_2$O/MeCN, 80:20).

TABLE 6

| Solvent gradients (flow - 15 ml/min) | | |
|---|---|---|
| Time (min) | % Water | % Acetonitrile |
| 0 | 95 | 5 |
| 30 | 80 | 20 |

MS analysis of the peptide recovered from HPLC purification showed that the peptide had been successfully oxidised:

MS m/z (+ve ES): Measured mass −3705.12 (464.11 [M+8H$^+$]/8, 530.40 (M+7H$^+$]/7, 618.63 [M+6H$^+$]/6, 742.02 [M+5H$^+$]/5, 927.18 (M+4H$^+$/4). Calculated mass −3707.60.

EXAMPLE 15

Synthesis of Peg9

Peg9 is an I-peptide formed from Fmoc-Haa9, the synthesis of which is shown in Example 10. The structure of Peg9 is shown above, above the structure of Fmoc-Haa9 (21).

The sequence Gly-Ala-Cys(Trt)-Arg(Pbf)-Arg(Pbf)-Glu(OtBu)-Thr(tBu)-Ala-Trp(Boc)-Ala-Cys(Trt)-Gly was assembled on the MilliGen 9050 using standard procedures, coupling with 0.6 M DIPCI in DMF/0.6 M HOBt in DMF. Fmoc-Haa9 (21) was then added, coupling with 0.6M TBTU & 0.6 M HOBt in DMF/1.0 M DIPEA; the Fmoc de-protection time was extended by 10 minutes and the recycle time extended by 10 minutes. The remainder of the sequence was then also assembled on the MilliGen 9050 using standard procedures, coupling Fmoc-Lys(Boc) with 0.6M TBTU & 0.6 M HOBt in DMF/1.0 M DIPEA.

The peptide was cleaved from the resin and de-protected by the standard procedure. The residue was analysed by MS and was found to contain the desired peptide. The residue was then re-dissolved in water, de-gassed under vacuum and freeze-dried.

The residue was purified by preparative reverse phase HPLC, using the solvent gradient profile given below (Table 7). Both water and acetonitrile contained 0.1% trifluoroacetic acid. The retention time of the product was approximately 36 minutes (H$_2$O/MeCN, 81:19).

TABLE 7

| Solvent gradients (flow - 15 ml/min) | | |
|---|---|---|
| Time (min) | % Water | % Acetonitrile |
| 0 | 90 | 10 |
| 40 | 80 | 20 |

MS analysis of the peptide recovered from HPLC purification showed that the peptide had been purified and recovered;

MS m/z (+ve ES): Measured mass −3742.71 (535.85 [M+7H$^+$]/7, 624.83 [M+6H$^+$]/6, 749.40 [M+5H$^+$]/5, 936.49 [M+4H$^+$/4). Calculated mass −3740.71.

The peptide was then dissolved in degassed water to make a final concentration of ~0.25 mg/ml. The solution was left to stir at room temperature exposed to the atmosphere for one week. After one week the reaction was concentrated in vacuo, the remaining residue was redissolved in degassed water and freeze-dried.

The residue was then purified by preparative reverse phase HPLC, using the solvent gradient profile given below (Table 8). Both water and acetonitrile contained 0.1% trifluoroacetic acid. The retention time of the product was approximately 29 minutes (H$_2$O/MeCN, 83:17).

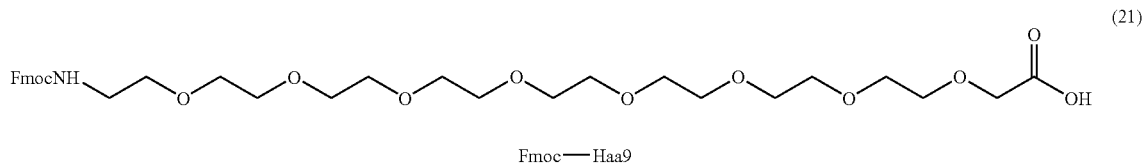

TABLE 8

Solvent gradients (flow - 15 ml/min)

| Time (min) | % Water | % Acetonitrile |
|---|---|---|
| 0 | 90 | 10 |
| 5 | 85 | 15 |
| 40 | 80 | 20 |

MS analysis of the peptide recovered from HPLC purification showed that the peptide had been successfully oxidised;

MS m/z (+ve ES); Measured mass –3740.26 (468.56 $[M+8H^+]/8$, 535.34 $[M+7H^+]/7$, 624.37 $[M+6H^+]/6$, 748.98 $[M+5H^+]/5$). Calculated mass –3738.69.

EXAMPLE 16

Testing of LID Systems

Cell Lines

The human airway epithelial cell line (HAEo-) was maintained in Eagle's minimal essential medium (MEM) HEPES modification (Sigma, Poole) containing 10% foetal calf serum (FCS), penicillin and streptomycin, and L-glutamine.

Lipopolyplex Formation

In the following descriptions the reference CH144 represents the known lipid DOTMA (N-[1-(2,3-dioleyloxy)propyl]-N,N,N-trimethyl-ammonium chloride). The abbreviation DOPE represents the known neutral ligand dioleyl phosphatidylethanolamine. The reference CH300 represents the ligand {2,3-Di-[(Z)-octadec-9-enyloxy]-propyl}-N-(2-{2-[2-(2-hydroxy-ethoxy)-ethoxy]-ethoxy}-ethyl)-N,N-diethylammonium bromide, the synthesis for which is given in Example 4 above.

The reference Peptide 6 represents the known peptide of formula:

Complexes were allowed to form electrostatically in a tube by adding the following components in the following order. 50 µl of liposomes (see table of formulations, Table 9) diluted to a concentration of 30 µg/ml in OptiMEM (In Vitrogen), followed by 70 µl peptide (at varying concentrations in OptiMEM for optimisation of the peptide:DNA charge ratio in the complex), with 50 µl of the luciferase reporter plasmid pCI-Luc at a concentration of 40 µg/ml in Optimem added finally. The complex was mixed by pipetting briefly before diluting in Optimem to a final volume of 1.57 mls.

In the Figures which follow, where the number "4" or "6" follows the name of the ligand used, this represents the ratio of lipid to DNA in the transfection assay. For example, "CH144 4" implies that the lipid DOTMA is used at a 4:1 ratio relative to the DNA component. Similarly, "CH300+DOPE 4" implies that the formulation comprising a 1:1 mixture of CH300 and DOPE is used at a 4:1 ratio relative to the DNA component.

In the Figures which follow, where the number "3" or "7" follows the name of the peptide used, this represents the charge ratio at which the peptides are formulated, relative to the DNA component. The charge ratio (N/P) is calculated from the molar amount of each free amine groups (N) in the peptide to the phosphate groups in the plasmid DNA backbone (P). Thus, "Peg 9 3" implies that the I-peptide of Example 11.4 (formed from the amino acid Fmoc-Haa9) is formulated in a complex at a charge ratio of 3:1 relative to the DNA component. Similarly, "Peptide 6 7" implies that Peptide 6 described above is formulated in a complex at a charge ratio of 7:1 relative to the DNA component.

TABLE 9

Table of Formulations

| Liposome | Formulation (in endotoxin free water) |
|---|---|
| CH144 (DOTMA) 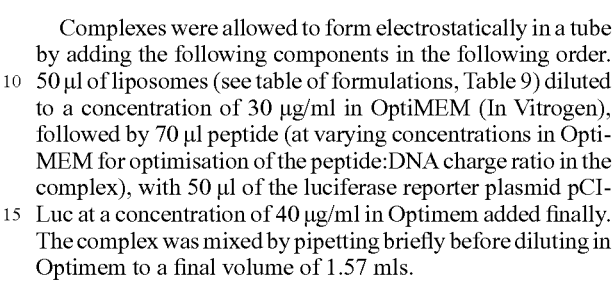 | 2 mg/ml |
| CH144 + DOPE (1:1 mass ratio) | 2 mg/ml |

TABLE 9-continued

Table of Formulations

| Liposome | Formulation (in endotoxin free water) |
|---|---|
| CH300 (see Example 4) [structure shown] | 2 mg/ml |
| CH300 + DOPE (1:1 mass ratio) [structures shown] | 2 mg/ml |

Transfection

The media was removed from subconfluent 1HAEo-cells plated at $2\times10^4$ cells/well overnight in 96 well plates and 200 μl of complex (approx. 0.25 μg of plasmid DNA) added to each well. Complex in OptiMEM was added to the cells within 30 minutes of mixing. In some experiments the transfection medium was augmented with heat-inactivated fetal calf serum up to a final concentration of 25%. All transfections were carried out in 6 wells each. The cells were incubated with the complexes for 4 hours before replacing with normal media for 48 hours, after which reporter gene expression was analysed by luciferase assay Promega).

Luciferase Assay

The cells were rinsed twice with PBS before the addition of 100 μl of reporter lysis buffer (Promega; diluted 1 in 5 in $dH_2O$) to the cells for 20 mins at 4° C. before freeze-thawing. 20 μl of the lysate was transferred to a white plate and the luciferase was measured by a Lucy1 luminometer (Anthos, Strasbourg, France) following the addition of 100 μl of reagent. The protein present in each transfection well was calculated using the Bio-Rad protein assay reagent (based on the Bradford assay), adding 20 μl from the luciferase test to 200 μl of the reagent diluted 1 in 5, incubating for 10 mins at room temperature and reading the absorbance at 590 nm. The total protein present per well was calculated from comparison with a range of bovine serum albumin (BSA) standards.

Results

The results are shown in FIGS. 1 to 4 which will now be described in more detail.

FIG. 1 shows the results when IHAEo-cells were transfected as described above. Lipopolyplex formulations contained lipids at weight ratio of 4:1 or 6:1 relative to the DNA component. The peptides were formulated in complexes at a charge ratio of 7:1 relative to the DNA component. Charge ratio (N/P) is calculated from the molar amount of each free amine groups (N) in the peptide to the phosphate groups in the plasmid DNA backbone (P).

Figure 2:
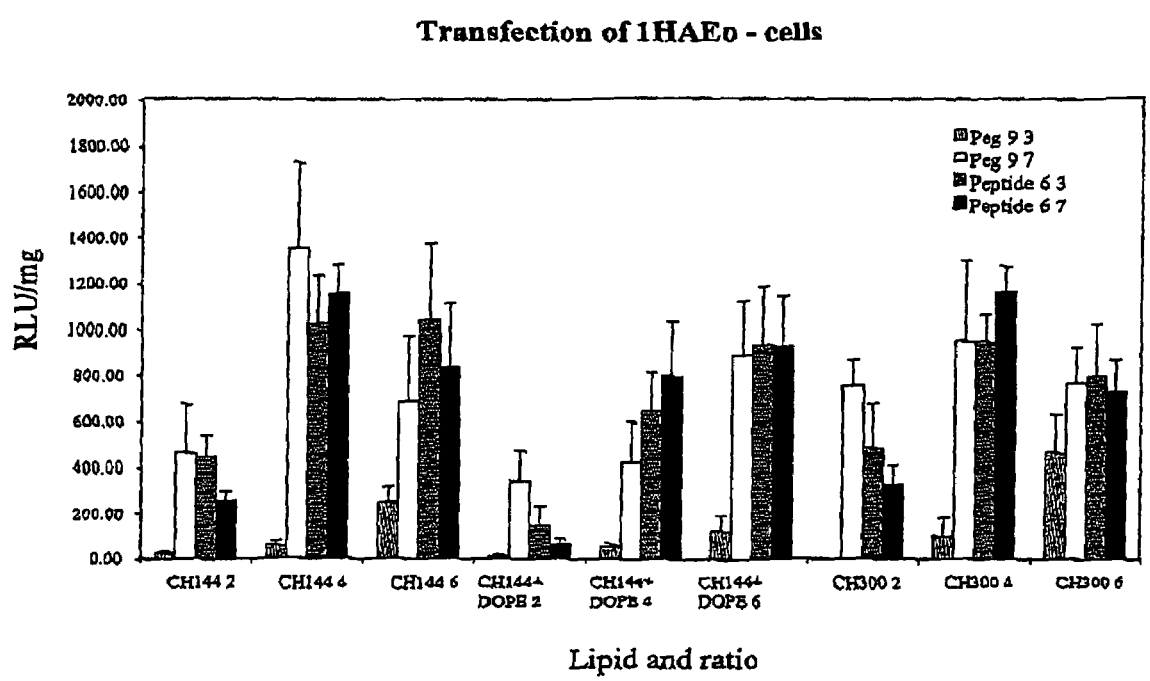
FIG. 2 discloses transfection data for IHAEo-cells for different ligands and peptides when the weight ratio of lipid to DNA component is varied.

FIG. 2 shows results when 1HAEo-cells were transfected as described above. Lipopolyplex formulations contained lipids at weight ratio of 2:1, 4:1 or 6:1 relative to the DNA component. The peptides were formulated in complexes at a charge ratio of 3:1 or 7:1 relative to the DNA component. Charge ratio (N/P) is calculated from the molar amount of each free amine groups (N) free group in the peptide to the phosphate groups in the plasmid DNA backbone (P).

Figure 3:
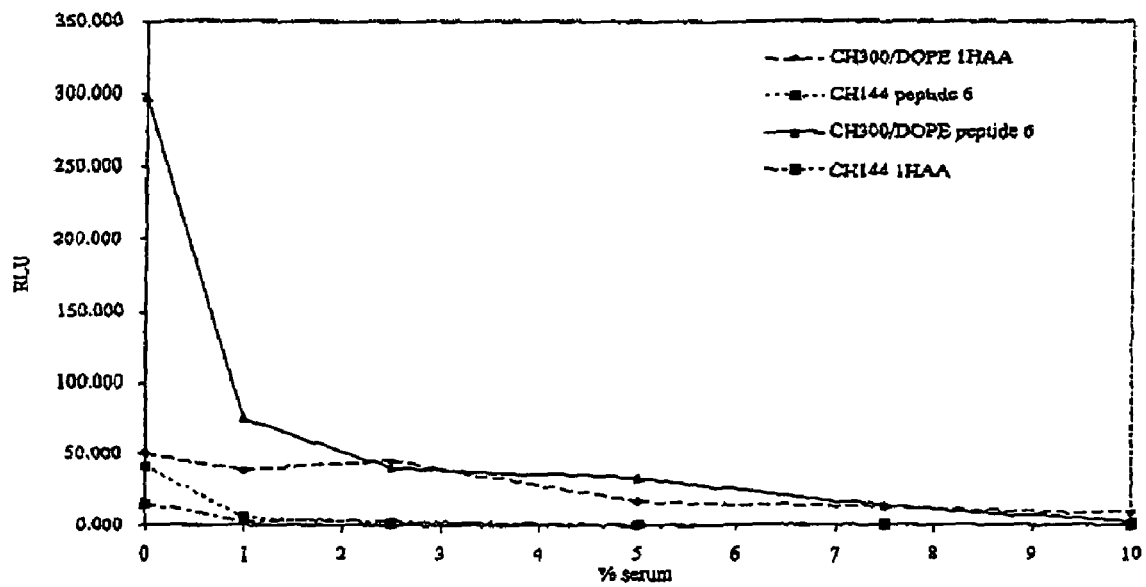
FIGS. 3 and 4 show the effect of serum on transfection using lipids and peptides of the invention.

FIG. 3 shows the results when IHAEo-cells were transfected as described above. Lipopolyplex formulations contained CH300/DOPE at weight ratio of 6:1 relative to the DNA component or CH144 at a ratio of 4:1 relative to DNA. These ratios were established to be optimal for transfections with each lipid in lipopolyplex formulations in previous experiments. The peptides were formulated in complexes at a charge ratio of 7:1 relative to the DNA component. Charge ratio (N/P) is calculated from the molar amount of each free amine groups (N) in the peptide to the phosphate groups in the plasmid DNA backbone (P). Foetal calf serum was included in the transfection incubation step in the range 0-10%.

All formulations were inhibited by serum except CH300/DOPE with peptide 1HAA which remained at a fairly constant level at all serum concentrations. Formulations with CH300/DOPE and peptide 6 gave the highest expression levels in the absence of serum which dropped markedly in the presence of 1-10% serum. Both CH300/DOPE formulations were better than CH144 formulations with the same peptides.

Figure 4:
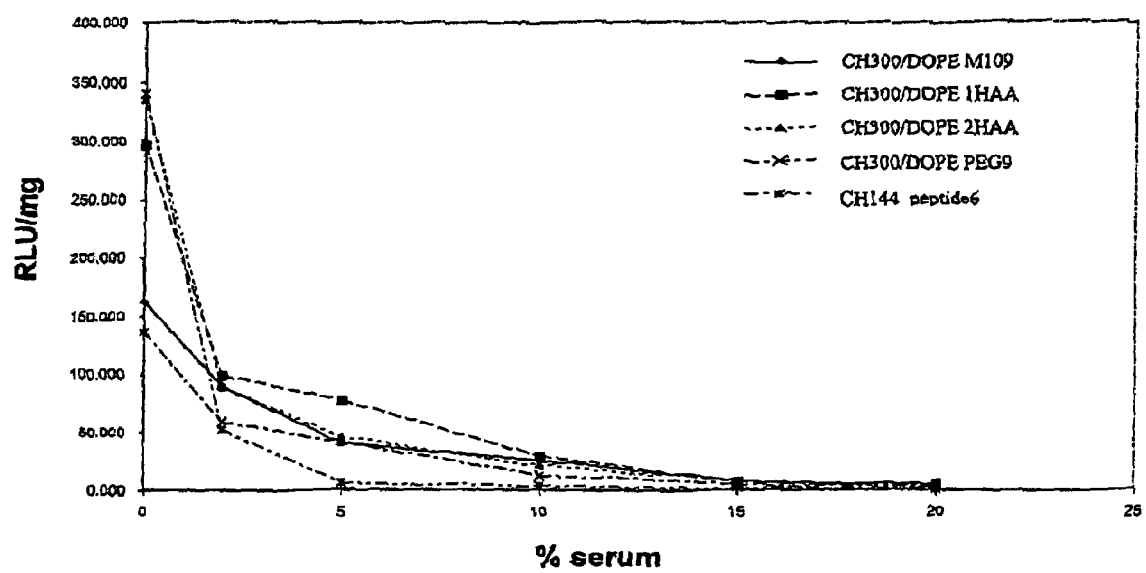

FIG. 4 shows the results when IHAEo-cells were transfected as described above. Lipopolyplex formulations contained CH300/DOPE at weight ratio of 6:1 relative to the DNA component or CH144 at a ratio of 4:1 relative to DNA. These ratios were established to be optimal for transfections with each lipid in lipopolyplex formulations in previous experiments. The peptides were formulated in complexes at a charge ratio of 7:1 relative to the DNA component. Charge

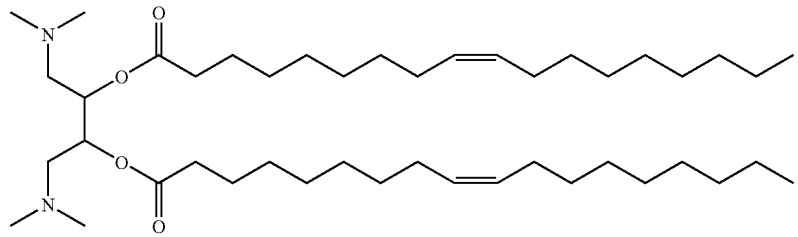

ratio (N/P) is calculated from the molar amount of each free amine groups (N) free group in the peptide to the phosphate groups in the plasmid DNA backbone (P). Foetal calf serum was included in the transfection incubation step in the range 0-25%.

All formulations were inhibited by serum. Consistent with FIG. 1, the formulation of CH300/DOPE with peptide 1HAA was the best formulation at serum concentrations up to 10%. CH300/DOPE formulations with all peptides were better than CH144 formulations with peptide 6.

EXAMPLE 17

1,4-Di(trimethylammonium)-2,3-dioleoyloxy-butane; diiodide

The first step was the production of 1,4-di(dimethylamino)-2,3-butanediol

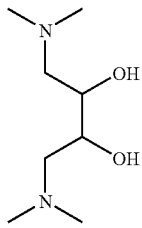

Powdered sodium hydroxide (1.28 g, 32.0 mmol) was stirred in methanol (7 ml) at 0° C. Dimethylamine hydrochloride (1.96 g, 24.0 mmol) was added followed by 1,4-dibromo-2,3-butanediol (1.00 g, 4.00 mmol). The mixture was then heated to 80° C. in a sealed tube for 24 hr. The mixture was then concentrated in vacuo. The residue was re-dissolved in chloroform (25 ml) and the resulting mixture was filtered. The filtrate was concentrated in vacuo to yield the titled product as clear oil which solidifies to a colourless waxy solid upon refrigeration (0.69 g, 98%).

$\delta_H$ (300 MHz, CDCl$_3$) 2.27 (12H s, NCH$_3$), 2.35 (2H, dd, J 12.6 Hz and J 4.9 Hz, NCH$_2$), 2.60 (2H, dd, J 12.5 Hz and J 8.2 Hz, NCH$_2$), 3.65 (2H, m, CHOH), 4.45 (2H, brs, OH);

$\delta_C$ (75 MHz, CDCl$_3$) 46.23 (NCH$_3$), 62.68 (NCH$_2$), 69.23 (CHOH);

m/z (APCI+) 177.2 (90%, M+1), 132.2 (100%);

$v_{max}$ cm$^{-1}$ (Film) 3417.6, 2920.0, 2783.1, 2343.4, 1633.6, 1461.9;

The 1,4-di(dimethylamino)-2,3-butane diol prepared above was then used to synthesise 1,4-di(dimethylamino)-2, 3-dioleoyloxy-butane.

1,4-Di(dimethylamino)-2,3-butanediol (0.30 g, 1.70 mmol), EDCI (0.98 g, 5.1 mol) and triethylamine (1.42 ml, 10.2 mmol) were stirred in anhydrous DCM (35 ml) at r.t. Oleic acid (1.44 g, 5.10 mmol) and DMAP (62.0 mg, 30 mol %) were and stirring was continued in the dark at r.t. Water (50 ml) was added and the mixture was separated and the chlorinated layer was subsequently washed with saturated sodium hydrogencarbonate solution (50 ml) and brine (50 ml). The chlorinated layer was dried over anhydrous magnesium sulfate and concentrated in vacuo. The product was purified by flash chromatography (gradient; DCM to 10% methanol in DCM) to obtain the above product as a clear yellow oil which solidified upon refrigeration (0.59 g, 50%).

$R_f$=0.80 (20% methanol in DCM);

$\delta_H$ (300 MHz, CDCl$_3$) 0.85 (6H, t, J 6.93 Hz, CH$_2$CH$_3$), 1.25 (40H, m), 1.60 (4H, m, O$_2$CCH$_2$CH$_2$), 2.00 (8H, m, CH$_2$CH=CHCH$_2$), 2.24 (12H, s, NCH$_3$), 2.32 (8H, m, NCH$_2$ and O$_2$CCH$_2$CH$_2$), 5.22 (2H, m, CHO$_2$C), 5.35 (4H, m, CH=CH);

$\delta_C$ (75 MHz, CDCl$_3$) 14.44 (CH$_2$CH$_3$), 23.04~32.27, 34.74 (O$_2$CCH$_2$CH$_2$), 46.24 (NCH$_3$), 59.96 (NCH$_2$), 70.48 (CHO$_2$CCH$_2$), 130.07 and 130.37 (CH=CH), 173.43 (C=O, ester);

m/z (APCI+) 705.8 (45%, M+1), 438.6 (100%);

$v_{max}$ cm$^{-1}$ (Film) 3408.0, 2923.9, 2854.5, 2769.6, 2337.6, 1739.7, 1461.9;

In a third step 1,4-di(trimethylammonium)-2,3-dioleoyloxy-butane; diiodide was formed.

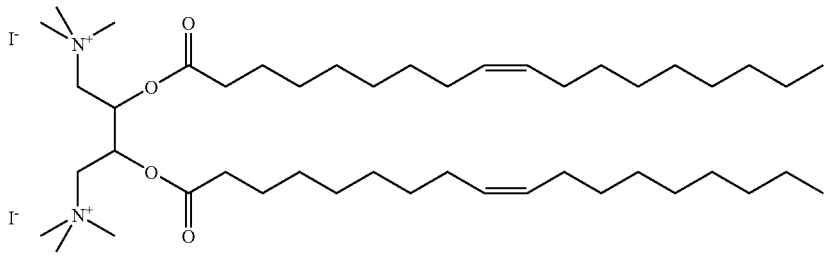

1,4-Di(dimethylamino)-2,3-dioleoyloxy-butane (296 mg, 0.42 mmol) and iodomethane (2.00 ml) in methanol (2 ml) were stirred in a sealed tube at 90° C. for 18 hr. The solvents were removed in vacuo to yield a residue. Ethyl acetate was added to the residue and an insoluble yellow solid was collected by filtration to yield the above product as a yellow waxy solid (385 mg, 93%).

$\delta_H$ (300 MHz, CDCl$_3$) 0.85 (6H, t, J 6.9 Hz, CH$_2$CH$_3$), 1.25 (40H, m), 1.60 (4H, m, O$_2$CCH$_2$CH$_2$), 2.00 (8H, m, CH$_2$CH=CHCH$_2$), 2.32 (4H, m, O$_2$CCH$_2$CH$_2$), 3.64 (18H, brs, NCH$_3$), 4.30 (2H, brs, NCH$_2$), 4.70 (2H, brs, NCH$_2$), 5.35 (4H, brm, CH=CH), 5.71 (2H, brm, CHO$_2$C);

$\delta_C$ (75 MHz, CDCl$_3$) 14.48 (CH$_2$CH$_3$), 23.04-32.27, 34,79 (O$_2$CCH$_2$CH$_2$), 55.86 (NCH$_3$), 66.85 (NCH$_2$), 77.62 (CHO$_2$CCH$_2$), 129.98 and 130.47 (CH=CH), 172.99 (C=O, ester);

m/z (ESP+) 367.6 (100%, ½M$^+$);

$\nu_{max}$ cm$^{-1}$ (nujol mull) 3399.8, 2916.6, 2854.0, 2708.4, 2353.9, 1745.4, 1460.0;

EXAMPLE 18

1,4-Di(trimethylammonium)-2,3-dioleyloxy-butane; diiodide

The first step of Example 17 was repeated, but in the second step the resulting butane diol was then used to synthesise an ether, rather than ester based lipid, namely 1,4-di(dimethylamino)-2,3-dioleyloxy-butane.

1,4-di-(dimethylamino)-2,3-butanediol (0.62 g, 3.50 mmol) was added to a stirred solution of sodium hydride (60%, 0.40 g, 10.5 mmol) in anhydrous THF (40 ml). The mixture was heated at reflux for 4 hr. Oleyl mesylate (3.64 g, 10.5 mmol) was added and the resulting mixture was heated at reflux for 48 hr. Water (50 ml) was added and the mixture was extracted with ethyl acetate (3×50 ml). The combined organic extracts were washed with saturated sodium hydrogencarbonate solution (50 ml) and brine (50 ml) and dried over anhydrous magnesium sulfate. The solvents were removed in vacuo. The product was purified by flash chromatography (gradient; DCM to 20% methanol in DCM) to obtain the titled product as an orange oil (0.40 g, 17%).

R$_f$=0.30 (10% methanol in DCM);

$\delta_H$ (300 MHz, CDCl$_3$) 0.91 (6H, t, J 6.93 Hz, CH$_2$CH$_3$), 1.25 (44H, m), 1.55 (4H, m, OCH$_2$CH$_2$), 2.00 (8H, m, CH$_2$CH=CHCH$_2$), 2.24 (14H, s+dd, NCH$_3$ and NCH$_2$), 2.55 (2H, dd, J 12.81 Hz and J 4.21 Hz, NCH$_2$), 3.50 (6H, m, CHO and OCH$_2$CH$_2$), 5.35 (4H, m, CH=CH);

$\delta_C$ (75 MHz, CDCl$_3$) 14.44 (CH$_2$CH$_3$), 23.04-32.96, 46.62 (NCH$_3$), 59.47 (NCH$_2$), 71.21 (OCH$_2$CH$_2$), 77.68 (CHO), 130.19 and 130.28 (CH=CH);

$\nu_{max}$ cm$^{-1}$ (Film) 3415.7, 2925.8, 2854.5, 2767.7, 2353.0, 2239.2, 1654.8, 1461.9, 1099.3;

The third step produced 1,4-di(trimethylammonium)-2,3-dioleyloxy-butane; diiodide

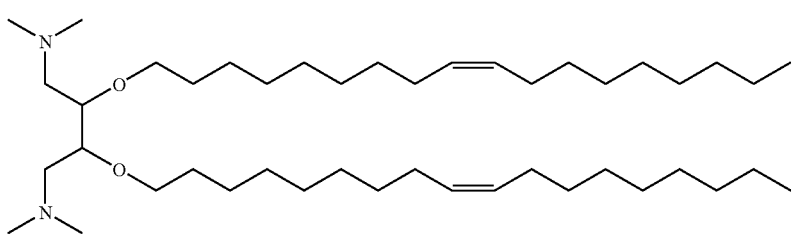

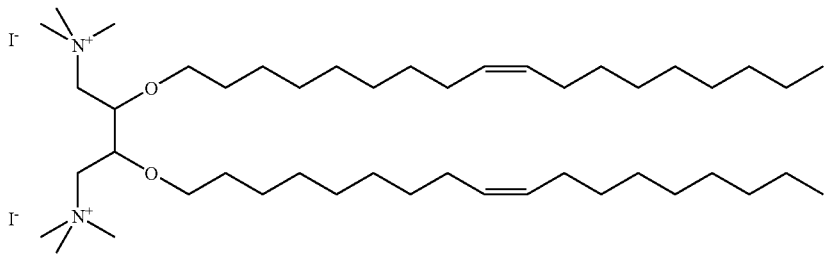

1,4-di(dimethylamino)-2,3-dioleyloxy-butane (305 mg, 0.45 mmol) is stirred in iodomethane (2.00 ml) in a sealed tube at 90° C. for 24 hr. Excess iodomethane was removed in vacuo. The product was recrystallized (ethyl acetate) to obtain the product as a waxy solid (366 mg, 85%).

$\delta_H$ (300 MHz, CDCl$_3$) 0.91 (6H, t, J 6.9 Hz, CH$_2$CH$_3$), 1.25 (44H, m), 1.55 (4H, m, OCH$_2$CH$_2$)) 2.00 (8H, m, CH$_2$CH=CHCH$_2$), 3.45 (18H, s, NCH$_3$), 3.75 (2H, m, OCH$_2$CH$_2$), 4.01 (6H, m, OCH$_2$CH$_2$ and NCH$_2$), 4.50 (2H, m, CHO), 5.35 (4H, m CH=CH);

$\delta_C$ (75 MHz, DEPT, CDCl$_3$) 14.44 (CH$_2$CH$_3$), 23.04-32.96, 55.93 (NCH$_3$), 68.26 (NCH$_2$), 72.49 (OCH$_2$CH$_2$), 73.54 (CHO), 130.19 and 130.28 (CH=CH);

m/z (ESP+) 353.6 (100%, ½M$^+$);

$v_{max}$ cm$^{-1}$ (nujol mull) 3418.6, 2916.6, 2864.6, 2718.5, 2353.9, 1625.9, 1464.8, 1376.6;

EXAMPLE 19

Transfection Efficiencies

The activity of various compositions of the invention was measured in HAE cells using a Luciferase assay. RLU/mg refers to relative light units per mg of protein. The assay was carried out as follows:

Lipid (10 mg/mL; 100 mL [1 mg of lipid]) in chloroform was placed into a glass vial (sterile). The solvents were removed in vacuo and further traces of chloroform were removed on the high vacuum for 24 h. Cationic lipids were either formulated alone or with DOPE (mole ratio, 1:1).

Deionized water (1 mL; MilliQ) was added to the film, to generate 1 mg/L solution of lipid in water. The mixture was allowed to hydrate at 4° C. for 24 h. After warming to 40° C. the mixture was sonicated to generate a clear solution (5 in approx). The resulting liposome formulations were stable for up to 3 months.

The components of the complex were mixed in the required weight ratio. The lipid was initially mixed with the peptide and the resulting mixture was added to the plasmid DNA.

Human airway epithelial cells were seeded for 24 h at 37 □C in complete growth medium in a 96 well plate. Transfection complexes were left to aggregate for 30 min and diluted to a concentration of 1 μg of DNA per 0.5 ml in OptiMEM (Life technologies). The medium was removed from each well and replaced with 0.5 ml of transfection complex and was allow to incubate for a further 4 h. The transfection complexes were removed and then replace with growth medium and the cells were allowed to incubate for 48 h.

The transfected cells were washed with phosphate-buffered saline (PBS). Reporter lysis buffer (100 μl) (Promega) was added to each well and cooled to 4 □C for 15 min. The cells were then assayed with a luciferase assay kit. The total light emission was measured for each well for 60 sec. The protein concentration of each sample was determined using a protein assay reagent and the activity expressed as relative light units per milligram of protein (RLU/mg).

The values obtained for the lipids produced in Examples 17 and 18 above and for Lipofectin were measured at 1:1 and 2:1 ratios of lipid:DNA, and in each case the ratio of peptide:DNA was 4:1, the peptide used being [K]$_{16}$ GACRRETAWACG. The ratios are expressed in terms of weight. The testing procedure used was that outlined in Human Gene Therapy 9, 575-585, 1998.

| | | |
|---|---|---|
| Example 17 | (1:1, lipid:DNA) C$_{18}$ Ester | 1.2 RLU/mg |
| Example 18 | (1:1, lipid:DNA) C$_{18}$ Ether | 43.2 RLU/mg |
| Lipofectin | (1:1, lipid:DNA) | 12.1 RLU/mg |
| Example 17 | (2:1, lipid:DNA) C$_{18}$ Ester | 2.0 RLU/mg |
| Example 18 | (2:1, lipid:DNA) C$_{18}$ Ether | 373.3 RLU/mg |
| Lipofectin | (2:1, lipid:DNA) | 51.6 RLU/mg |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A lipid of general formula (I) or (II):

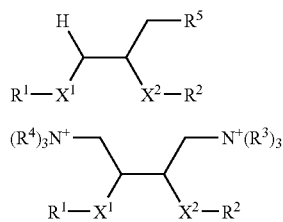

wherein
X$^1$ and X$^2$ are —O—;
R$^1$ and R$^2$ for formula I are the same or different and are straight or branched, saturated or unsaturated C$_7$ to C$_{24}$ hydrocarbyl groups which are unsubstituted or substituted by one or more substituents selected from the group consisting of hydroxy, halogen and OR', wherein R' is a C$_1$ to C$_6$ hydrocarbyl group and R$^1$ and R$^2$ for formula II are the same or different and are straight or branched unsaturated C$_7$ to C$_{24}$ hydrocarbyl groups or straight or branched saturated C$_{18}$ to C$_{24}$ hydrocarbyl groups, which are unsubstituted or substituted by one or more substituents selected from the group consisting of hydroxy, halogen and OR', wherein R' is a C$_1$ to C$_6$ hydrocarbyl group;

R$^5$ is —N$^+$(R$^3$)$_2$—R$^6$;

R$^6$ is either:

(a) -[A-Y]$_n$R$^4$ wherein:
each Y is the same or different and is —N$^+$(R$^4$)$_2$—;
each A is the same or different and is a C$_{1-20}$ alkylene group which is unsubstituted or substituted by one or more substituents selected from the group consisting of hydroxy, halogen, —OR', —C(O)OH, —CN, —NR'R", and —C(O)R' wherein R' and R" are the same or different and are $C_{1-6}$ hydrocarbyl; and n is an integer of from 1 to 10; or (b) —[B—O]$_m$B-Q wherein:

each B is the same or different and is a $C_{1-10}$ alkylene group which is unsubstituted or substituted by one or more substituents selected from the group consisting of hydroxy, halogen, —OR', —C(O)OH, —CN, —NR'R" and —C(O)R' wherein R' and R" are the same or different and are $C_{1-6}$ hydrocarbyl;

m is an integer of from 1 to 10; and

Q is selected from the group consisting of —N$^+$(R$^3$)$_3$, —OH, —OR', —OC(O)R' and halogen, wherein R' is as defined above; and each R$^3$ and each R$^4$ is the same or different and is a straight or branched, saturated or unsaturated $C_1$ to $C_{10}$ hydrocarbyl group which is unsubstituted or substituted by one or more substituents selected from the group consist of hydroxy, halogen, —OR', —C(O)OH, —CN, —NR'R", and —C(O)R' wherein R' and R" are the same or different and are $C_1$ to $C_6$ hydrocarbyl.

2. A lipid according to claim 1 wherein R$^1$ and R$^2$ are the same or different and represent a $C_{12-20}$ hydrocarbyl group.

3. A lipid according to claim 2 wherein R$^1$ and R$^2$ are the same or different and represent a $C_{14}$, $C_{16}$, $C_{18}$ or $C_{20}$ alkenyl group having one, two or three double bonds.

4. A lipid according to claim 3 wherein R$^1$ and R$^2$ are both $C_{16}$ or $C_{18}$ alkenyl groups having one double bond.

5. A lipid according to claim 1 wherein R$^5$ is —N$^+$(R$^3$)$_2$—R$^5$ and R$^6$ is —[B—O]$_m$B-Q, wherein:

each B is the same or different and is a $C_{1-6}$ alkylene group which is unsubstituted or substituted by one or more substituents selected from the group consisting of hydroxy, halogen, —OR', —C(O)OH, —CN, —NR'R" and —C(O)R' wherein R' and R" are the same or different and are $C_{1-4}$ hydrocarbyl;

m is an integer of from 1 to 8; and

Q is selected from the group consisting of —N$^+$(R$^3$)$_3$, —OH and —OR' wherein R' is a $C_{1-4}$ alkyl group.

6. A lipid according to claim 1, having the general formula (III):

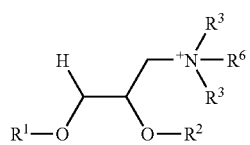

(III)

wherein

R$^1$ and R$^2$ are the same or different and are straight or branched, saturated or unsaturated $C_{12-20}$ hydrocarbyl groups which are unsubstituted or substituted by one or more substituents selected from the group consisting of hydroxy, halogen and —OR' wherein R' is a $C_{1-6}$ hydrocarbyl group;

each R$^3$ is the same or different and is a straight or branched, saturated or unsaturated $C_{1-6}$ hydrocarbyl group which is unsubstituted or substituted by one or more substituents selected from the group consisting of hydroxy, halogen, —OR', —COOH, —CN, —NR'R" and —COR' wherein R' and R" are the same or different and are $C_{1-4}$ hydrocarbyl;

R$^6$ is —[B—O]$_m$B-Q wherein each B is the same or different and is a $C_{1-6}$ alkylene group which is unsubstituted or substituted by one or more substituents selected from the group consisting of hydroxy, halogen, —OR', —C(O)OH, —CN, —NR'R" and —C(O)R' wherein R' and R" are the same or different and are $C_{1-4}$ hydrocarbyl; m is an integer of from 1 to 8; and Q is selected from the group consisting of —N$^+$(R$^3$)$_3$, —OH, —OR', —OC(O)R' and halogen wherein R' is as defined above.

7. A lipid according to claim 1, having the general formula (IV):

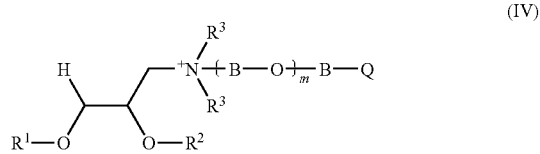

(IV)

wherein

R$^1$ and R$^2$ are the same or different and are selected from the group consisting of $C_{12-20}$ alkylene groups and $C_{12-20}$ alkenylene groups;

each R$^3$ is the same or different and is selected from unsubstituted $C_{1-4}$ alkyl groups;

each B is the same or different and is a $C_{1-6}$ alkylene group which is unsubstituted or substituted by one or more substituents selected from the group consisting of hydroxy, halogen, —OR', —C(O)OH, —CN, —NR'R" and —C(O)R' wherein R' and R" are the same or different and are $C_{1-4}$ hydrocarbyl;

m is an integer from 3 to 8; and

Q is selected from the group consisting of —N$^+$(R$^3$)$_3$, —OH, and —OR' wherein R' is an unsubstituted $C_{1-4}$ alkyl group.

8. A lipid according to claim 7 wherein R$^1$ and R$^2$ are both $C_{12-20}$ alkenylene groups having one double bond each.

9. A lipid according to claim 7 wherein each R$^3$ group is a methyl or ethyl group.

10. A lipid according to claim 7 wherein each B is the same or different and is an unsubstituted $C_{1-3}$ alkylene group.

11. A lipid according to claim 7 wherein m is selected from the group consisting of 3, 4, 5, 6 and 7.

12. A lipid according to claim 7 wherein Q is —OH or —OR' wherein R' is an unsubstituted $C_{1-4}$ alkyl group.

13. A lipid according to claim 1, selected from the group consisting of {2,3-Di-[(Z)-octadec-9-enyloxy]-propyl}-N-(2-{2-[2-(2-hydroxy-ethoxy)-ethoxy]-ethoxy}-ethyl)-N,N-dimethylammonium bromide; {2,3-Di-[(Z)-ocatadec-9-enyloxy]-propyl}-N-{2-[2-(2-{2-[2-(2-hydroxy-ethoxy)-ethoxy}-ethoxy)-ethoxy]-ethyl}-N,N-dimethylammonium bromide; {2,3-Di-[(Z)-hexadec-11-enyloxy]-propyl}-N-(2-{2-[2-(2-hydroxy-ethoxy)-ethoxy]-ethoxy}-ethyl)-N,N-dimethylammonium bromide; {2,3-Di-[(Z)-hexadec-11-enyloxy]-propyl}-N-{2-[2-(2-{2-[2-(2-hydroxy-ethoxy)-ethoxy]-ethoxy}-ethoxy)-ethoxy]-ethyl}-N,N-dimethylammonium bromide; and 1,4-Di(trimethylammonium)-2,2-dioleoyloxy-butane, diiodide.

14. A complex suitable for delivery of a biologically-active material to a cell, which complex comprises a lipid according to claim 1 and a biologically-active material.

15. A complex according to claim 14 wherein the biologically-active material is a nucleic acid, a peptide or a small molecule.

16. A complex according to claim 15 wherein the nucleic acid is a DNA or RNA.

17. A complex according to claim 14 which further comprises an integrin-binding peptide.

18. A process for the preparation of a complex comprising a lipid and a biologically-active material, which process comprises the step of admixing (i) a lipid according to claim 1 and (ii) a biologically-active material.

19. A process according to claim 18, wherein an integrin-binding peptide is admixed with said lipid and said biologically-active material.

* * * * *

UNITED STATES PATENT AND TRADEMARK OFFICE
CERTIFICATE OF CORRECTION

| | | |
|---|---|---|
| PATENT NO. | : 7,598,421 B2 | Page 1 of 1 |
| APPLICATION NO. | : 10/983464 | |
| DATED | : October 6, 2009 | |
| INVENTOR(S) | : Hailes et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 286 days Delete the phrase "by 286 days" and insert -- by 619 days --

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,598,421 B2
APPLICATION NO. : 10/983464
DATED : October 6, 2009
INVENTOR(S) : Hailes et al.

It is certified that error appears in the above-identified patent and that said Letters Patent is hereby corrected as shown below:

In the Claims

Column 89, Line 33, replace "$R^5$" with --$R^6$--.

Column 90, Line 66-67, replace "1,4-Di(trimethylammonium)-2,2-dioleoyloxy-butane, diiodide." with --1,4-Di(trimethylammonium)-2,3-dioleoyloxy-butane, diiodide.--.

Signed and Sealed this
Eighteenth Day of June, 2013

Teresa Stanek Rea
*Acting Director of the United States Patent and Trademark Office*

SEQUENCE LISTING

<160> NUMBER OF SEQ ID NOS: 22

<210> SEQ ID NO 1
<211> LENGTH: 8
<212> TYPE: PRT

-continued

```
<213> ORGANISM: Artificial Sequence
<220> FEATURE:
<223> OTHER INFORMATION: Synthetic

<400> SEQUENCE: 1

Cys Arg Gly Asp Met Phe Gly Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Gly Gly Cys Arg Gly Asp Met Phe Gly Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gly Gly Cys Arg Gly Asp Met Phe Gly Cys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gly Gly Cys Arg Gly Asp Met Phe Gly Cys Ala
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Gly Ala Cys Ala Thr Arg Trp Ala Arg Glu Cys Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Gly Ala Cys Arg Arg Glu Thr Ala Trp Ala Cys Ala
1               5                   10

<210> SEQ ID NO 7
<211> LENGTH: 15
<212> TYPE: PRT
<213> ORGANISM: Artificial Sequence
```

```
<220> FEATURE:
<223> OTHER INFORMATION: Synthetic
<220> FEATURE:
<221> NAME/KEY: VARIANT
<222> LOCATION: 1, 3
<223> OTHER INFORMATION: Xaa = Any Amino Acid

<400> SEQUENCE: 7

Xaa Ser Xaa Gly Ala Cys Arg Arg Glu Thr Ala Trp Ala Cys Gly
 1               5                  10                  15

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Cys Arg Arg Glu Thr Thr Ala Trp Ala Cys
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Cys Arg Arg Glu Thr Ala Trp Ala Cys
 1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Gly Ala Cys Arg Gly Asp Met Phe Gly Cys Ala
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Gly Ala Cys Arg Gly Asp Met Phe Gly Cys Gly Gly
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gly Ala Cys Asp Cys Arg Gly Asp Cys Phe Cys Ala
 1               5                  10

<210> SEQ ID NO 13
```

```
<211> LENGTH: 12
<212> TYPE: PRT
<213> ORGANISM: Artificial Sequence
<220> FEATURE:
<223> OTHER INFORMATION: Synthetic

<400> SEQUENCE: 13

Gly Ala Cys Arg Arg Glu Thr Ala Trp Ala Cys Gly
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Gly Ala Gly Pro Glu Ile Leu Asp Val Pro Ser Thr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Gly Ala Cys Gln Ile Asp Ser Pro Cys Ala
1               5                   10

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

Gly Ala Cys Arg Arg Glu Thr Ala Trp Ala Cys Gly Lys Gly Ala Cys
1               5                   10                  15

Arg Arg Glu Thr Ala Trp Ala Cys Gly
            20                  25

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Gly Ala Cys Ser Glu Arg Ser Met Asn Phe Cys Gly
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Gly Ala Cys Tyr Gly Leu Pro His Lys Phe Cys Gly
1               5                   10
```

-continued

```
<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Gly Ala Cys Pro Ser Gly Ala Ala Arg Ala Cys Gly
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Gly Ala Cys Val Lys Ser Met Val Thr His Cys Gly
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Synthetic

<400> SEQUENCE: 21

Gly Ala Cys Leu Gln His Lys Ser Met Pro Cys Gly
 1               5                  10

<210> SEQ ID NO 22
<211> LENGTH: 28
<212> TYPE: PRT
<213> ORGANISM: Artificial Sequence
<220> FEATURE:
<223> OTHER INFORMATION: Synthetic

<400> SEQUENCE: 22

Lys Lys Lys Lys Lys Lys Lys Lys Lys Lys Lys Lys Lys Lys Lys Lys
 1               5                  10                  15

Gly Ala Cys Arg Arg Glu Thr Ala Trp Ala Cys Gly
            20                  25
```